US012653669B2

(12) United States Patent
Hofferberth et al.

(10) Patent No.: US 12,653,669 B2
(45) Date of Patent: Jun. 16, 2026

(54) GEOMETRICALLY-ACCOMMODATING HEART VALVE REPLACEMENT DEVICE

(71) Applicant: The Children's Medical Center Corporation, Boston, MA (US)

(72) Inventors: Sophie-Charlotte Hofferberth, Boston, MA (US); Pedro J. del Nido, Lexington, MA (US); Mossab Y. Saeed, Revere, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 18/618,560

(22) Filed: Mar. 27, 2024

(65) Prior Publication Data

US 2024/0315837 A1 Sep. 26, 2024

Related U.S. Application Data

(63) Continuation of application No. 18/351,785, filed on Jul. 13, 2023, now Pat. No. 11,969,342.

(Continued)

(51) Int. Cl.
*A61F 2/24* (2006.01)
(52) U.S. Cl.
CPC .......... *A61F 2/2418* (2013.01); *A61F 2/2412* (2013.01); *A61F 2/243* (2013.01); *A61F 2220/0075* (2013.01); *A61F 2250/001* (2013.01); *A61F 2250/0029* (2013.01); *A61F 2250/0051* (2013.01); *A61F 2250/006* (2013.01); *A61F 2250/0069* (2013.01); *A61F 2250/0082* (2013.01)

(58) Field of Classification Search
CPC ............ A61F 2/24–2424; A61F 2/2475; A61F 2250/0082
See application file for complete search history.

(56) References Cited

U.S. PATENT DOCUMENTS 10,932,904 B2    3/2021    Lee et al.
10,966,826 B2    4/2021    Hofferberth et al.
(Continued)

FOREIGN PATENT DOCUMENTS

WO        WO 99/04730 A1     2/1999
WO        WO 2012/018779 A3  5/2012
(Continued)

OTHER PUBLICATIONS

International Search Report and Written Opinion mailed Dec. 4, 2023, in connection with International Application No. PCT/US2023/027599.
(Continued)

*Primary Examiner* — Rebecca S Preston
(74) *Attorney, Agent, or Firm* — Wolf, Greenfield & Sacks, P.C.

(57) ABSTRACT

A replacement heart valve device is disclosed. In some embodiments, the device includes a frame coupled to one or more leaflets that are moveable between open and closed configurations. In some embodiments, the frame comprises at least two frame sections that join at a pair of commissural posts. In some embodiments, the device may be geometrically accommodating to adapt to different vasculature shapes and sizes and/or to be able to change size while implanted within a growing patient.

14 Claims, 45 Drawing Sheets

Related U.S. Application Data

(60) Provisional application No. 63/394,742, filed on Aug. 3, 2022.

(56) References Cited

U.S. PATENT DOCUMENTS

| | | | |
|---|---|---|---|
| 11,376,123 | B2 | 7/2022 | Gründeman et al. |
| 11,969,342 | B2 | 4/2024 | Hofferberth et al. |
| 12,004,948 | B2 | 6/2024 | Hofferberth et al. |
| 2003/0014104 | A1 | 1/2003 | Cribier |
| 2004/0260389 | A1 | 12/2004 | Case et al. |
| 2005/0075584 | A1 | 4/2005 | Cali |
| 2007/0288087 | A1 | 12/2007 | Fearnot et al. |
| 2009/0054973 | A1 | 2/2009 | Johnson |
| 2009/0254176 | A1 | 10/2009 | Butera |
| 2011/0098802 | A1 | 4/2011 | Braido et al. |
| 2012/0101571 | A1 | 4/2012 | Thambar et al. |
| 2013/0018453 | A1 | 1/2013 | Case et al. |
| 2016/0000567 | A1 | 1/2016 | Melzer et al. |
| 2016/0158013 | A1 | 6/2016 | Carpentier et al. |
| 2016/0220361 | A1 | 8/2016 | Weber et al. |
| 2017/0014228 | A1 | 1/2017 | Emani et al. |
| 2017/0065411 | A1 | 3/2017 | Grundeman et al. |
| 2017/0095331 | A1 | 4/2017 | Spenser et al. |
| 2017/0189175 | A1 | 7/2017 | Justino et al. |
| 2017/0252156 | A1 | 9/2017 | Bernstein et al. |
| 2017/0333188 | A1 | 11/2017 | Carpentier et al. |
| 2019/0105153 | A1* | 4/2019 | Barash ................. A61F 2/2418 |
| 2020/0360135 | A1 | 11/2020 | Hofferberth et al. |
| 2020/0368017 | A1 | 11/2020 | Hofferberth et al. |
| 2021/0322162 | A1* | 10/2021 | Tayeb ................... A61F 2/2415 |
| 2021/0330457 | A1 | 10/2021 | Colavito et al. |
| 2021/0353443 | A1 | 11/2021 | King et al. |
| 2022/0008233 | A1* | 1/2022 | Nia ......................... A61F 2/915 |
| 2023/0225862 | A1 | 7/2023 | Yohanan et al. |
| 2023/0270540 | A1* | 8/2023 | Schwartz .............. A61F 2/2415 623/2.1 |
| 2024/0041595 | A1 | 2/2024 | Hofferbeth et al. |
| 2024/0358502 | A1 | 10/2024 | Hofferberth et al. |

FOREIGN PATENT DOCUMENTS

| | | | |
|---|---|---|---|
| WO | WO 2019/099864 A1 | 5/2019 | |
| WO | WO 2019/099864 A8 | 7/2019 | |

OTHER PUBLICATIONS

Invitation to Pay Additional Fees mailed Oct. 11, 2023, in connection with International Application No. PCT/US2023/027599.

* cited by examiner

Fig. 13B        Fig. 13C

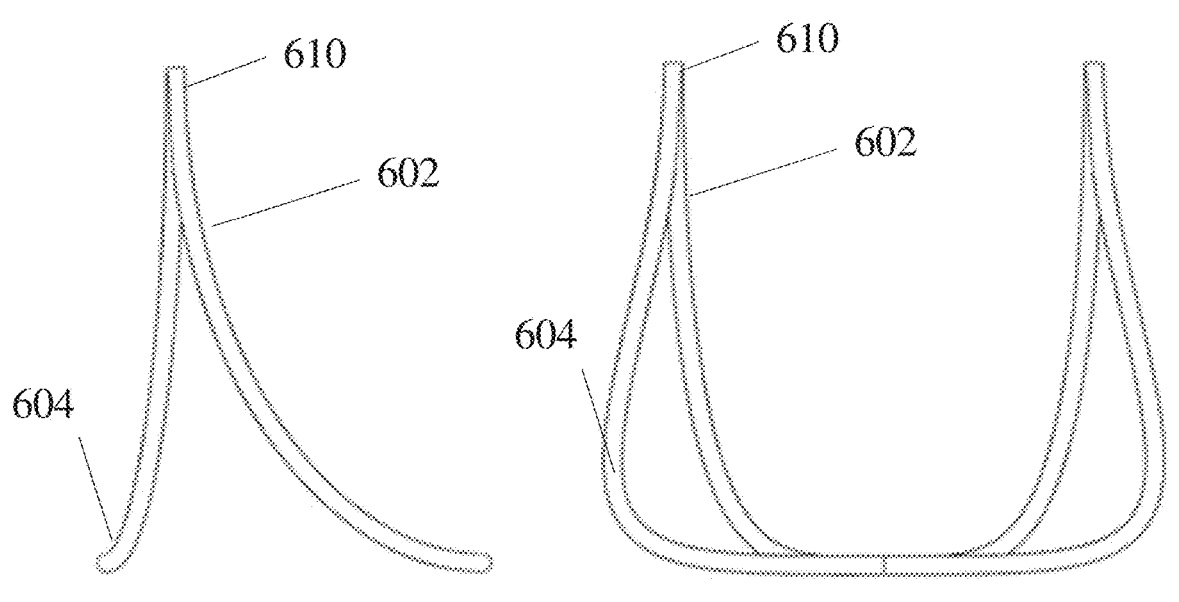
Fig. 16A          Fig. 16B
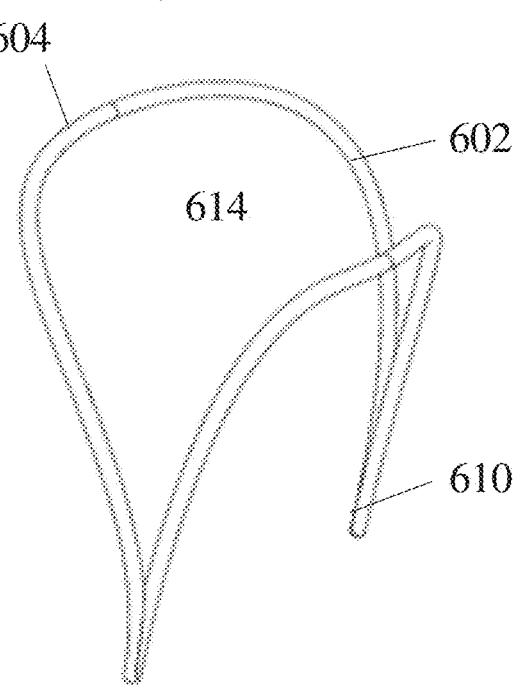
Fig. 16C          Fig. 16D

Fig. 20A          Fig. 20B

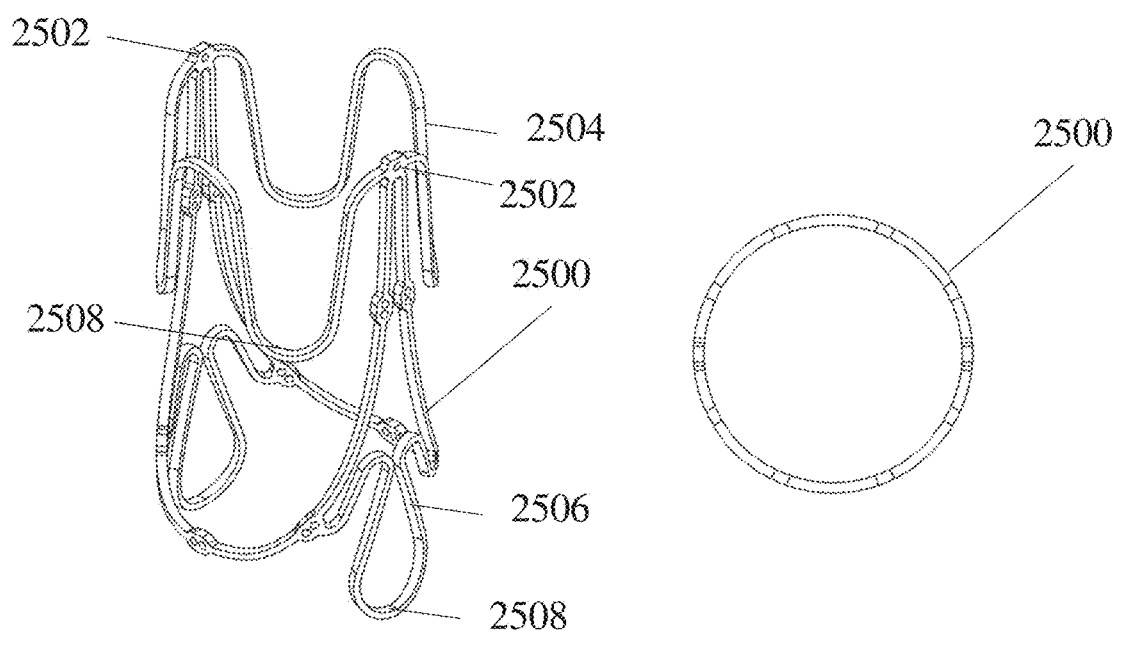
Fig. 25A
Fig. 25B
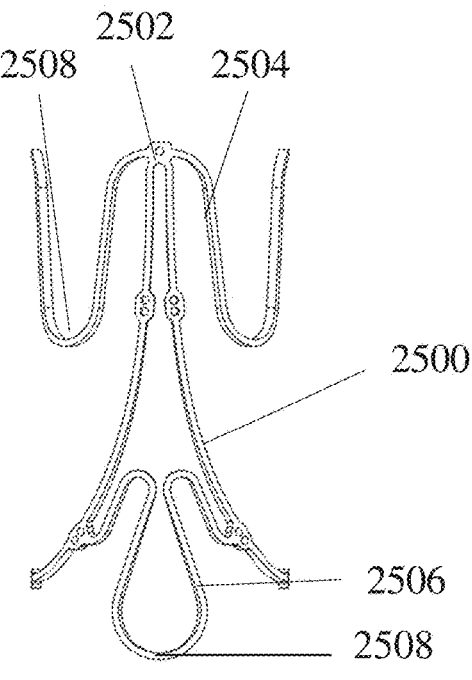
Fig. 25C
Fig. 25D

|  | Mean PA pressure (mmHg) | Diastolic pressure (mmHg) | Transvalvular gradient (mmHg) | | Effective orifice area (cm²) | Forward flow volume (ml) | Closing volume (ml) | leakage volume (ml) | Regurgitation fraction (%) (% of forward flow volume) |
|---|---|---|---|---|---|---|---|---|---|
|  |  |  | Mean | Peak |  |  |  |  |  |
| Right Heart | 20 | 14.1 | 9.2 | 16.7 | 0.6 | 20.6 | 1.5 | 1.1 | 6 |
| left Heart | 58.1 | 50.7 | 8.9 | 18.5 | 0.6 | 19.6 | 1.7 | 1.5 | 7 |

1.8X geometry: Valve ID = 23 mm

|  | Mean PA pressure (mmHg) | Diastolic pressure (mmHg) | Transvalvular gradient (mmHg) | | Effective orifice area (cm²) | Forward flow volume (ml) | Closing volume (ml) | leakage volume (ml) | Regurgitation fraction (%) (% of forward flow volume) |
|---|---|---|---|---|---|---|---|---|---|
|  |  |  | Mean | Peak |  |  |  |  |  |
| Right Heart | 20 | 14.1 | 9.2 | 16.7 | 0.6 | 20.6 | 1.5 | 1.1 | 6 |
| left Heart | 58.1 | 50.7 | 8.9 | 18.5 | 0.6 | 19.6 | 1.7 | 1.5 | 7 |

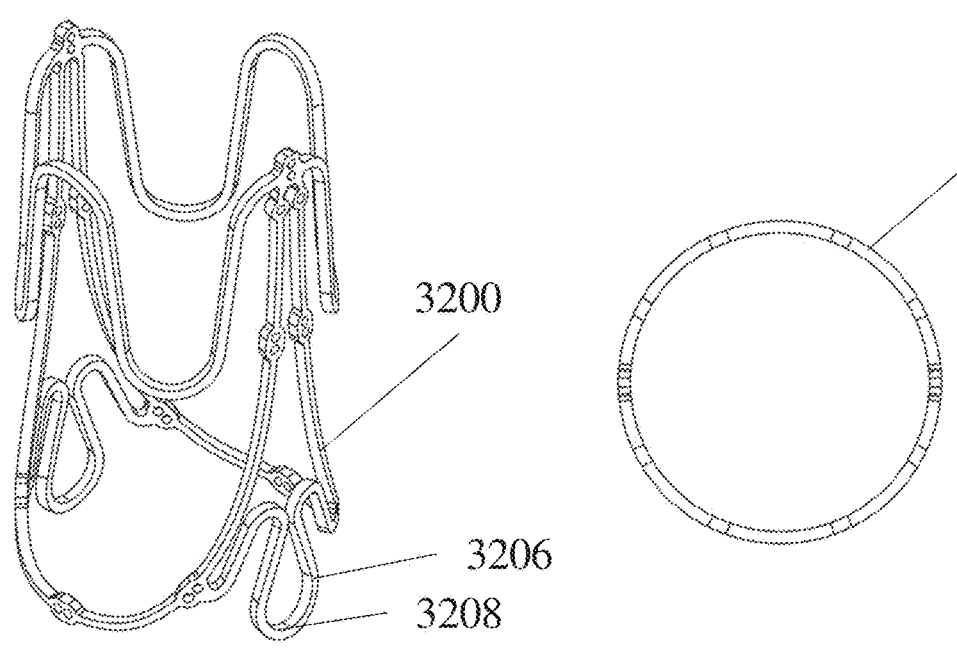
3200
3206
3208
Fig. 33A
3200
Fig. 33B
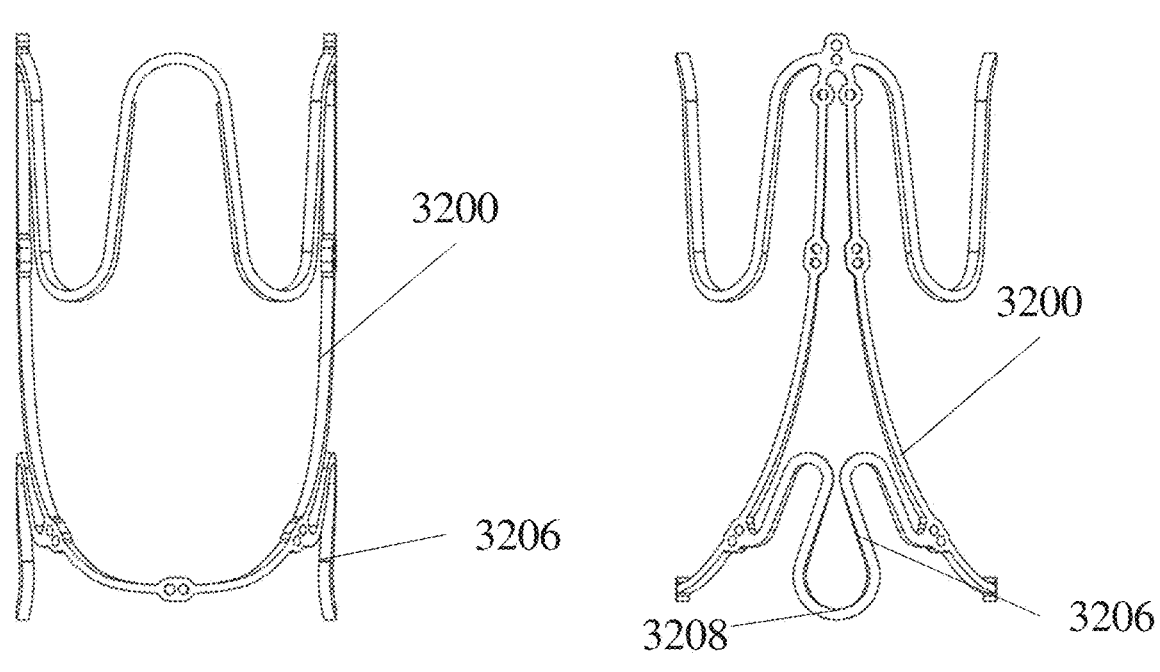
3200
3206
Fig. 33C
3200
3206
3208
Fig. 33D

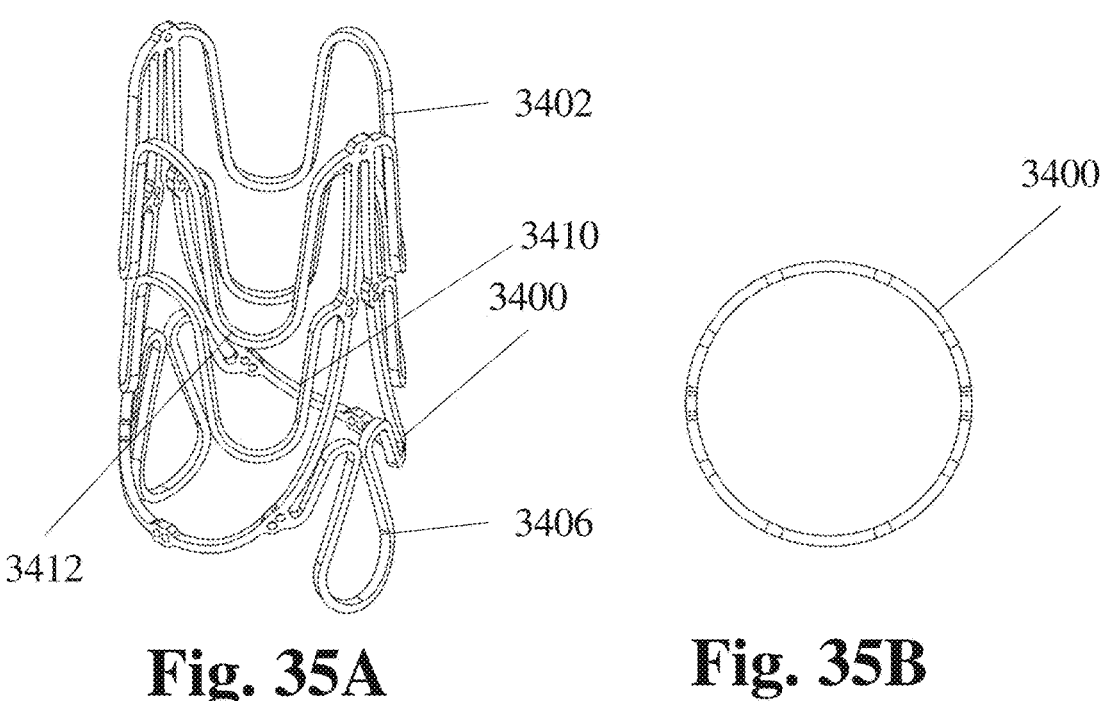
3402
3410
3400
3406
3412
Fig. 35A          Fig. 35B
3400
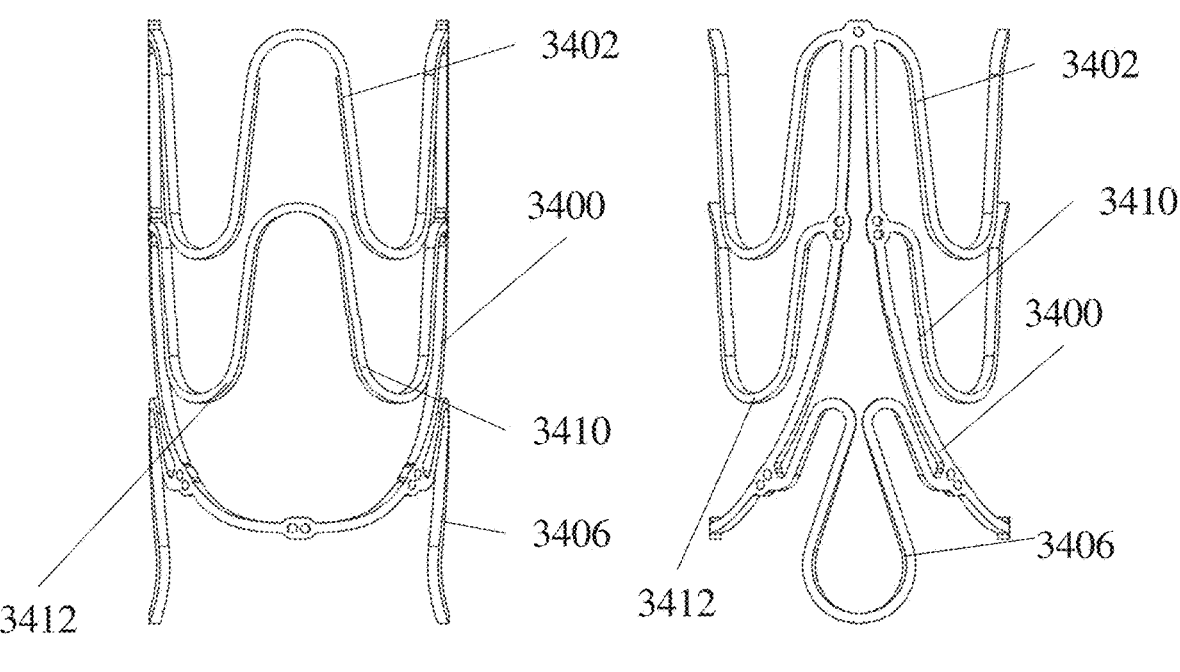
3402
3400
3410
3406
3412
3402
3410
3400
3406
3412
Fig. 35C          Fig. 35D

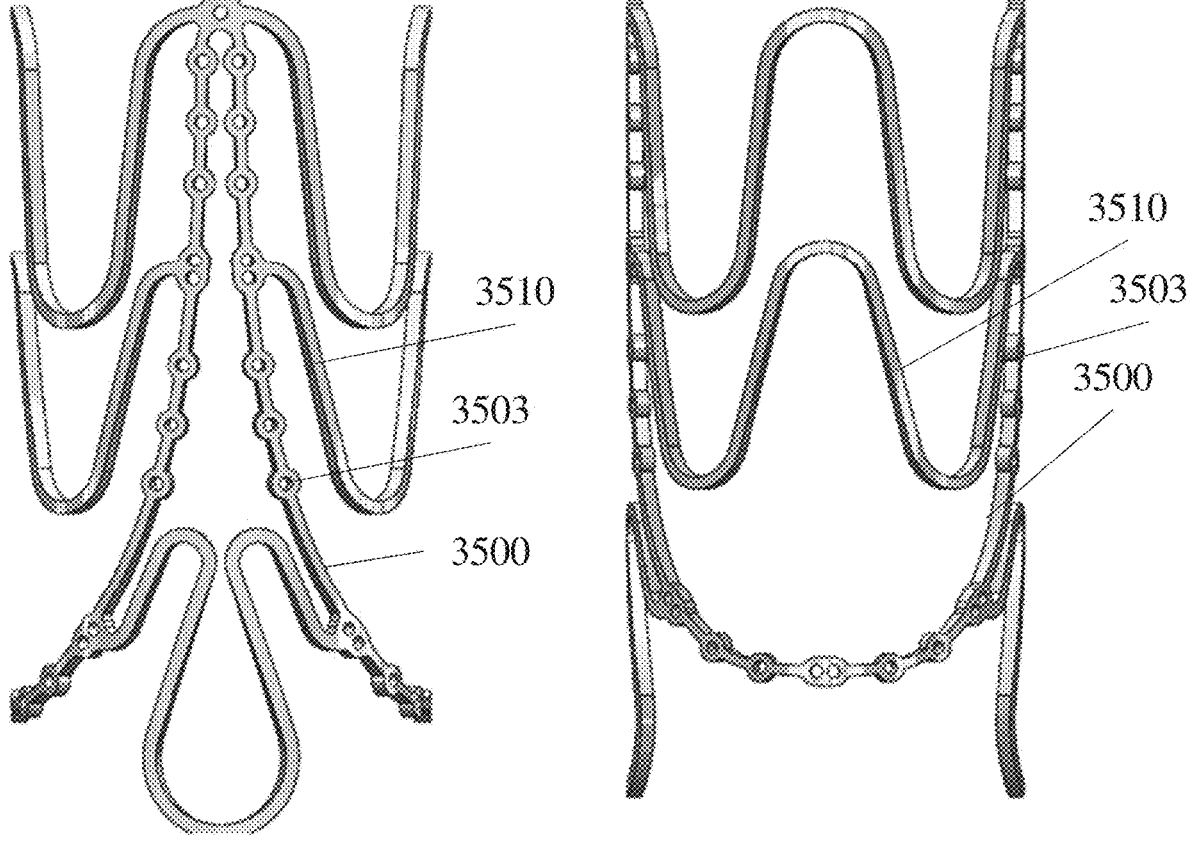
3510
3503
3500
Fig. 36A         Fig. 36B

3200

106

106

3200

106

3200

106

106

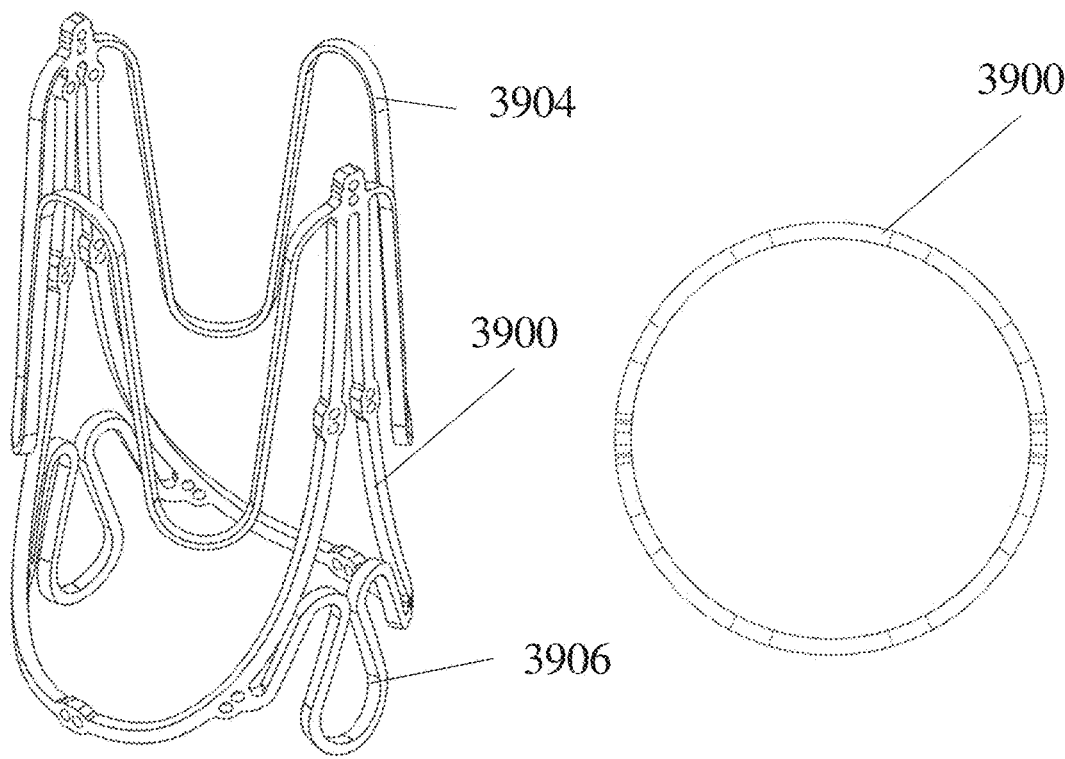
Fig. 39A            Fig. 39B
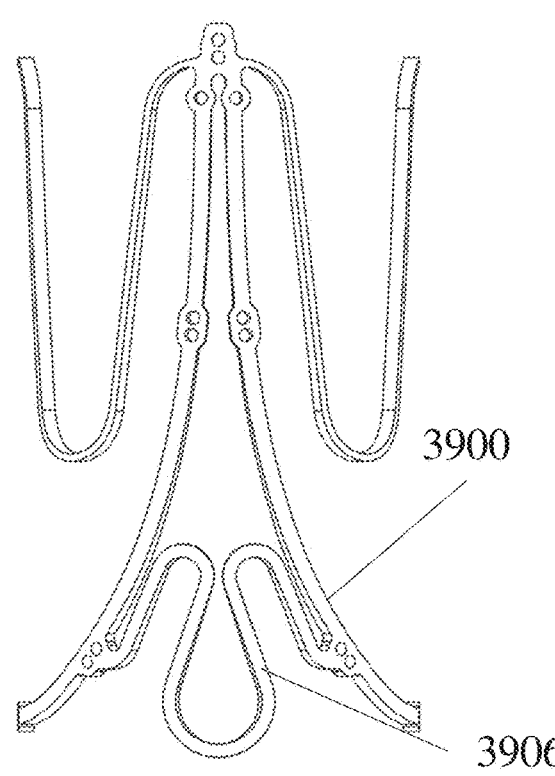
Fig. 39C            Fig. 39D

3300

4004

4003

4001

3300

4003

4001

4004

GEOMETRICALLY-ACCOMMODATING HEART VALVE REPLACEMENT DEVICE

CROSS-REFERENCE TO RELATED APPLICATION

This application is a continuation of U.S. patent application Ser. No. 18/351,785, filed Jul. 13, 2023, which claims the benefit of U.S. Provisional Application No. 63/394,742, filed Aug. 3, 2022, the entire contents of each of which are incorporated herein by reference.

FIELD

Disclosed embodiments are related to valve replacement devices.

BACKGROUND

The human heart includes a series of valves that work to ensure that blood flows correctly through the chambers of the heart. Birth defects, trauma, or other pathologies can negatively impact the function of a person's native heart valves. Prosthetic heart valves have been developed to either supplement or entirely replace defective native heart valves.

SUMMARY

In one embodiment, a valve replacement device is provided. The valve replacement device includes a valve frame defining an opening for the passage of fluid, a valve leaflet coupled to the valve frame and a sleeve coupled to the valve frame. The valve frame is expandable to permit an increase in the diameter of the opening. The valve frame has a plurality of holes through the valve frame. The valve leaflet is coupled to the valve frame using at least some of the plurality of holes through the valve frame. The valve leaflet has an open configuration in which the opening is exposed, and a closed configuration in which the valve leaflet at least partially covers the opening. The valve leaflet is configured to be moveable between the open and closed configurations over the diameter size range of the opening. The sleeve is coupled to the valve frame using at least some of the plurality of holes through the valve frame. The sleeve has a first expandable direction orientated to permit the increase in the diameter of the opening of the valve frame.

In another embodiment, a valve replacement device is provided. The valve replacement device includes a valve frame defining an opening for the passage of fluid, a first leaflet coupled to the valve frame, and a second leaflet coupled to the valve frame. The valve frame is expandable to permit an increase in the diameter of the opening. The valve frame has a plurality of holes through the valve frame. The first and second leaflets are coupled to the valve frame using at least some of the plurality of holes through the valve frame. The first and second leaflets each have an outer edge. The first leaflet has an open configuration in which the opening is exposed, and a closed configuration in which the first leaflet at least partially covers the opening. The second leaflet has an open configuration in which the opening is exposed, and a closed configuration in which the first and second leaflets contact one another to at least partially cover the opening. The first and second leaflets are configured to be moveable between the open and closed configurations over the diameter size range of the opening. The first and second leaflets have a plurality of leaflet attachment points for coupling the first and second leaflets to the valve frame.

The plurality of leaflet attachment points are located a non-uniform distance from the outer edges of the first and second leaflets.

In another embodiment, a valve replacement device is provided. The valve replacement device includes a valve frame defining an opening for the passage of fluid, a first leaflet coupled to the valve frame, and a second leaflet coupled to the valve frame. The valve frame is expandable to permit an increase in the diameter of the opening. The valve frame has a plurality of holes through the valve frame. The first and second leaflets arc coupled to the valve frame using at least some of the plurality of holes through the valve frame. The first and second leaflets each have an outer edge. The first and second leaflets each have at least one attachment tab. The first leaflet has an open configuration in which the opening is exposed, and a closed configuration in which the first leaflet at least partially covers the opening. The second leaflet has an open configuration in which the opening is exposed, and a closed configuration in which the first and second leaflets contact one another to at least partially cover the opening. The first and second leaflets are configured to be moveable between the open and closed configurations over the diameter size range of the opening.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 13B is a front view of the frame of FIG. 12 undergoing some expansion;

FIG. 13C is a top view of the frame of FIG. 12 undergoing some expansion;

FIG. 16A is a side view of another embodiment of the frame of the valve replacement device;

FIG. 16B is a front view of the frame of FIG. 16A;

FIG. 16C is a top view of the frame of FIG. 16A;

FIG. 16D is an inverted perspective view of the frame of FIG. 16A;

FIG. 25A is a perspective view of one embodiment of a valve frame of a valve replacement device;

FIG. 25B is a top view of the valve frame of FIG. 25A;

FIG. 25C is a front view of the valve frame of FIG. 25A;

FIG. 25D is a side view of the valve frame of FIG. 25A;

FIG. 33A is a perspective view of a valve frame of a valve replacement device according to one embodiment;

FIG. 33B is a top view of the valve frame according to the embodiment of FIG. 33A;

FIG. 33C is a front view of the valve frame according to the embodiment of FIG. 33A;

FIG. 33D is a side view of the valve frame according to the embodiment of FIG. 33A;

FIG. 35A is a perspective view of one embodiment of a valve frame of a valve replacement device;

FIG. 35B is a top view of the valve frame according to the embodiment of FIG. 35A;

FIG. 35C is a front view of the valve frame according to the embodiment of FIG. 35A;

FIG. 35D is a side view of the valve frame according to the embodiment of FIG. 35A;

FIG. 36A is a side view of one embodiment of a valve frame of a valve replacement device;

FIG. 36B is a front view of the valve frame of FIG. 36A;

FIG. 39A is a perspective view of a valve frame of a valve replacement device according to one embodiment;

FIG. 39B is a top view of the valve frame according to the embodiment of FIG. 39A;

FIG. 39C is a front view of the valve frame according to the embodiment of FIG. 39A;

FIG. 39D is a side view of the valve frame according to the embodiment of FIG. 39A;

DETAILED DESCRIPTION

Figures 1A, 1B:
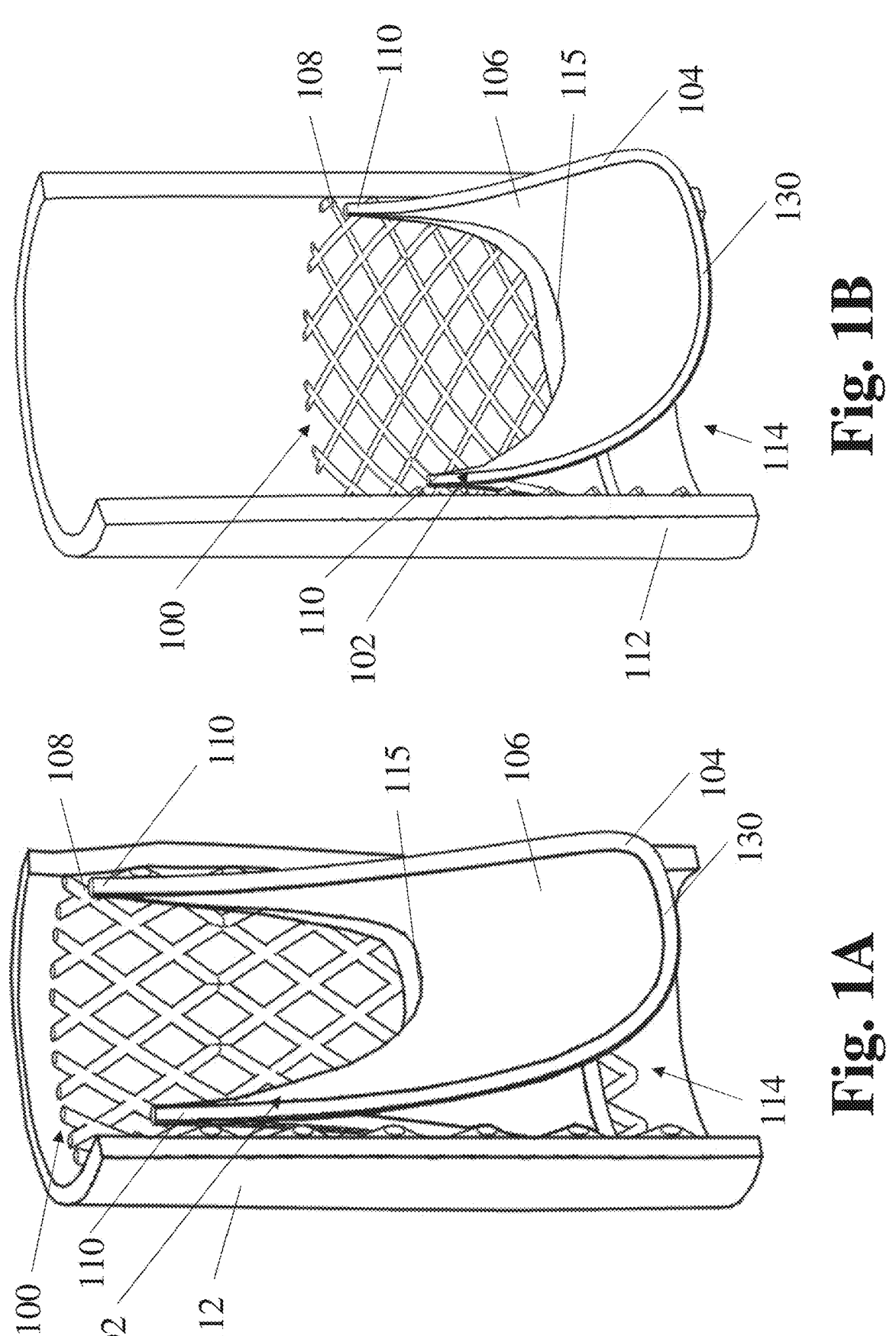
FIG. 1A is a perspective, partial section view of a vessel with a valve replacement device implanted within, prior to expansion.
FIG. 1B is a perspective, partial section view of the vessel and valve replacement device of FIG. 1A with the device having undergone some expansion.

Some embodiments described herein include a heart valve replacement device that is able to change in size and/or shape to adapt to different implantation environments. In some embodiments, such geometrically-accommodating heart valve replacement devices may be able to adapt to fit with different types of vasculature and/or used with differently sized patients. In some embodiments, some heart valve replacement devices described herein may be used in growing patients and may grow with the patient.

In some embodiments, it is contemplated that the device may also be used elsewhere in the vascular system apart from the heart, for example, as a venous valve prosthesis.

According to one aspect, some embodiments of the heart valve replacement device may enable heart valve function in a diverse range of structural environments, across a range of sizes. The inventors have recognized the need for a heart valve replacement device that is able to change in size and/or shape in order to accommodate varying environments.

According to one aspect, some embodiments of the heart valve replacement device grow with the patient and maintain functionality across a range of sizes as the valve opening increases in size. Current heart valve prosthetics are designed for adults and are intended to remain implanted for potentially up to decades at a time depending on the patient and the condition. Adult patients are commonly expected to get regular check-ups to ensure that the valve has not narrowed or become displaced to ensure optimal function. In some cases, adjusting or replacing a valve can require open-heart surgery. In adults, vasculature lumen diameters and heart sizes do not generally change significantly from year to year. However, in children, vasculature and hearts grow significantly in size as they mature. The inventors have appreciated that, as a result, with current devices, children who have undergone valve replacement have to undergo multiple procedures as they grow to implant suitably-sized valve replacement devices. The inventors have recognized the need for a valve replacement device that is effective over a range of sizes.

While some embodiments described herein are suitable for use in growing patients, it should be appreciated that the heart valve replacement devices described herein are not limited for use in growing patients. The devices may be used in non-growing applications as well. For example, some embodiments may be used as an adult transcatheter valve that can be size-adjusted post deployment for at least the reasons of addressing prosthesis-patient mismatch and para-valvular leakage that occurs in existing transcatheter valves.

In some embodiments, a first valve replacement device may be implanted in the first few years of a patient's life, and once the device reaches a full state of expansion, a second valve may be deployed inside the initial implanted device to enable the patient to avoid repeat open-heart procedures.

In some embodiments, it is contemplated that the valve replacement device may also function as a valve within an expandable conduit, which may be a cylindrical tube connecting two heart structures, or some other expandable conduit system. For example, the valve replacement device of some embodiments may be affixed to a cylindrical tube made of expandable synthetic material that acts as a right ventricle to a pulmonary artery conduit. In these embodiments, the valved conduit may be expanded periodically via a transcatheter balloon dilation or other method to accommodate somatic growth of the patient and/or adjusted to match desired pressure and/or flow conditions.

Heart valve function can be characterized by different properties. One measure of heart valve function is regurgitant fraction, which is the amount of blood that leaks backwards through the valve against the intended direction of flow divided by the total amount of blood that flows through the heart valve in one stroke. A healthy, functional valve exhibits low amounts of regurgitation. The inventors have appreciated that, in some cases, a regurgitant fraction of 0%-20% is desirable. Another measure of heart valve function is the amount of mean and peak transvalvular pressure gradient exhibited by the valve. This pressure metric is of interest because it quantifies valve function in allowing unimpeded forward flow. The inventors have appreciated that, in some cases, a peak transvalvular pressure gradient of 0 mmHg-40 mmHg for the right side of the heart and 0 mmHg-30 mmHg for the left side of the heart is desirable.

In some embodiments, the valve replacement device includes one or more leaflets coupled to a frame. The leaflets surround an opening of the device through which blood can flow. The leaflets have an open configuration and a closed configuration. In the open configuration, the leaflets part and expose the opening of the device to permit blood flow through the opening. In the closed configuration, the leaflets coapt and obstruct the opening of the device to prevent backflow of blood. The leaflets move between the open and closed configurations based on the pressure differentials across the valve during the cardiac cycle. In some embodiments, the device includes two leaflets. However, other numbers of leaflets may be used, such as three, four, five or more leaflets. In some embodiments, the heart replacement device includes only one leaflet. The single leaflet may extend from one side of the frame to the other. In some embodiments, the leaflets are moon-shaped, e.g., ¾ to ½ moon shaped leaflets.

In some embodiments, the frame may comprise a pair of semi-elliptical frame sections joined at a pair of commissures. The frame sections curve laterally outwards away from each other, forming a half-hourglass shape. As the surrounding vasculature widens, the two frame sections spread further apart at the open end, increasing the opening of the device and matching the cross-sectional area of the expanding lumen to accommodate growth. Each leaflet may be attached to the inner perimeter of each of the frame sections, mimicking the leaflet vessel wall attachment line of a native venous valve.

In some embodiments, the device includes an outer frame support coupled to the frame. In some embodiments, the outer frame support may be a semi-rigid cylindrical mesh. The frame is attached to the inside of, and is kept stable by, the outer frame support. Due to the rigidity of the outer frame support, the outer surface of the outer frame support presses against the inner walls of the vasculature in which the device is implanted, keeping the lumen of the surrounding vasculature open and maintaining the orientation and position of the device. The outer frame support can function similarly to a stent, allowing the device to be delivered via catheter delivery or direct surgical implantation. It should be appreciated however, that, in some embodiments, the frame may be used on its own without the addition of the outer frame.

According to one aspect, in some embodiments, the frame of the valve replacement device maintains a constant perimeter length (e.g., the site of leaflet attachment is non-lengthening) throughout the growth process, i.e., the perimeter length does not stretch or elongate during growth. Instead, as the frame sections spread apart to accommodate growth, the height of the commissures reduces. In some embodiments of this non-lengthening design, accommodation of radial growth is achieved by balloon expanding a plastically-deformable material (e.g., steel, cobalt chromium, etc.). As a result, the leaflets attached to the frame sections do not become deformed (i.e., do not stretch, lengthen or unfold) as the valve opening expands. The extent of coaptation of the leaflets (i.e., length of leaflet material in contact with other valve leaflets in closed state) may decrease as the opening expands.

In some embodiments, the frame sections of the frame are configured to maintain their shape as the device expands to accommodate growth, and thus the leaflets are not distended or stretched over the course of growth.

In an alternative embodiment, rather than preserving a constant perimeter length of the frame as the opening of the device grows, the frame may lengthen as the device grows. This may serve to decrease the amount of height change that the device undergoes during opening expansion. The frame may be made from any suitable material and/or may be constructed in any suitable form to permit the frame perimeter to lengthen as the device grows. For example, the frame may be made from an elastic material that can elastically stretch and elongate, may include telescoping segments, may include bio-erodible segments, or may include any other suitable mechanism that would allow the frame perimeter to elongate while the frame segments spread out away from one another.

In some embodiments, the frame may include segments having a bio-erodible outer sleeve with a core comprising telescoping or folded flexible segments. As the outer sleeve erodes, the core becomes exposed. When the vasculature expands, the radial pulling force on the frame causes the core to expand or unfold, allowing the frame to expand.

In some embodiments of the valve replacement device, the frame expands laterally outwards asymmetrically in that the frame sections move apart at different rates. The shape of each frame section may be maintained throughout growth/expansion, but the opening may grow more in one direction than the other. To accomplish the asymmetric expansion, these embodiments could have frame sections made from materials of differing stiffness or could have angled commissures such that expansion favors one side over the other.

The frame and/or outer frame support may be self-expanding or may expanded by other means, such as by balloon expansion.

The valve replacement device may be delivered via minimally invasive means such as by a transcatheter approach or may be implanted via open-heart surgery.

In some embodiments, the curve profile of the arcs of the frame sections can be obtained by projecting an elliptical quadrant on to a cylinder. It is contemplated that the cylinder could be representative of the shape of the inner wall of a vessel. The cylinder would have a radius equivalent to that of the valve held by the valve frame. The other frame section would match the projected curve profile but mirrored about the centerline of the cylinder. It should be understood that other frame section shapes and curve profiles are contemplated as well. However, it is also contemplated that other possible methods of defining the shape of the frame sections are contemplated and the current disclosure is not so limited. The frame sections may also have other shapes.

In some embodiments, a valve replacement device may include reinforcement features such as struts that connect the two frame sections of the valve frame. Such reinforcement struts may serve to maintain the shape of the valve frame during expansion. Some embodiments of the valve replacement device may include a top reinforcement strut that connects the two frame sections. The top reinforcement strut may be attached to the frame at or near the top of the pairs of commissures. The top reinforcement strut may have a length that is equal to or greater than the circumference of the frame opening at its maximum expansion diameter. The top reinforcement strut may form an annulus, or an ellipse, or may be asymmetrically shaped in its fully expanded state. In a non-expanded shape, the top reinforcement strut may have an undulating profile extending about a longitudinal axis of the valve replacement device such that the top reinforcement strut has a circular or elliptical or asymmetric profile when viewed from the top regardless of the state of the valve replacement device's expansion. In some embodiments, the top reinforcement strut may have undulations that gives the top reinforcement strut a smaller diameter before expansion of the frame but allowing the top reinforcement strut to expand with the frame. The top reinforcement strut may be comprised of a material with sufficient stiffness to provide reinforcing integrity to the frame as it expands, but with enough flexibility to allow the undulations to straighten out to permit the top reinforcement strut to expand.

In other embodiments, the top reinforcement strut may have a variety of different geometries that may be varied according to the application of the valve replacement device. For example, the top reinforcing feature may be diamond shaped to more readily allow the valve to be compressed over a catheter for percutaneous transvenous or transarterial valve deployment. Other shapes are also contemplated, and the current disclosure is not so limited.

Other shapes for the top reinforcement feature are contemplated. For instance, the top reinforcement feature could comprise multiple expandable segments connecting the frame sections instead of a single annulus. The segments could be telescoping segments or be otherwise folded or compressed to allow the feature to expand. The top reinforcement strut could also take on non-annular shapes as long as the feature can expand with the frame and fit within the implanted environment.

Some embodiments of the valve replacement device could include reinforcement features not attached to the commissures of the valve frame. For instance, some embodiments could have a lower reinforcement strut connecting the respective lower sides of the frame sections to each other. The lower reinforcement struts may also have an undulating or otherwise compressed or folded shape that allows the lower feature to expand with the frame. Similar to the top reinforcement strut, the lower feature may be comprised of a material with enough stiffness to give the valve frame additional structural strength, while being flexible enough to allow the lower reinforcement strut to expand and/or straighten out or unfold.

The lower reinforcement strut may be flared beyond the cylindrical plane of the valve frame opening to allow for device fixation to native heart structures or may be used as a fixation method for a valve-in-stent transcatheter deployment or valve-in-valve transcatheter deployment, among other applications.

In other embodiments, the lower reinforcement strut may have a variety of different geometries that may be varied according to the application of the valve replacement device. For example, the top reinforcing feature may be diamond shaped to more readily allow the valve to be compressed over a catheter for percutaneous transvenous or transarterial valve deployment. Other shapes are also contemplated, and the current disclosure is not so limited.

The top and lower reinforcement struts, or any other reinforcement strut, may also be tuned to alter or control the shape of the valve as the valve expands. The material properties, geometry, thickness of the reinforcement struts, etc., may be modified to achieve a specific opening geometry with expansion. The reinforcement struts may also differ in material, geometry, or thickness to achieve a specific opening geometry with expansion. One reinforcement strut may even differ in material or thickness within said reinforcement strut to achieve a specific opening geometry with expansion. In some embodiments, it is contemplated that the reinforcement struts could control the expansion of the frame to cause the opening to be elliptical in shape, or asymmetrically shaped, or circular in shape. Other shapes are contemplated as well. For example, a reinforcement strut may be materially thicker on one side, or shorter on one side, or be made of a stiffer material on one side to ensure that that side does not expand to the same degree as the other side of the frame.

While top and lower reinforcement features are described, it should be understood that some embodiments can include one of or both of the top and lower reinforcement features. Additionally, some embodiments may include additional features that connect the frame sections and may be located between the top and lower reinforcement features.

In some embodiments, the valve replacement device may include a plurality of holes spaced along the frame. The holes may act as anchor points for sutures to assist in the attachment of the leaflets to the frame. In some embodiments, the leaflets have additional protruding segments of material that is affixed to the frame via interspersing slots along the length of the leaflet attachment line, and then mechanically fixed on the outside of the frame.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1A shows one embodiment of the valve replacement implanted within a representative vessel. Valve replacement device 100 comprises a frame 102 and an outer frame support 108. Frame 102 may be symmetrical, with two frame sections 104 that converge at commissural posts 110. The frame sections may each be U-shaped arcs. Lining the arc of each frame section 104 is a leaflet 106. The leaflets

106 hang off of frame sections 104 such that in the device's closed configuration, the leaflets hang down and coapt, obstructing the device opening. As blood flows through the vessel (flowing upwards from the bottom as viewed in FIG. 1A), the flow of blood pushes the leaflets apart, exposing the opening and placing the leaflets in an open configuration. As blood flow begins to slow, the leaflets once again collapse to the closed configuration, preventing regurgitation of blood. As can be seen in FIG. 1B, as the vessel around the device grows, the device similarly expands with the vessel to continue effectively serving as a replacement valve.

Figure 2:
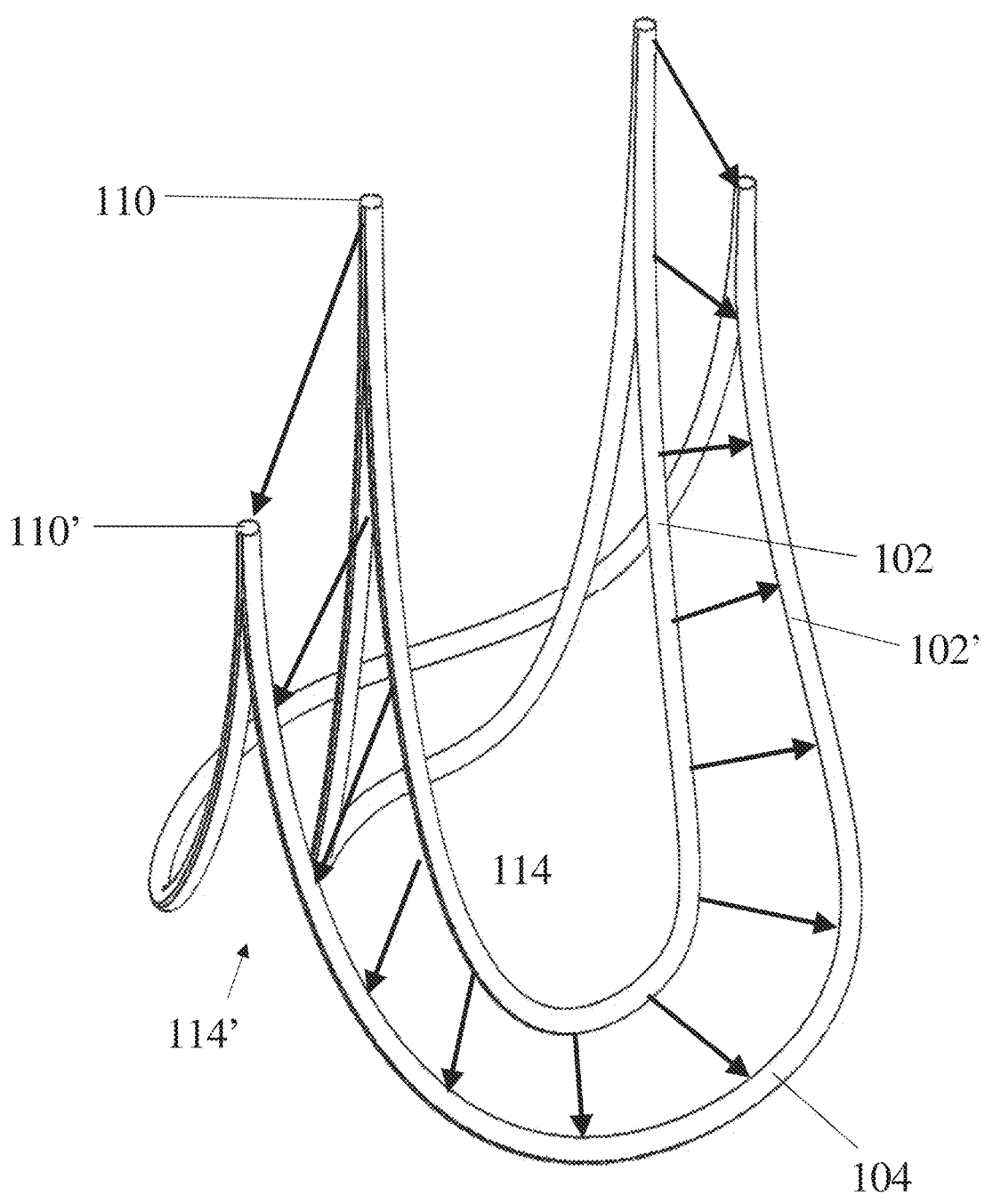
FIG. 2 is a perspective view of the frame of the valve replacement device of FIG. 1A over the course of expansion.
Figures 3, 4:
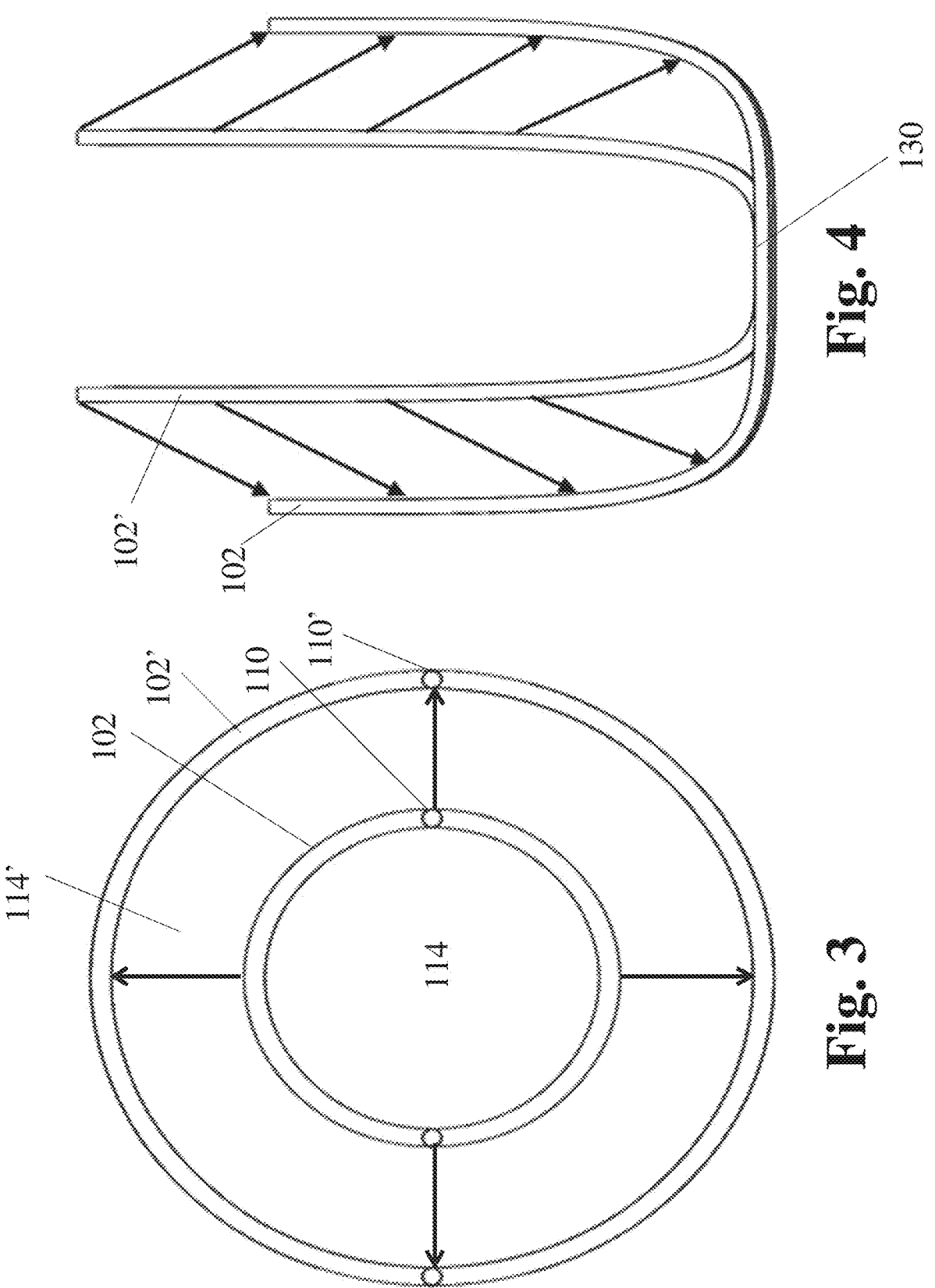
FIG. 3 is a top view of the frame of the valve replacement device of FIG. 1A over the course of expansion.
FIG. 4 is a front view of the frame of the valve replacement device of FIG. 1A over the course of expansion.

FIGS. 2, 3, and 4 show different perspectives of one embodiment of the frame as it expands. Frame 102 shows the frame initially, while 102' shows the frame after some expansion. As best seen in FIGS. 2 and 3, the opening of the frame expands from a pre-expansion opening 114 to a larger expanded opening 114' Similarly, commissural posts 110 shows the posts prior to expansion, and 110' shows the posts after some expansion. The frame may have a vertical height (axial length) of between 5 mm-50 mm, and an internal diameter of 5 mm-50 mm at its baseline prior to expansion.

In some embodiments, the frame may have a height to diameter ratio of about 0.5:1 to 2.5:1, or 0.6:1 to 2.4:1, or 0.7:1 to 2.3:1, or 0.8:1 to 2.2:1, or 0.9:1 to 2.1:1, or 1:0 to 2:1, or 1.1:2.0, or 1.2:1 to 1.9:1, or 1.3:1 to 1.9:1, or 1.3:1 to 1.8:1, or 1.4:1 to 1.7:1, or 1.5:1 to 1.8:1, or 1.6:1 to 1.7:1, or 0.6:1 to 2.5:1, or 0.7:1 to 2.5:1, or 0.8:1 to 2.5:1, or 0.9:1 to 2.5:1, or 1.0:1 to 2.5:1, or 1.1:1 to 2.5:1, or 1.2:1 to 2.5:1, or 1.3:1 to 2.5:1, or 1.4:1 to 2.5:1, or 1.5:1 to 2.5:1, or 1.6:1 to 2.5:1, or 1.7:1 to 2.5:1.

Figure 5A:
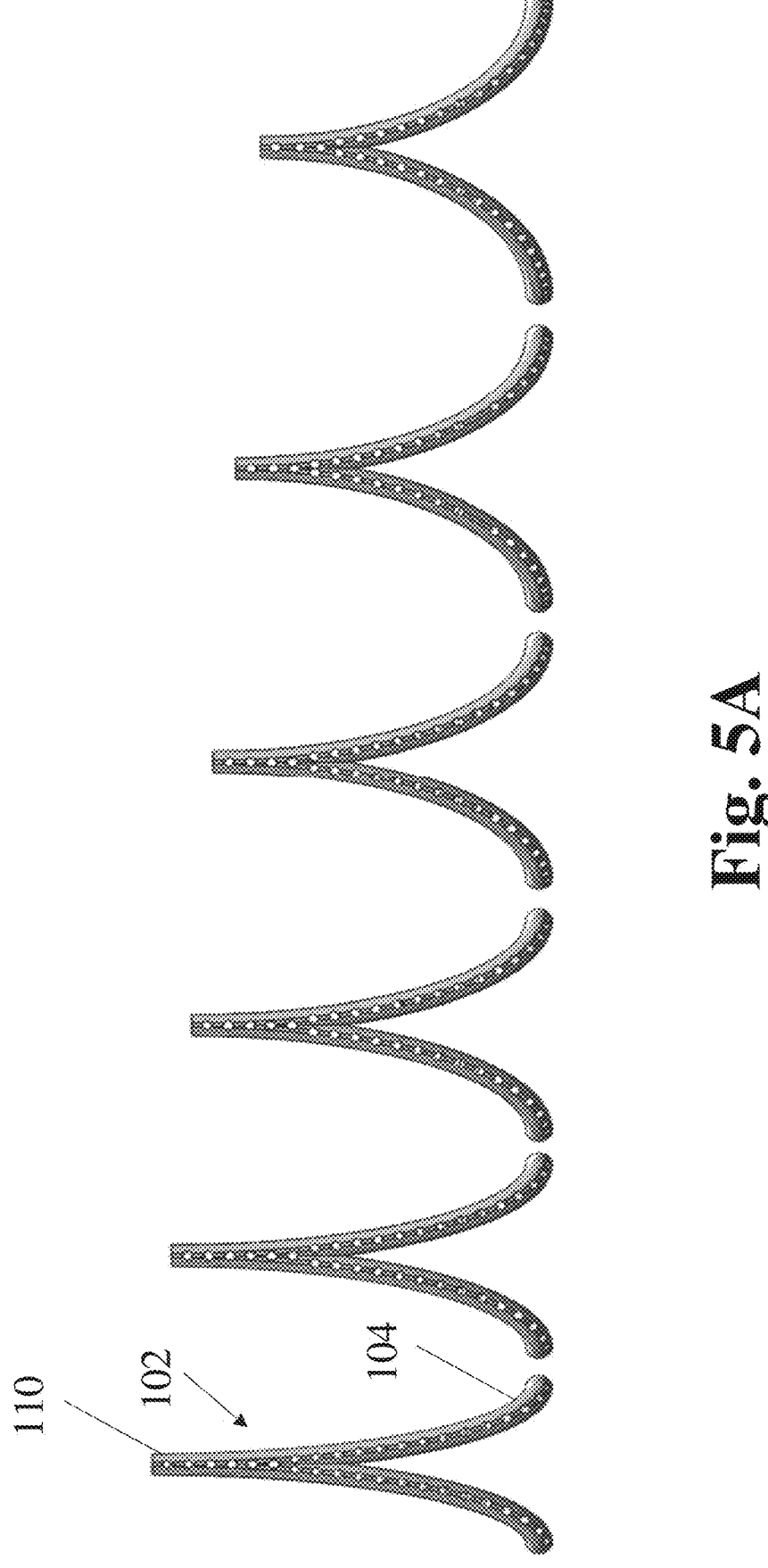
FIG. 5A is a side view of the frame of the valve replacement device of FIG. 1A during increasing stages of expansion from left to right.
Figure 5B:
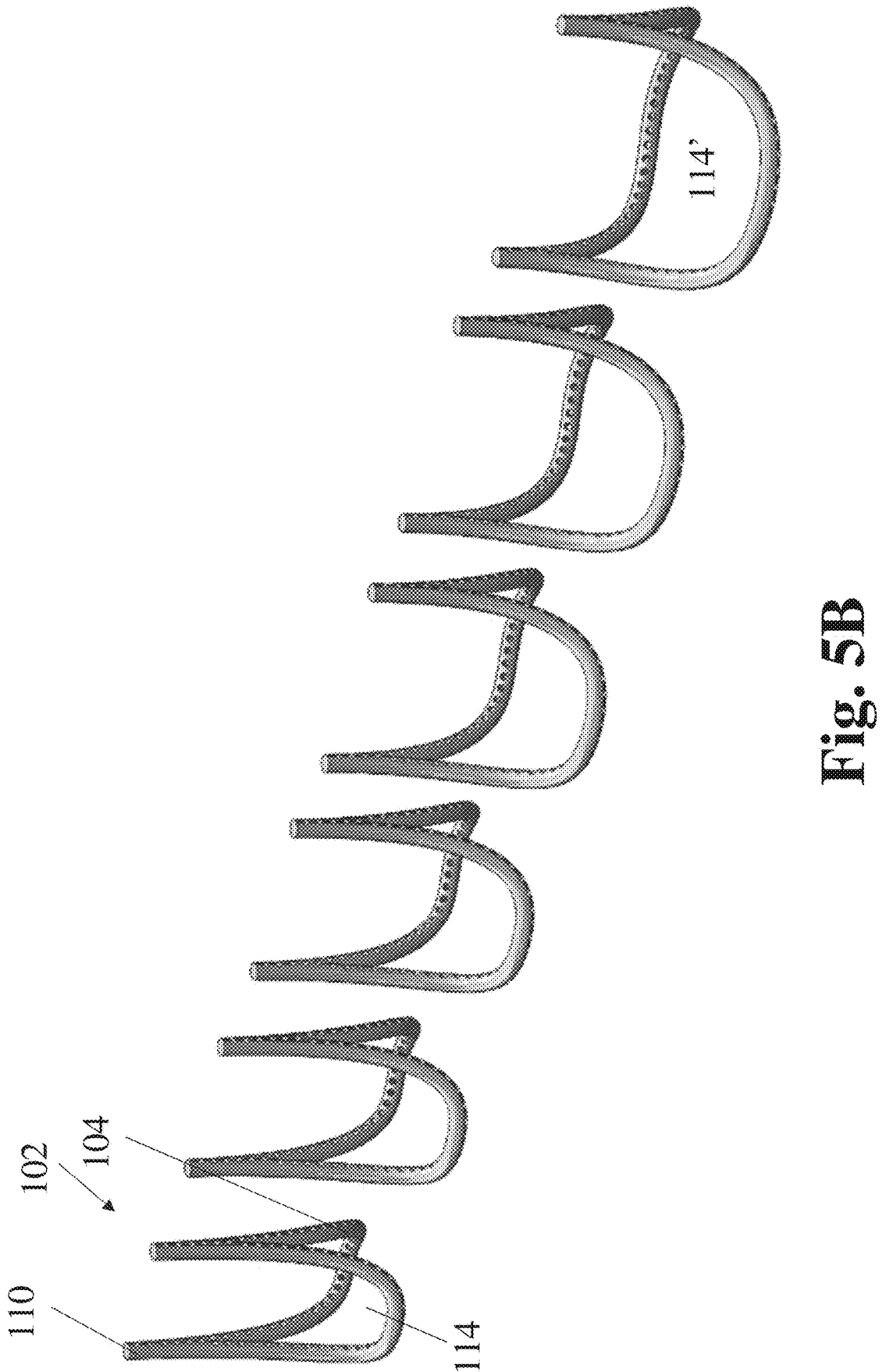
FIG. 5B is a perspective view of the frame of the valve replacement device of FIG. 1A during increasing stages of expansion from left to right.
Figures 6A, 6B:
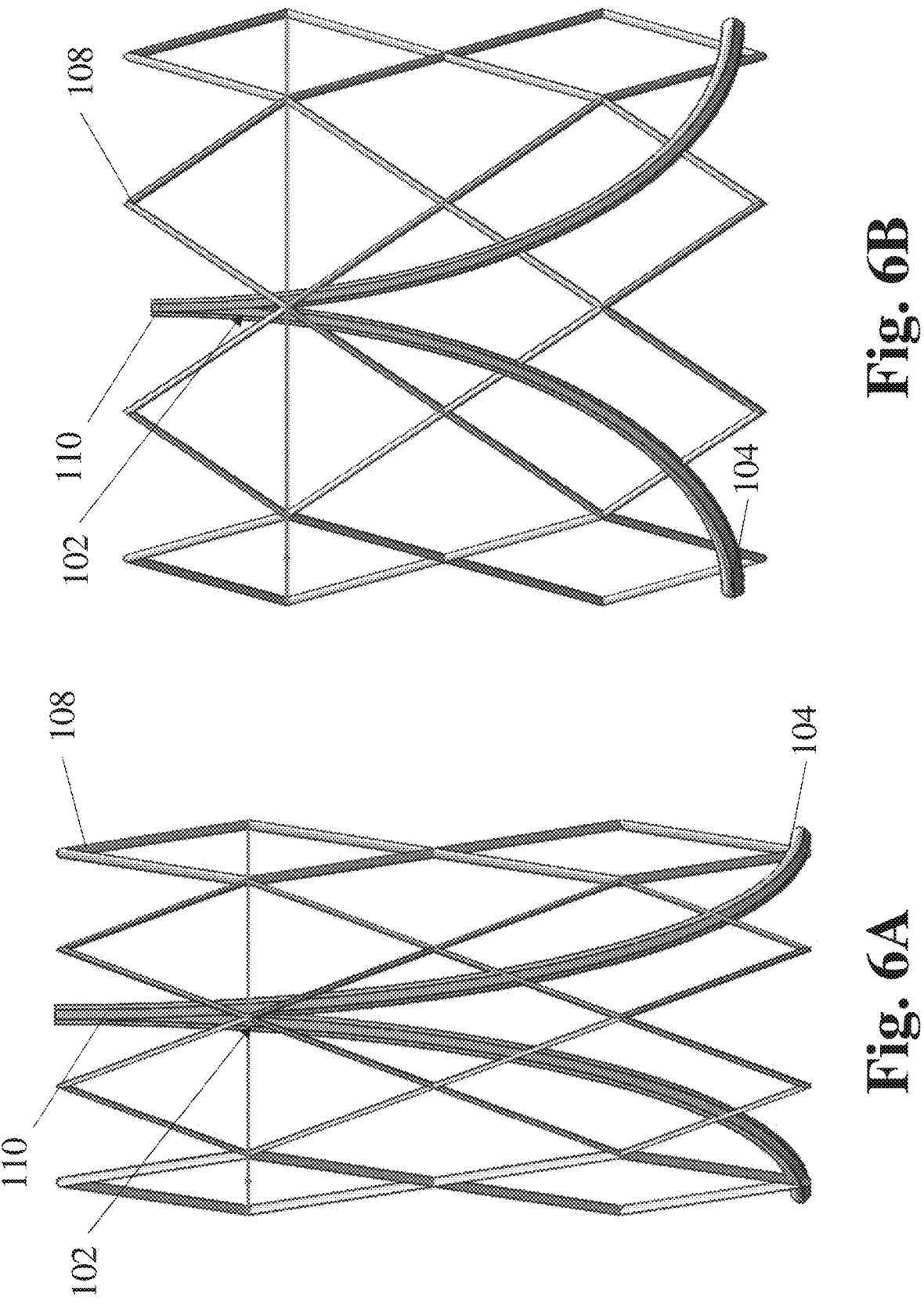
FIG. 6A is a side view of the frame and outer frame support of the valve replacement device prior to expansion.
FIG. 6B is a side view of the frame and outer frame support of the valve replacement device after some expansion.
Figures 7A, 7B:
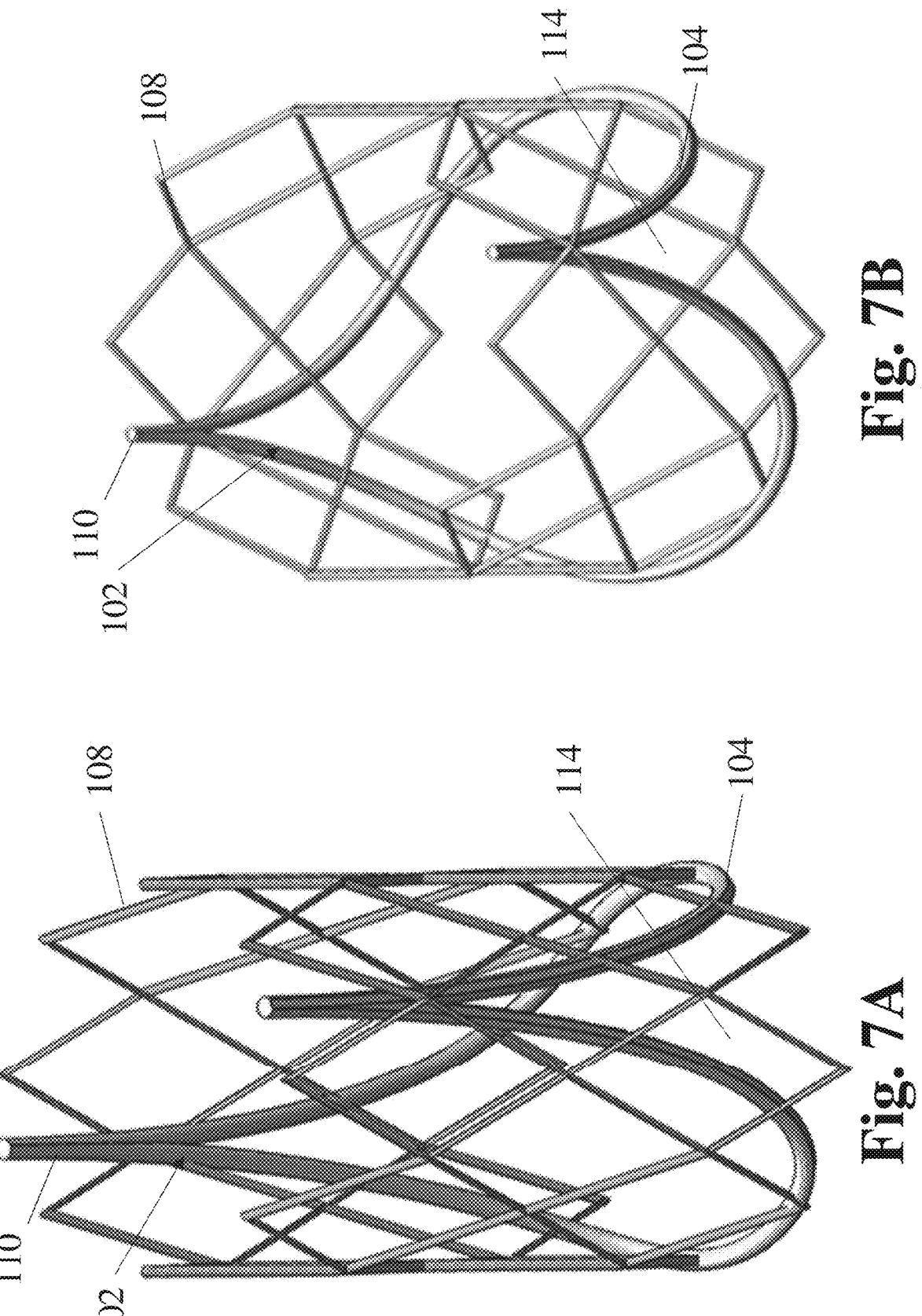
FIG. 7A is a top perspective view of the frame and outer frame support of FIG. 6A prior to expansion.
FIG. 7B is a top perspective view of the frame and outer frame support of FIG. 6A after some expansion.

As the frame expands, the two frame sections 104 move laterally away from each other. As the frame sections 104 move away from each other, the commissural posts 110 decrease in height. FIGS. 5A and 5B show a time lapse of the frame expanding from a small diameter configuration (left) to a large diameter configuration (right). As can be seen from FIGS. 3 and 4, in some embodiments, as the frame expands, it may expand evenly in all radial directions. In some embodiments, the spreading mechanism of the frame sections 104 that occurs during growth to expand the overall frame 102 may preserve the perimeter length of each frame section 104. As seen in FIG. 5B, the pre-expansion opening 114 expands to a larger expanded opening 114' as the frame expands.

The frame may be made of nitinol, titanium, cobalt chromium alloy, stainless steel, a biodegradable polymer, a bioresorbable polymer, a synthetic material, platinum iridium, a magnesium or iron alloy, and/or any other suitable material.

In some embodiments, each leaflet 106 may have a ¾ to ½ moon shape so that the concaved-out side matches the arc of the frame sections 104 that the leaflet is attached to. The leaflet 106 may be sutured, adhered, or otherwise attached to a frame section. The concave-in side or the free edge 115 (see FIGS. 1A, 1B for an illustrative example of a free edge) of the leaflet may have a length of up to 4 times the diameter of valve in baseline state/configuration, while the leaflet vertical height may be up to 2.5 times the diameter of valve in baseline state/configuration. The height of the center of the leaflet can range from 0.2 to 0.8 times the height of the leaflet at the commissural posts. As the frame expands, the leaflet-commissure attachment angle increases, resulting in straightening of the leaflet's free edge 115. The excess leaflet height ensures that there is sufficient coaptation for the device to function effectively as a valve across the full range of the device's expansion. The coaptation height can be up to three quarters of the opening diameter prior to valve frame expansion. While the depicted embodiments show equally sized and shaped leaflets that are symmetric to one another, the valve leaflets may be different in size and/or shape from one another. In some embodiments, one larger leaflet may cover the majority of the valve opening in the closed position, with one or more smaller leaflets forming a crescent-like shape in the closed position.

While dimensions for the leaflets are provided above, it should be understood that other sizes are also contemplated. For example, the free edge of the leaflet may have a length of between 2 to 6 times or some other range. The leaflet vertical heights may be between 1.5 to 3.5 times the diameter of the valve in the baseline configuration or 2.2 to 2.7 times. The mid-height of the valve may be from 0.1 to 1 times the height of the leaflet at the commissural posts. Other ranges are further contemplated.

While the depicted embodiments show designs utilizing two leaflets, designs using three or more leaflets with two or more frame sections are also contemplated. Designs using a single leaflet are also contemplated.

The leaflets can be made of a bioabsorbable polymer, a synthetic polymer, a tissue-engineered construct, a decellularized homologous tissue engineered leaflet, a thin film nitinol, an expanded PTFE membrane, a gluteraldehyde-treated bovine pericardium, a gluteraldehyde-treated porcine pericardium, a photo-oxidized bovine pericardium, a bovine jugular vein valve, or any other suitable composition or material. In some embodiments, the leaflets are made of 0.1 mm thickness expanded PTFE membrane (GORE PRE-CLUDE Pericardial Membrane) having a Young's modulus of around 60 MPa at physiological loads. Young's modulus ranges from 30 MPa to 4 GPa, or 70 MPa to 4 GPa, or 100 MPa to 4 GPa, or 200 MPa to 4 GPa, or 500 MPa to 4 GPa for the leaflet material are also contemplated.

FIGS. 6A, 6B, 7A, and 7B show views of the frame and the outer frame support at different stages of expansion according to one embodiment of the device. The outer frame support 108 in this embodiment is a mesh cylinder with open cells. As shown in FIGS. 1A and 1B, the outer frame support may provide stability for the device and maintain the orientation of the frame relative to the vessel 112. As the frame 102 expands, the mesh tube comprising outer frame support 108 may expand as well, reducing the height of the outer frame support while increasing its diameter to match the diameter of the vessel.

While the depicted embodiment shows the outer frame support in the form of a mesh cylinder with open cells, it should be understood that the outer frame support may take different forms as well. The outer frame support may have closed cells or may have mixed open and closed cells. The outer frame support may also comprise a partially solid cylinder with expandable segments, or any other arrangement that would allow the outer frame support to expand with the frame.

In some embodiments, the valve replacement device may include an outer flexible covering that may wrap around the outer frame support, or, in the absence of a separate outer frame support, may wrap around the frame itself. The flexible covering may prevent tissue ingrowth into the outer frame support, as well as the formation of abnormal layers of fibrovascular or granulation tissue. The frame and the flexible covering may be chemically inert, or they could be treated with compounds to imbue desirable properties including but not limited to anti-adhesive properties, or anti-thrombogenic properties.

Figure 8:
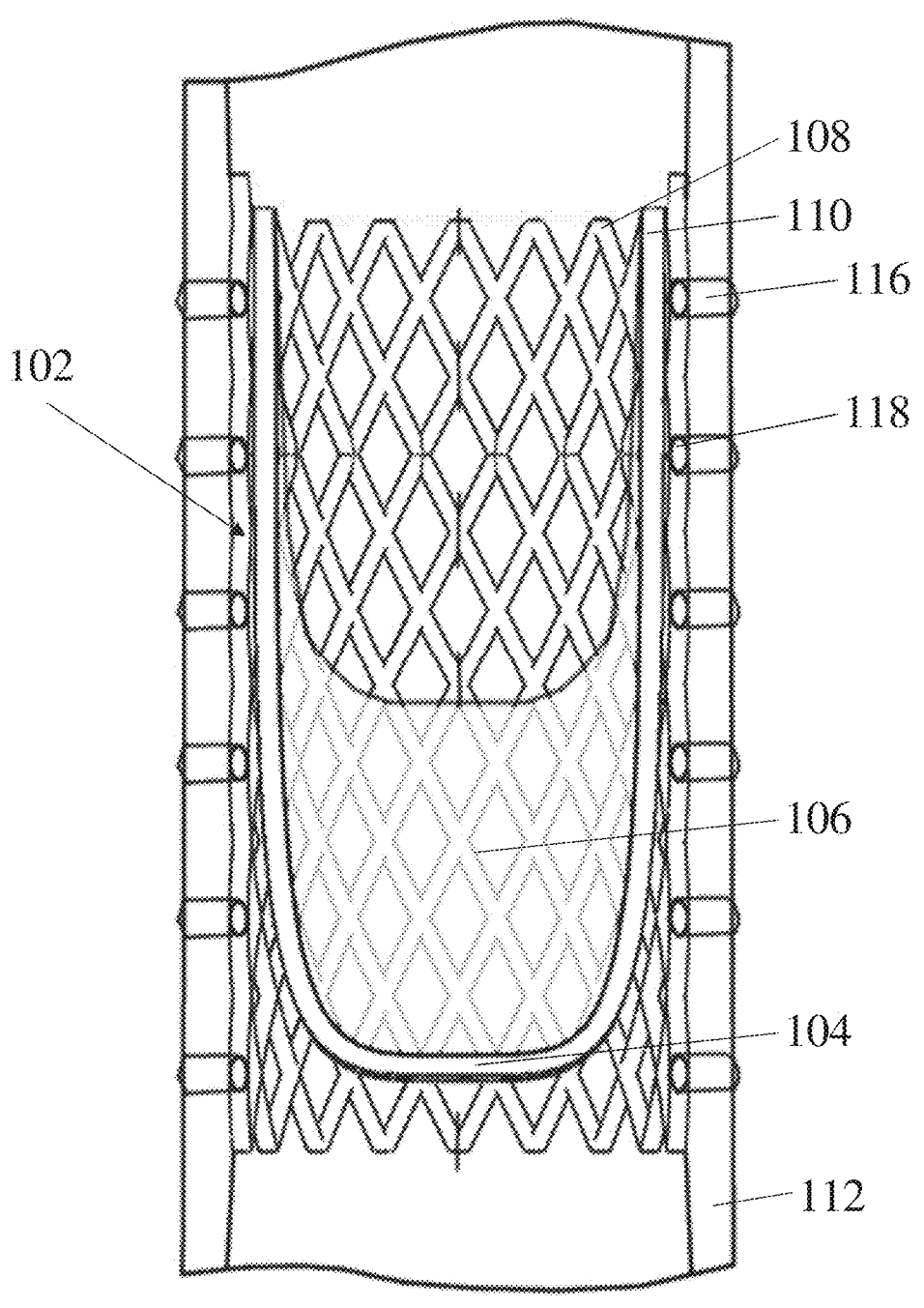
FIG. 8 is a cross-sectional view of one embodiment of the valve replacement device implanted in a vessel according to one embodiment.

FIG. 8 shows one embodiment of the valve replacement device implanted in a vessel 112. In this embodiment, the outer frame support 108 is secured to the vessel 112 by a series of sutures 118 spaced along the length of the outer frame support 108. The sutures 118 fix the outer frame support to the vessel such that as the vessel grows, the vessel provides a radially outward force on the outer frame support that causes the outer frame support to expand, in turn causing the expansion of frame 102. In some embodiments, the outer frame support may include a plurality of holes 116 to receive such sutures.

Figure 9:
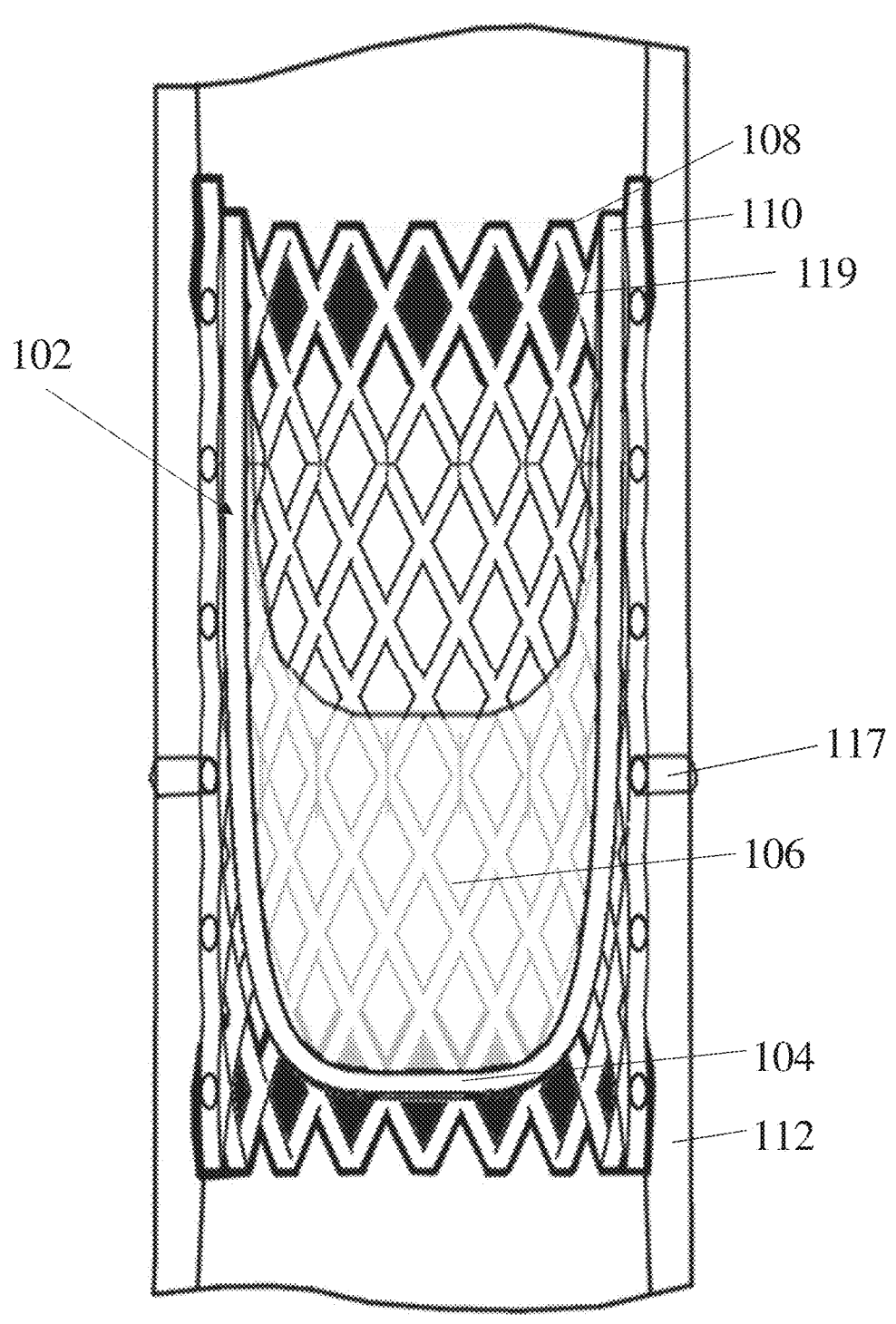
FIG. 9 is a cross-sectional view of one embodiment of the valve replacement device implanted in a vessel according to another embodiment.

In some embodiments, the outer frame support may be secured to the vasculature at only a single attachment location. For example, the outer frame support may be secured to the vasculature at only a single attachment line along the height of the device. In the embodiment shown in FIG. 9, the outer frame support 108 is secured along a single line 117 to the vessel 112. Having a single attachment location between the vasculature and the device may help permit changes in height and diameter of the device, as well as accommodate axial growth of the vasculature. In some embodiments, the device may also include proximal and distal seals 119 at either axial end of the device. The proximal and distal seals 119 may prevent paravalvular leak, stasis of blood flow, or otherwise aberrant blood flow profiles. In some embodiments the valve may have an outer covering made of expandable synthetic material that extends beyond the base of the valve. The material may be used as a sewing ring to fix the valve in the position of the native valve annulus. This may be the only site of device attachment.

Figure 10:
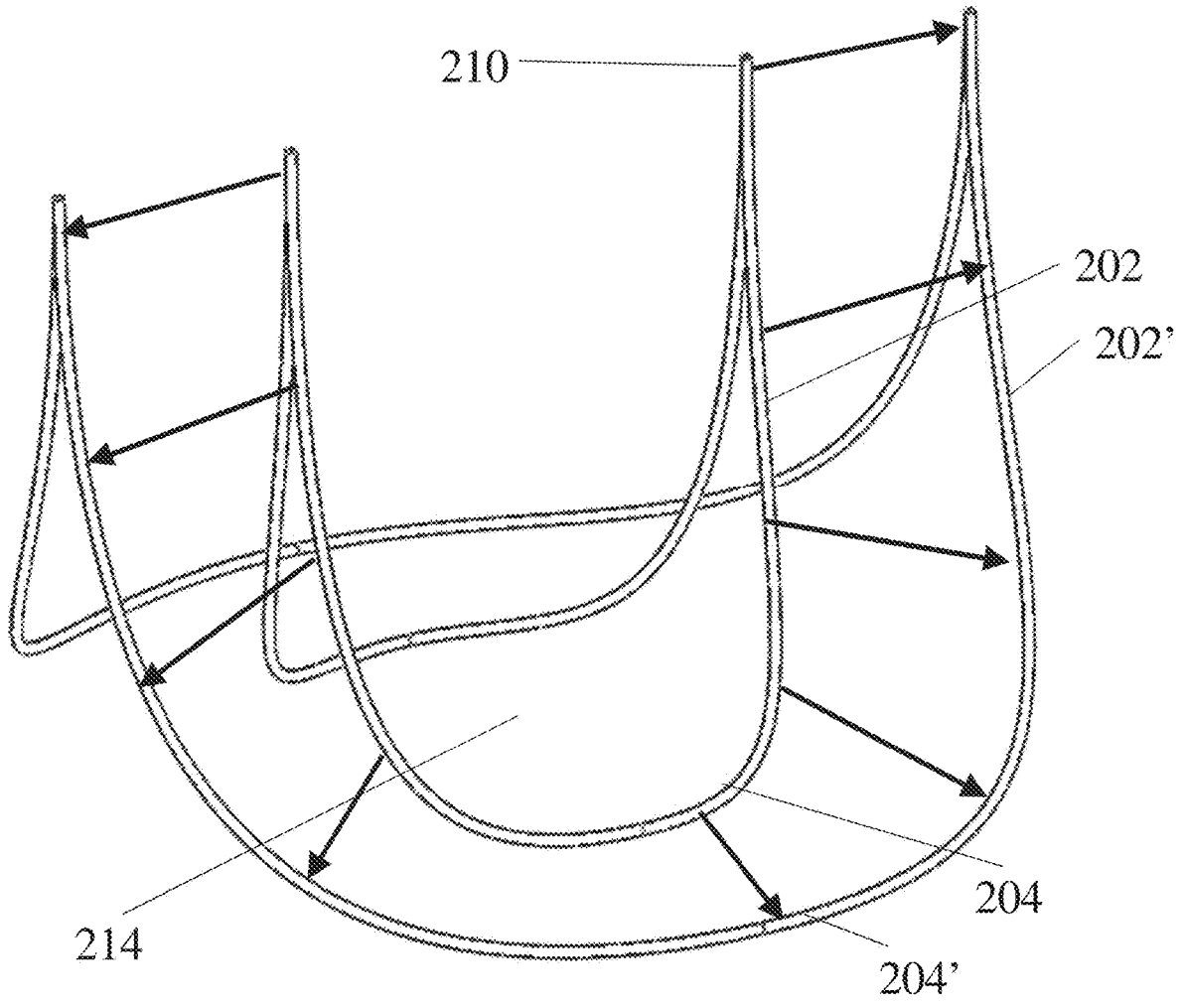
FIG. 10 is a perspective view of one embodiment of the frame of the growth-accommodating valve replacement device over the course of expansion.
Figures 11A, 11B:
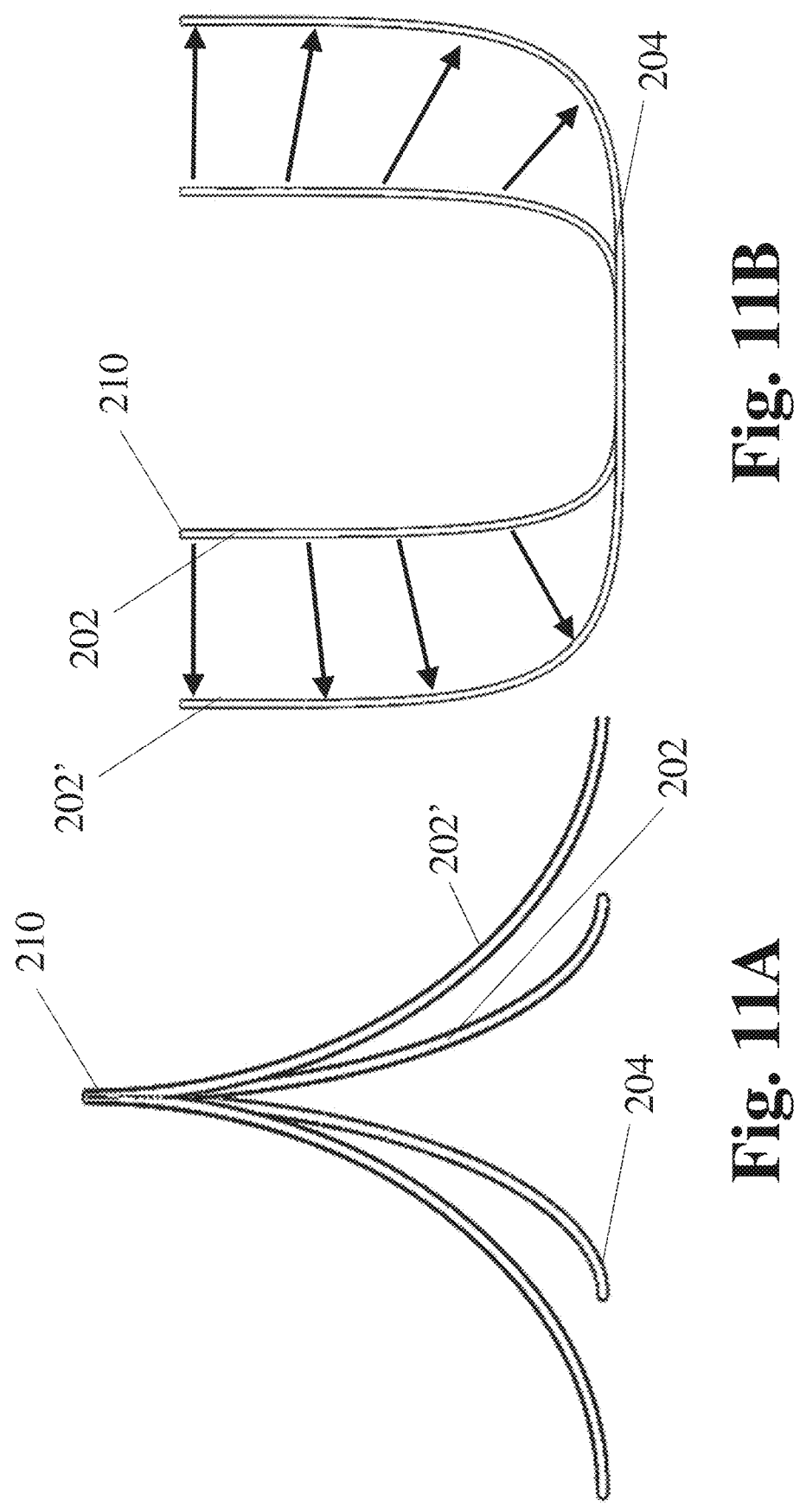
FIG. 11A is a side view of the frame of FIG. 10 over the course of expansion.
FIG. 11B is a front view of the frame of FIG. 10 over the course of expansion.
Figure 12:
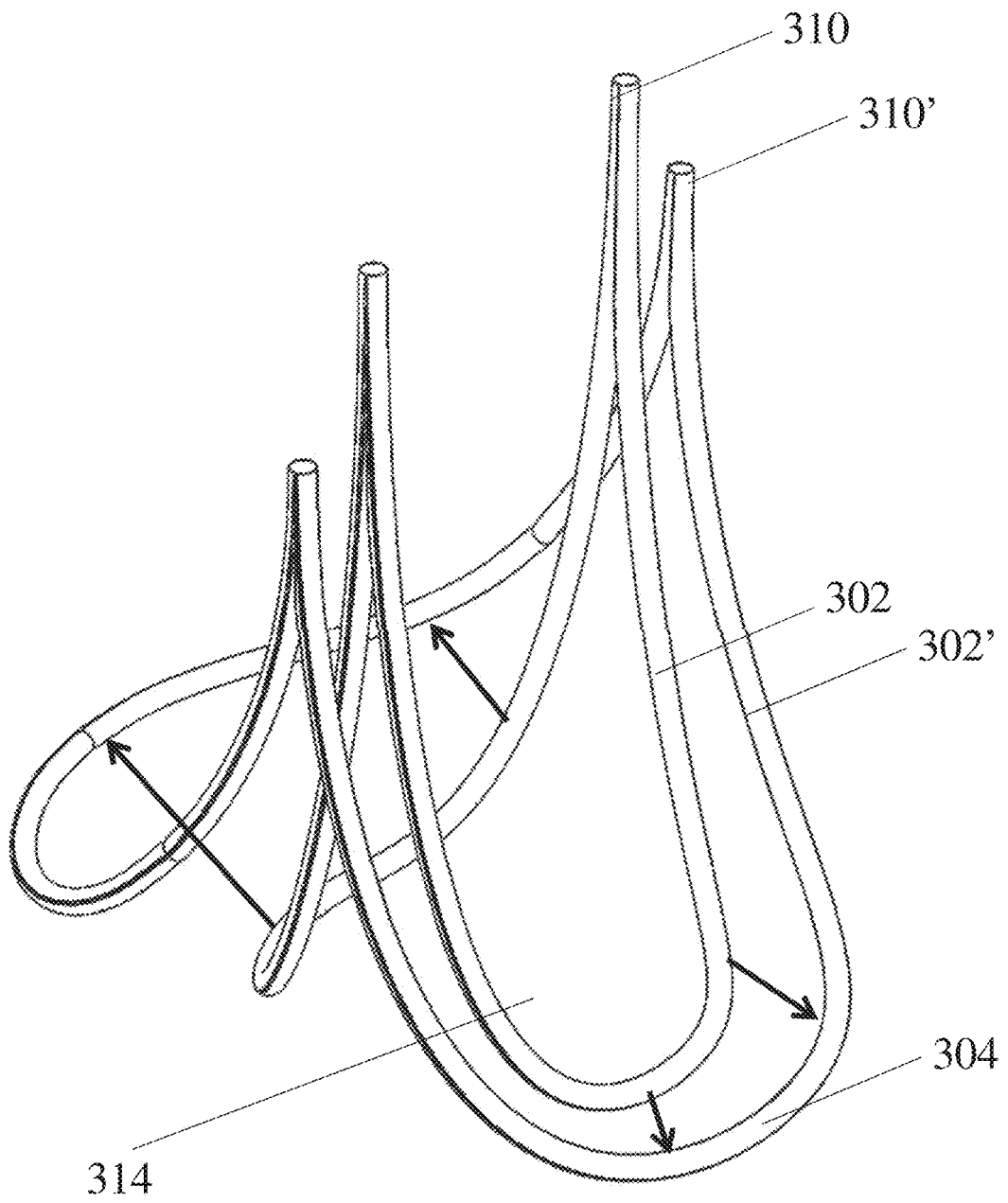
FIG. 12 is a perspective view of another embodiment of the frame of the valve replacement device over the course of expansion.
Figure 13A:
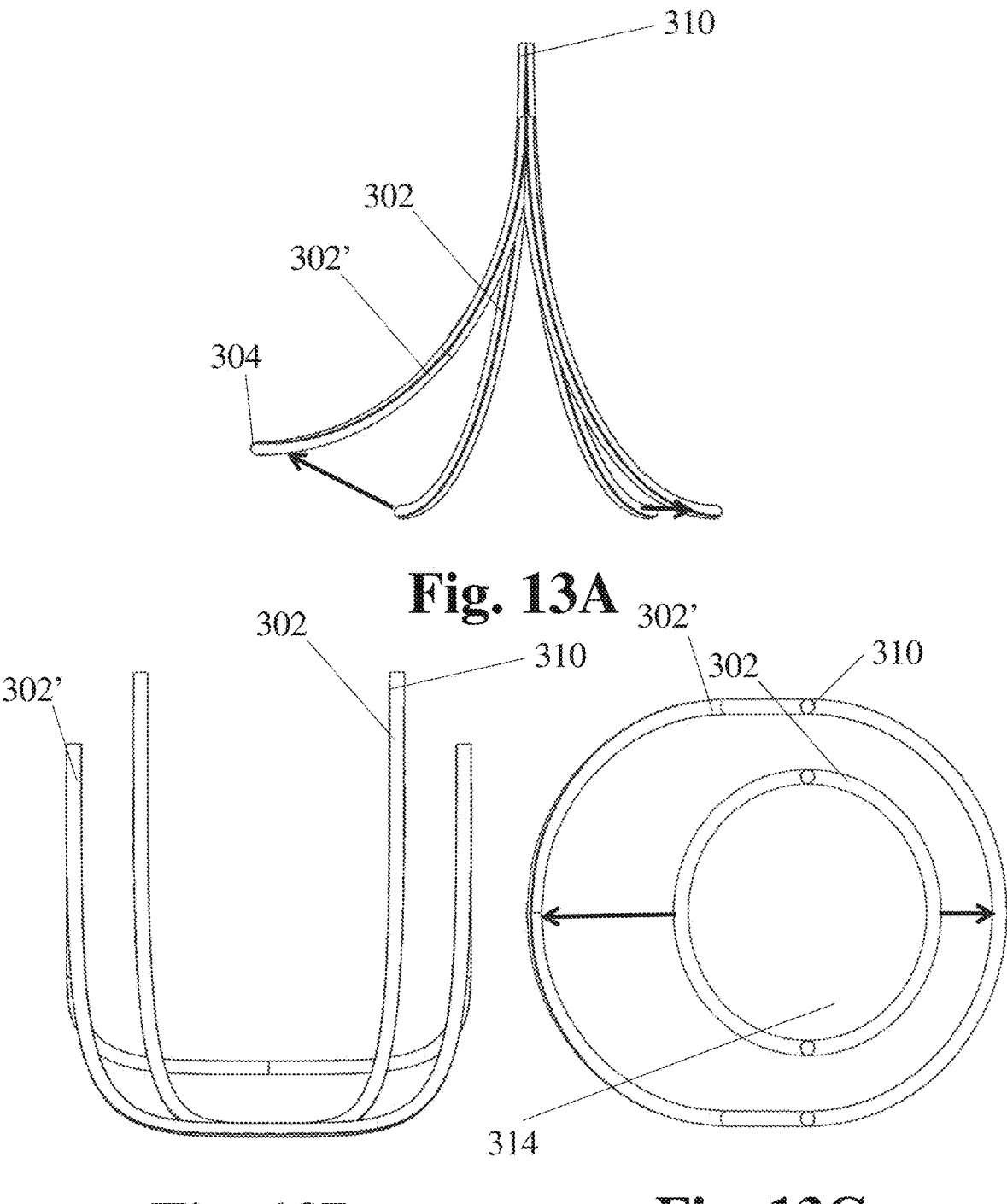
FIG. 13A is a side view of the frame of FIG. 12 undergoing some expansion.

FIGS. 10, 11A, and 11B show another embodiment of the frame. In this embodiment, as the frame 202 expands, the frame sections 204 lengthen and separate from each other to increase the size of opening 214, 202' shows frame 202 after some expansion. Frame section 204 represents the location and shape of the frame section prior to expansion and 204' represents the location and shape of the frame section after some expansion. In some embodiments, the height of commissural posts 210 and the height of entire frame overall is maintained as the opening diameter increases.

For devices having elongating frame perimeter lengths, in some embodiments, the leaflets are configured to increase in size as the opening diameter increases. For example, in some embodiments, the leaflets may be sutured to the frame sections with extra material folding up like an accordion between sutures. As the frame sections expand, the distance between the sutures expand, unfolding the accordion like folds, providing additional sections of leaflet to accommodate the lengthening. In other embodiments, the leaflets are sutured normally to the frame sections, but the leaflets are particularly flexible or distensible and simply stretch as the frame sections expand.

While the depicted embodiments depict a symmetrical valve frame having a circular opening and frame sections that expand evenly, it should be understood that the current disclosure is not limited as such. In other embodiments of the device, the opening may be elliptical or otherwise irregular in shape to accommodate different structural environments and physiological valve applications.

FIGS. 12, 13A, 13B, and 13C show an embodiment of the frame where the two frame sections expand asymmetrically. Frame 302 begins with commissural posts 310 at one height, then after expansion, frame 302' has commissural posts 310' at a reduced height due to expansion. In these embodiments, the commissural posts 310 or the frame sections 304 may be unequal in some way to produce asymmetric expansion. They may be flared inwards between or equal to 5 degrees to 45 degrees, flared outwards between or equal to 45 degrees, could be of unequal heights prior to valve frame expansion, could have different thicknesses, or could be comprised of materials with differing stiffnesses. Regardless, when the frame 302 attempts to expand with the vasculature, the two frame sections separate laterally at different rates, creating an elliptical opening 314.

Figures 14A, 14B, 14C, 14D:
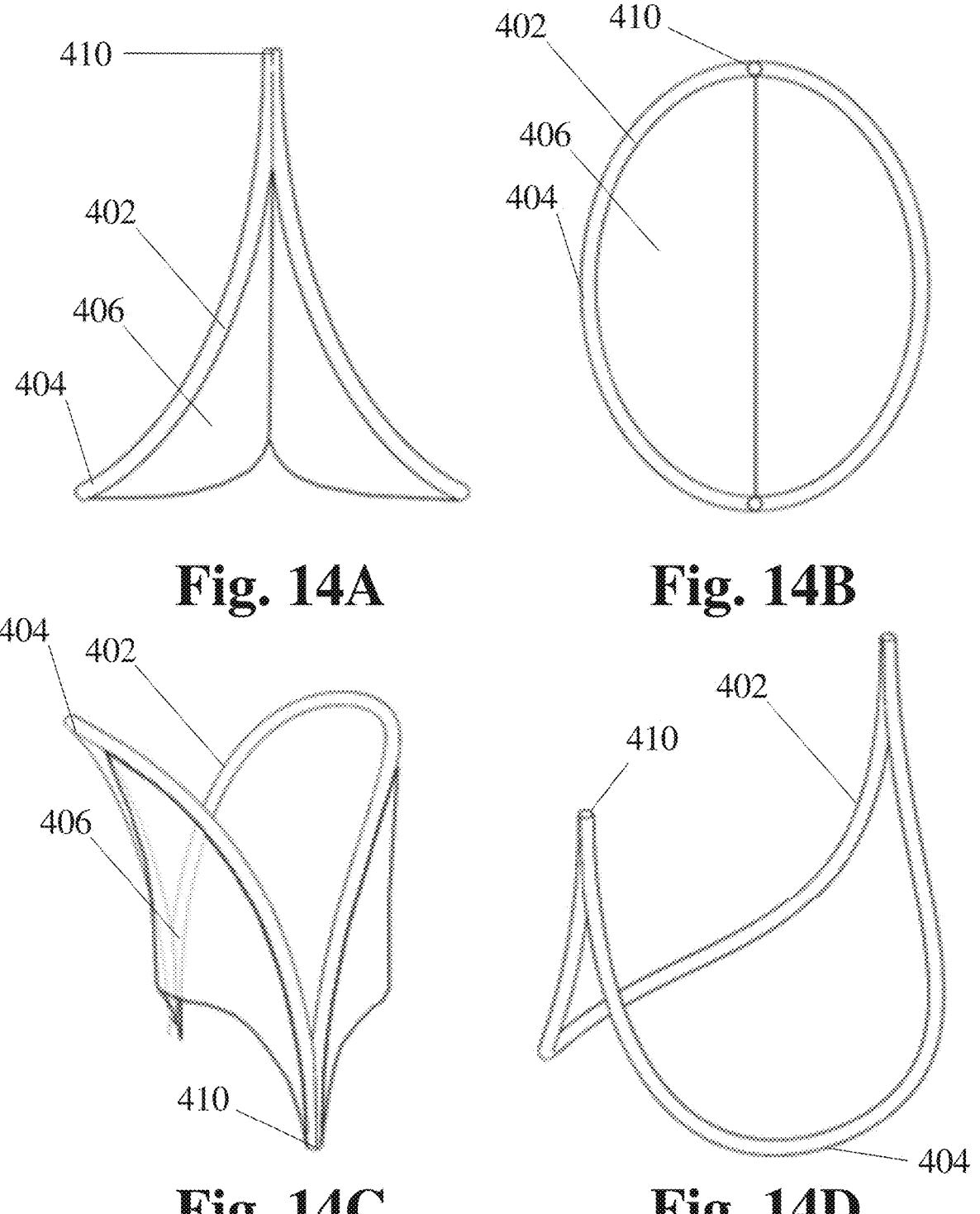
FIG. 14A is a side view of another embodiment of the frame and leaflets of the valve replacement device.
FIG. 14B is a top view of the frame and leaflets of FIG. 14A.
FIG. 14C is an inverted perspective view of the frame and leaflets of FIG. 14A.
FIG. 14D is a perspective view of the frame of FIG. 14A.

FIGS. 14A to 14D show an embodiment of the frame 402 and leaflets 406 defining an elliptical opening. In this embodiment, frame sections 404 are wider than in previous embodiments to produce an elliptical shape from the top view as seen in FIG. 14B. Commissural posts 410 are located at opposite sides along the major axis of the ellipse formed by the opening of the device. As the frame sections diverge, the opening of the device may remain coplanar with the perpendicular cross-section of the surrounding vasculature. While the figure shows commissural posts of equal heights, in some embodiments, the commissural posts may have unequal heights, or could be flared inwards or outwards 5-45 degrees. In some embodiments, the valve replacement device may be used as an inflow valve. In some embodiments, the valve replacement device may mimic the shape of a native atrioventricular valve.

Figures 15A, 15B, 15C, 15D, 15E:
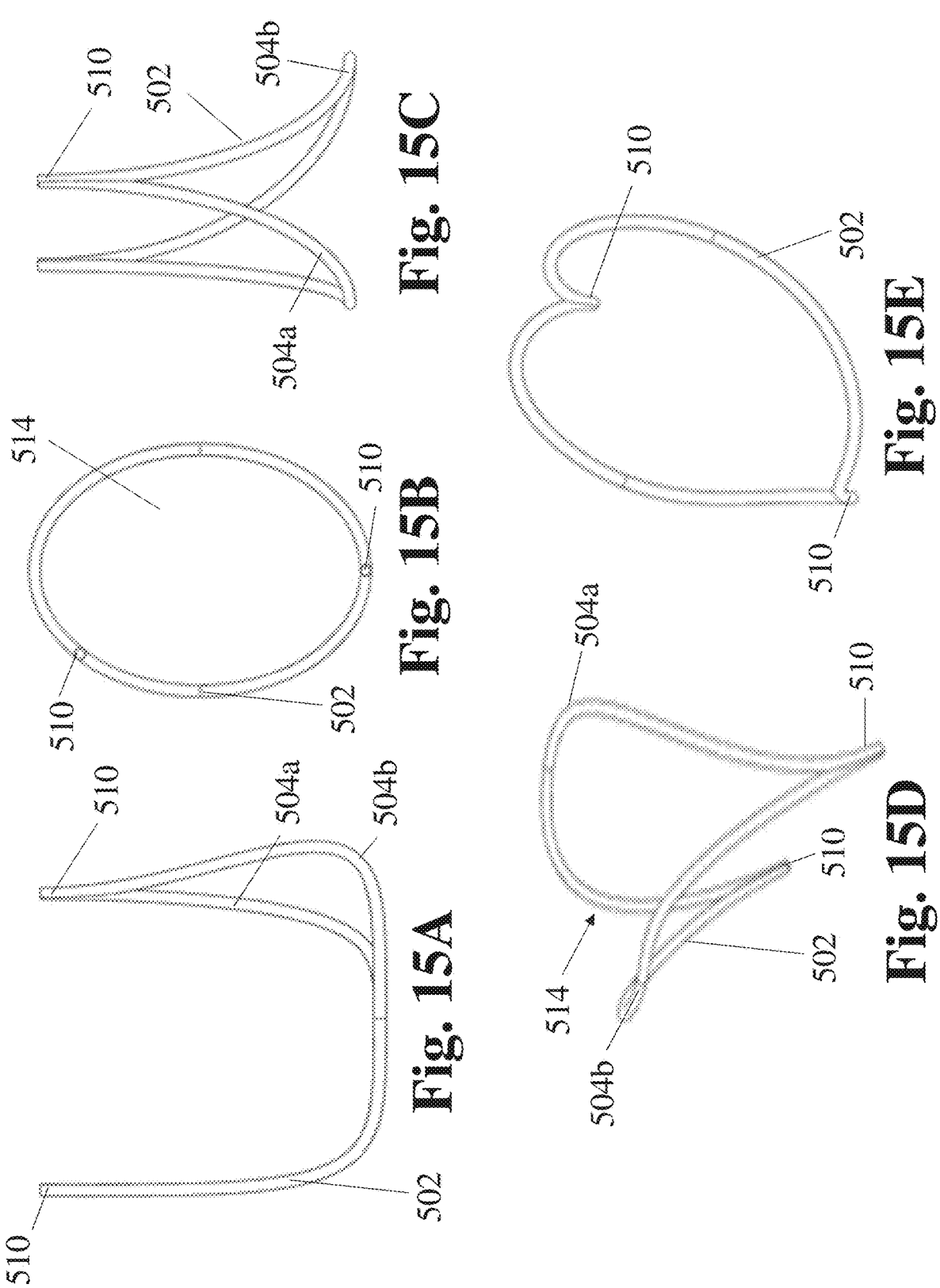
FIG. 15A is a front view of another embodiment of the frame of the valve replacement device.
FIG. 15B is a top view of the frame of FIG. 15A.
FIG. 15C is a side view of the frame of FIG. 15A.
FIG. 15D is a perspective view of the frame of FIG. 15A.
FIG. 15E is a bottom perspective view of the frame of FIG. 15A.

FIGS. 15A to 15E show another embodiment of the frame 502 that defines an elliptical opening 514. In this embodiment, frame sections 504a and 504b are differently sized and or shaped from one another prior to valve frame expansion. As seen in FIG. 15B, only one of the commissural posts 510 are located on the major axis of the ellipse formed by the opening, while the other commissural post is located anterior to the major axis. Due to the different size and/or shape of the valve frame sections relative to one another, the leaflets of this embodiment are similarly different from one another to match their respective frame sections. In some embodiments, the leaflets could have the same mechanical properties as one another or could have different mechanical properties than one another to suit different applications. For example, the larger leaflet could be more extensible compared to the smaller leaflet to account for the size difference. In other embodiments, the commissural posts tilt axially relative to the surrounding vasculature. Embodiments with the tilted commissural posts can accommodate curved flow patterns through the device and enable preserved valve function in a variety of structural environments depending on the degree of the tilt. This tilting may give rise to an opening that does not sit in the same plane as the perpendicular cross-section of the lumen of the local vasculature.

FIGS. 16A to 16D show another embodiment of the frame 602 having frame sections 604. This embodiment has an asymmetric frame 602 that defines an elliptical opening 614. However, in this embodiment, both commissural posts 610 are located anterior to the major axis of the ellipse seen in FIG. 16C. Due to this arrangement, the frame 602 is asymmetric, resulting in one leaflet covering the majority of the opening.

In some embodiments, the plane formed by the opening could be orthogonal to the flow of fluid in the surrounding vasculature or could be offset relative to the flow of fluid. In some embodiments, the plane formed by the opening may be coplanar with the perpendicular cross-section of the surrounding vasculature, or may be tilted relative to this perpendicular cross-section. For example, in the embodiment shown in FIG. 1A, the plane formed by the opening 114 of the device is coplanar with the perpendicular cross-section of the surrounding vasculature, which is vessel 112. In addition, the plane formed by the opening 114 is also orthogonal to the flow of fluid through vessel 112.

Figure 17:
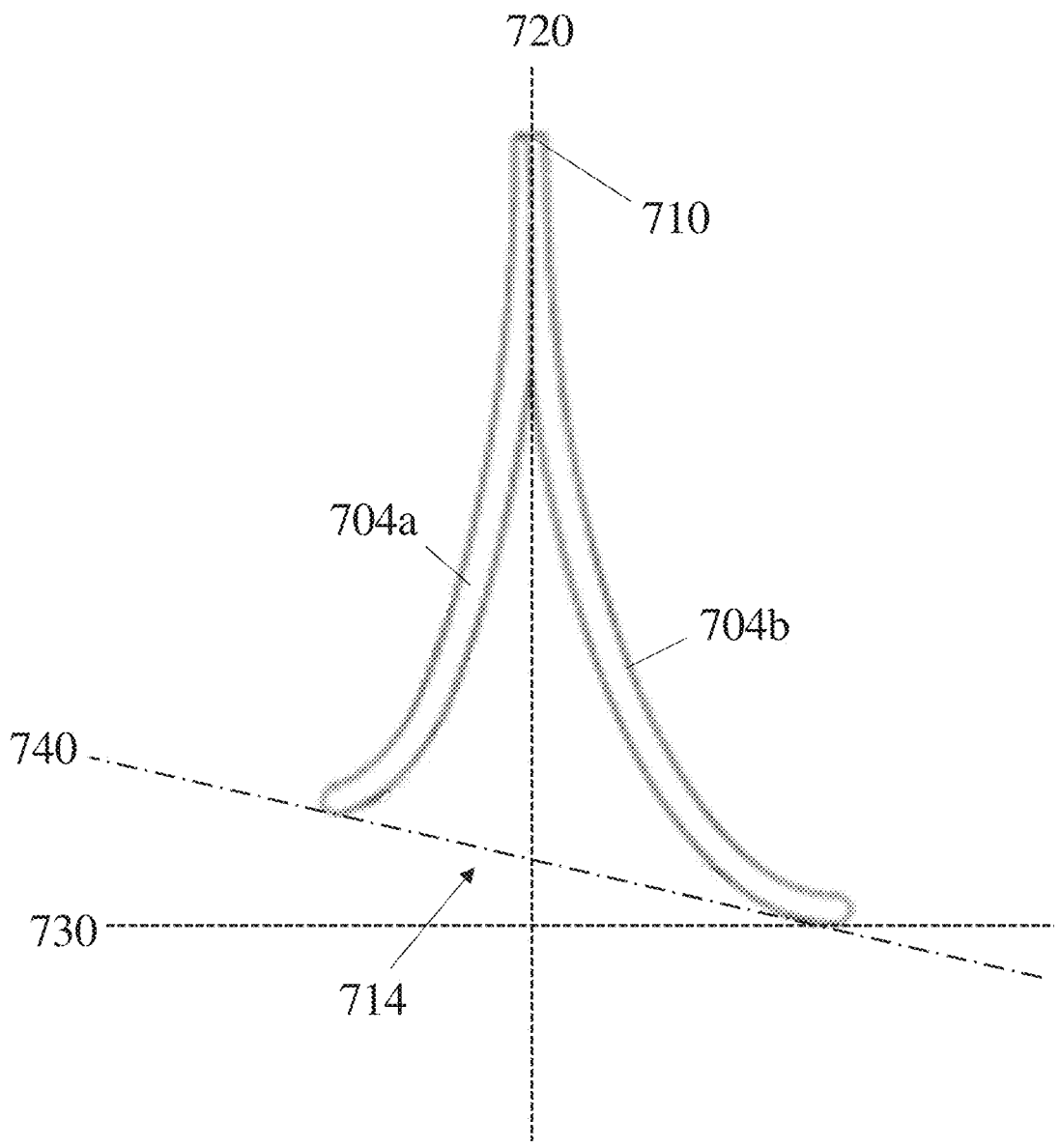
FIG. 17 is a side view of another embodiment of a valve frame section.

In some embodiments, the valve replacement device includes one or more commissural posts that extend in a direction defining a vertical. The plane formed by the opening could be orthogonal to the direction of the commissural posts, or may be tilted relative to the orthogonal. For example, in the embodiment shown in FIG. 1A, the plane formed by the opening 114 of the device is orthogonal to a vertical direction defined by the direction of the commissural posts 110. In contrast, the embodiment shown in FIG. 17, where the valve frame has sections 704a, 704b of different lengths, is an example of a tilted opening. The plane 740 defined by the opening 714 is not orthogonal to the vertical direction 720 defined by the direction of the commissural posts 710, but is instead, tilted to the orthogonal 730.

In some embodiments, the valve frame may be made up of more than one frame section. The frame section may form a U-shape having two arms extending away from the intermediate section forming a base of the first frame section. In some embodiments, the intermediate section lies on a single plane. For example, in the embodiment shown in FIGS. 1A and 1B, the valve frame has a frame section having an intermediate section 130 that lies on a single plane. This can also be seen in FIG. 4.

However, it should be appreciated that other arrangements are possible. For example, in some embodiments, the intermediate section could be non-planar, such that it is curved or otherwise shaped so that it does not lie along a single plane. In some embodiments, the intermediate section has a saddle-shaped curve, either facing up in the same direction in the U-shape, or down in an opposite direction as the U-shape.

Figure 18:
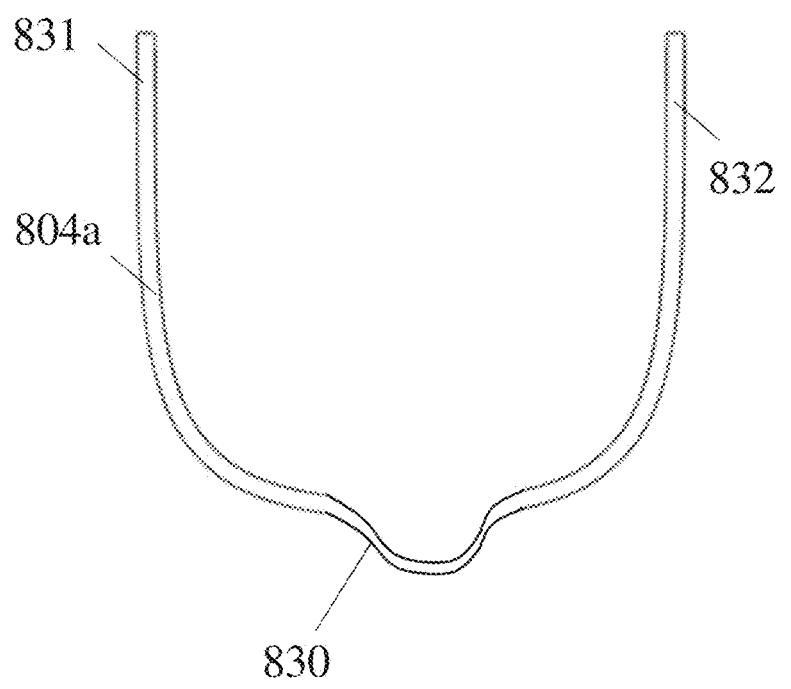
FIG. 18 is a front view of one embodiment of a valve frame section.
Figure 19:
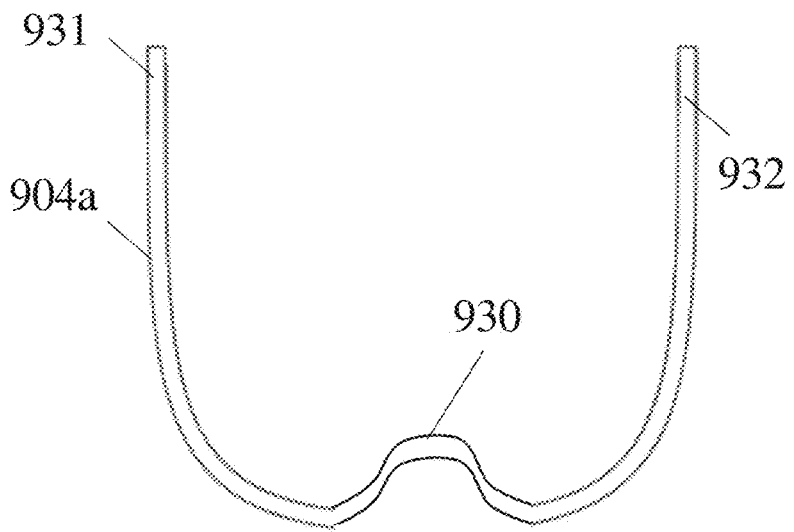
FIG. 19 is a front view of another embodiment of a valve frame section.

Two illustrative embodiments of valve frame sections with bases that are non-planar are shown in FIGS. 18 and 19. FIG. 18 is a front view of a valve frame section. The frame section 804a has a U-shape having a first arm 831 and a second arm 832 extending away from an intermediate section 830, which as a saddle-shaped curve that faces in the same direction as the U-shape. In the illustrative embodiment shown in FIG. 19, which is also a front view of a valve frame section, the frame section 904a has a U-shape having a first arm 931 and a second arm 932 extending away from an intermediate section 930, which has a saddle-shaped curve that faces in an opposite direction as the U-shape.

In some embodiments, the valve frames could be asymmetrically shaped or could expand asymmetrically due to flared or tilted commissural posts, or have different thicknesses or materials between the frame sections. The commissural posts may mirror one another with regard to size and/or shape, or they may be different from one another. The valve frame and two commissural posts may exhibit variable bending stiffness to allow for change in opening shape (i.e., cylindrical opening becomes oval/elliptical under peak diastolic loads) during the cardiac cycle.

Figure 20:
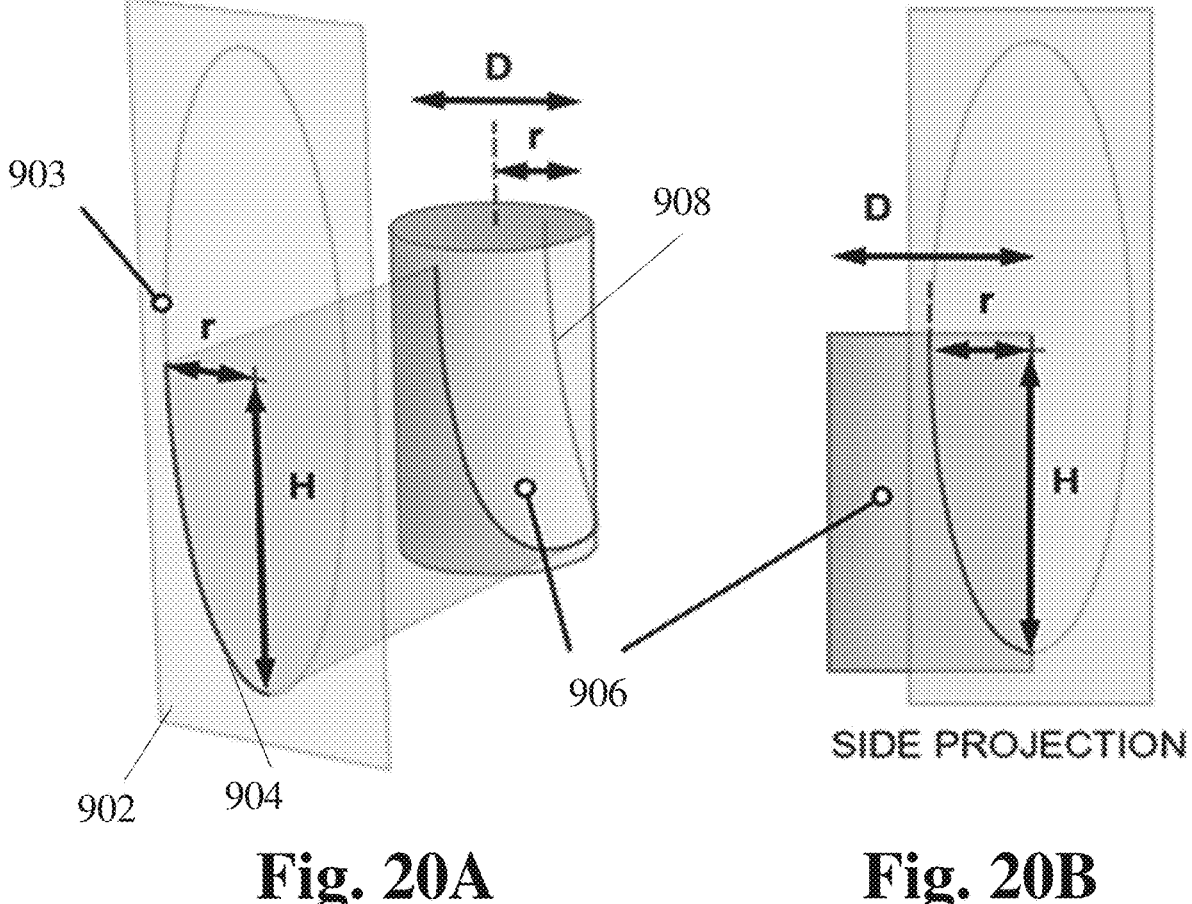
FIG. 20A is a perspective view graphical visualization of a plane containing an ellipse, and a cylinder, onto which a portion of the ellipse is projected, where the projected curve defines the curvature of one embodiment of a valve frame section.
FIG. 20B is a side view graphical visualization of the plane and cylinder of FIG. 20A.

FIGS. 20A and 20B show the curve profile of one of the frame sections of a valve frame of a valve replacement device according to some embodiments. In this embodiment, the curve profile 908 may be approximately defined by projecting an elliptical quadrant 904 from plane 902 on to a cylinder 906, which could represent the inner wall of a representative vessel. The ellipse profile 903 may have a semi-major axis length equivalent to the height of the frame (H) and a semi-minor axis having a length equivalent to radius (r) of the frame. The cylinder may have a radius equivalent to that of the frame opening. The projected ellipse co-vertex can be coincident with the cylinder centerline, the ellipse vertices, and the ellipse center such that they are all coincident with the outer edge of a central cross-section of the cylinder when viewing from the side view of FIG. 20B. In this configuration, a center of the ellipse from which the elliptical quadrant is derived coincides with a point along a circumference of an axial end of the cylinder, and a minor axis and a major axis of the ellipse are co-axial with edges of a cross-section of the cylinder.

The curve profile 908 can be mirrored about the center plane of the cylinder to generate the curve profile of the opposite frame section.

It is also contemplated that a compound curve or polynomial spline could be projected on to the cylinder to generate the curve profile of the full frame.

Figure 21:
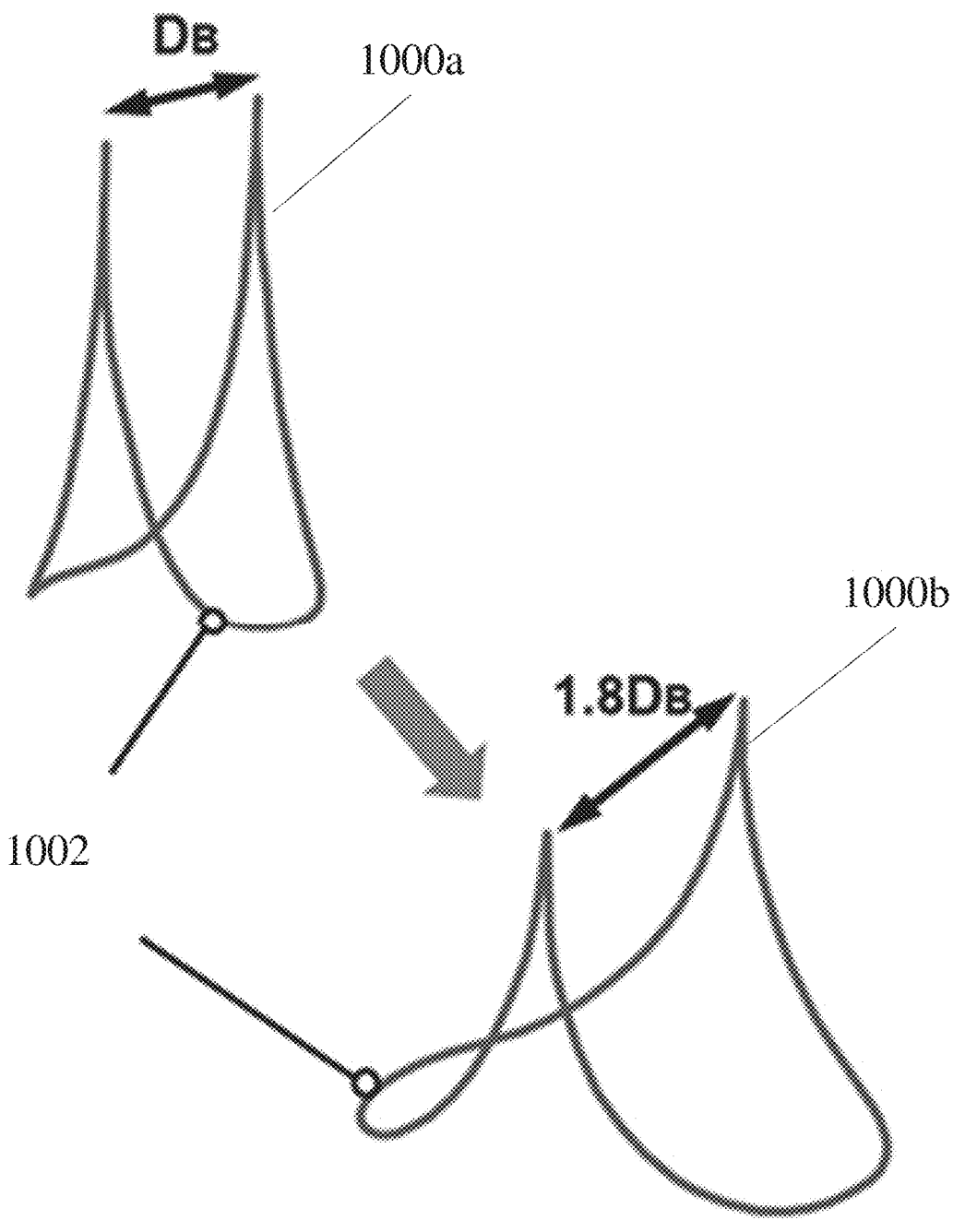
FIG. 21 is a perspective view of one embodiment of a valve frame of a valve replacement device according to one embodiment in a non-expanded state and in an expanded state.
Figure 22:
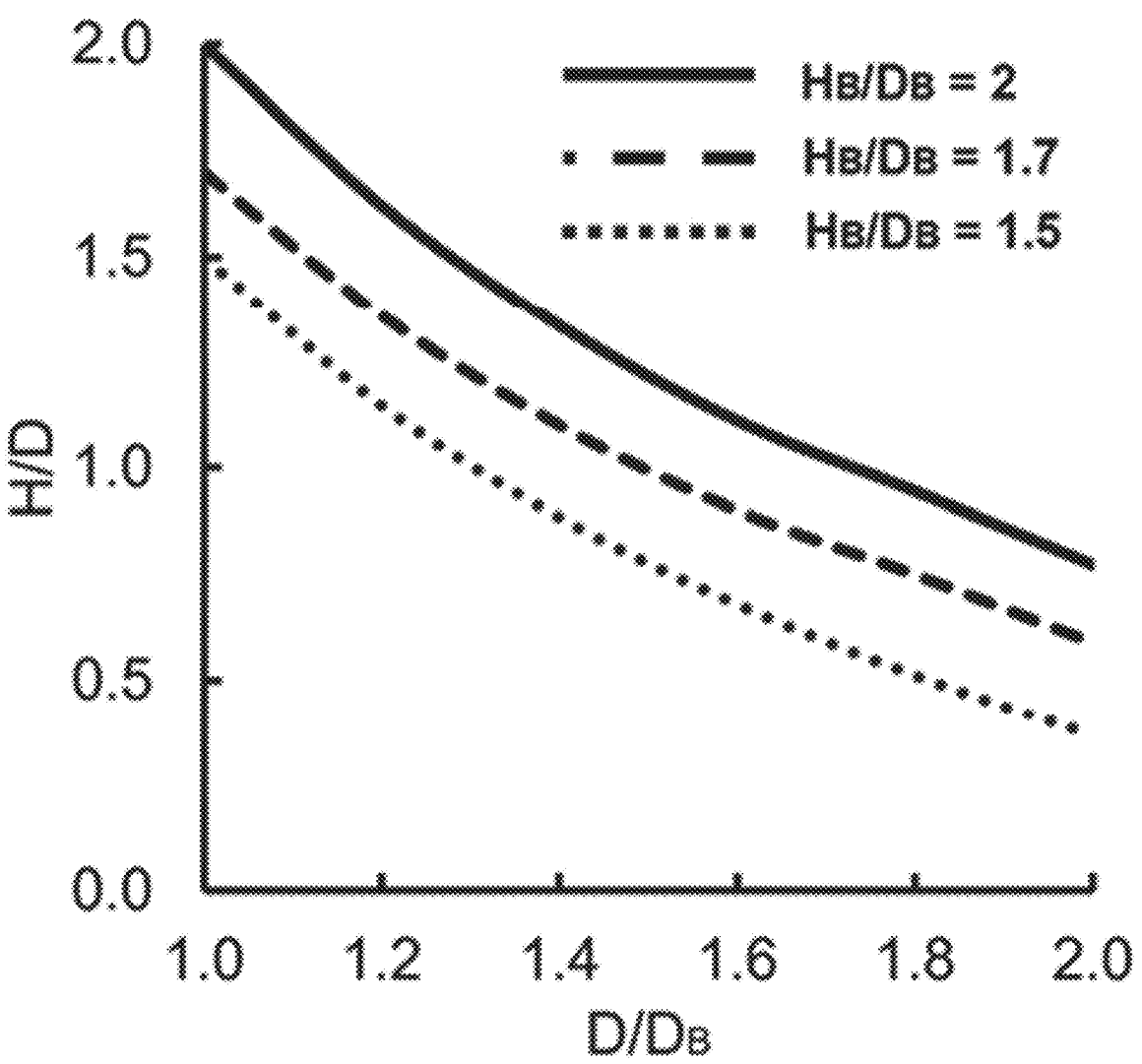
FIG. 22 is a line graph showing the height/diameter ratios of different embodiments of a valve frame of a valve replacement device with different baseline height to diameter ratios over the course of expansion.

FIG. 21 shows one embodiment of a valve frame of a valve replacement device at two different states: an unexpanded state 1000a and an expanded state 1000b. In this embodiment, the length of the valve frame 1002 is held constant during expansion of the valve frame. Instead of elongating the actual length of the valve frame, radial growth of the frame is accommodated by a reduction in valve frame height. FIG. 22 shows a line graph depicting how the height-to-diameter ratio (H/D) for embodiments of the valve frame, with differing baseline height to diameter ratios (HB/DB), change as the device expands from the baseline diameter DB to the final diameter 2DB. While embodiments with baseline HB/DB ratios of 2, 1.7 and 1.5 are shown, other ratios are also contemplated as described above.

Figures 23A, 23B:
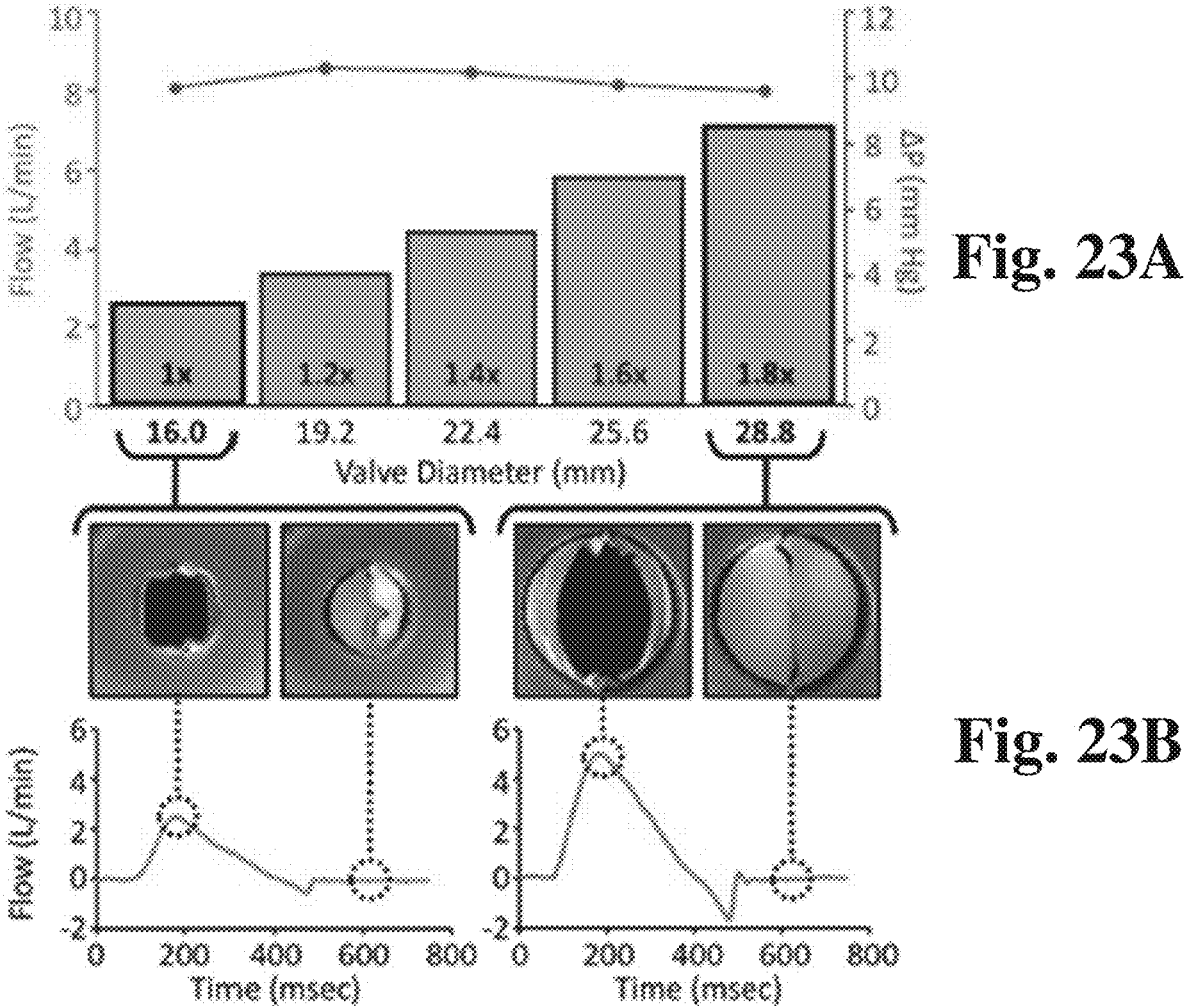
FIG. 23A is a bar graph that depicts both measured flow rate and change in pressure across a valve replacement device having the HB/DB=1.7 valve frame of FIG. 22 at different opening diameters.
FIG. 23B is a line graph illustrating the change in flow rate and flow waveform characteristics of a valve replacement device having the HB/DB=1.7 valve frame of FIG. 22 over the course of a cardiac cycle, at different opening diameters.

One embodiment of the valve replacement device was subjected to hydrodynamic performance testing. The valve replacement device was tested at five different expansion states of the valve frame (16 mm, 19.2 mm, 22.4 mm, 25.6 mm, and 28.8 mm). FIG. 23A is a bar and line graph that depicts both measured flow, regurgitation volumes and transvalvular pressure gradient (measurement of pressure drop across the valve during opening phase, systolic) across a valve replacement device having the HB/DB=1.7 valve frame of FIG. 22, at different expansion states. It was the device exhibited unobstructed forward flow throughout expansion; as flow was increased to match the increasing valve diameter (to mimic physiologic conditions in a growing patient), the transvalvular pressure gradient (.DELTA.P) did not increase with valve expansion.

Figure 23C:
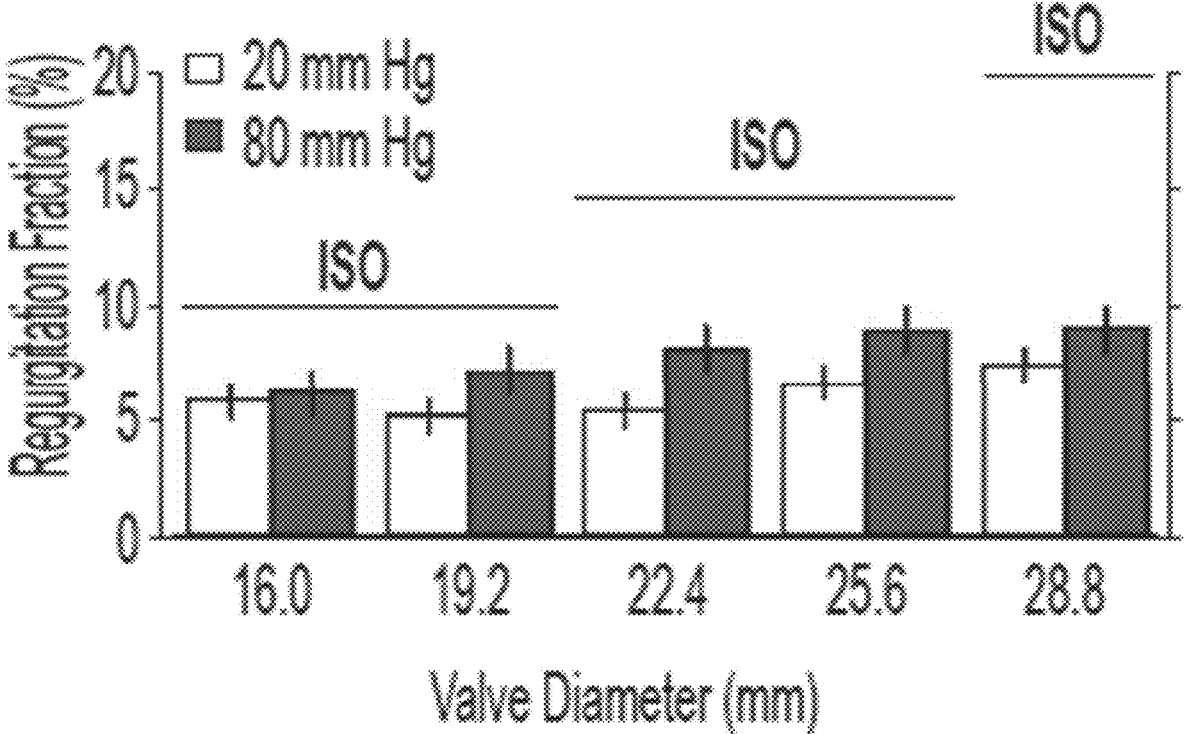
FIG. 23C is a bar graph showing regurgitant fraction at two different diastolic pressures (representing right and left heart conditions) for different opening diameters of a valve replacement device having the HB/DB=1.7 valve frame of FIG. 22.
Figure 23D:
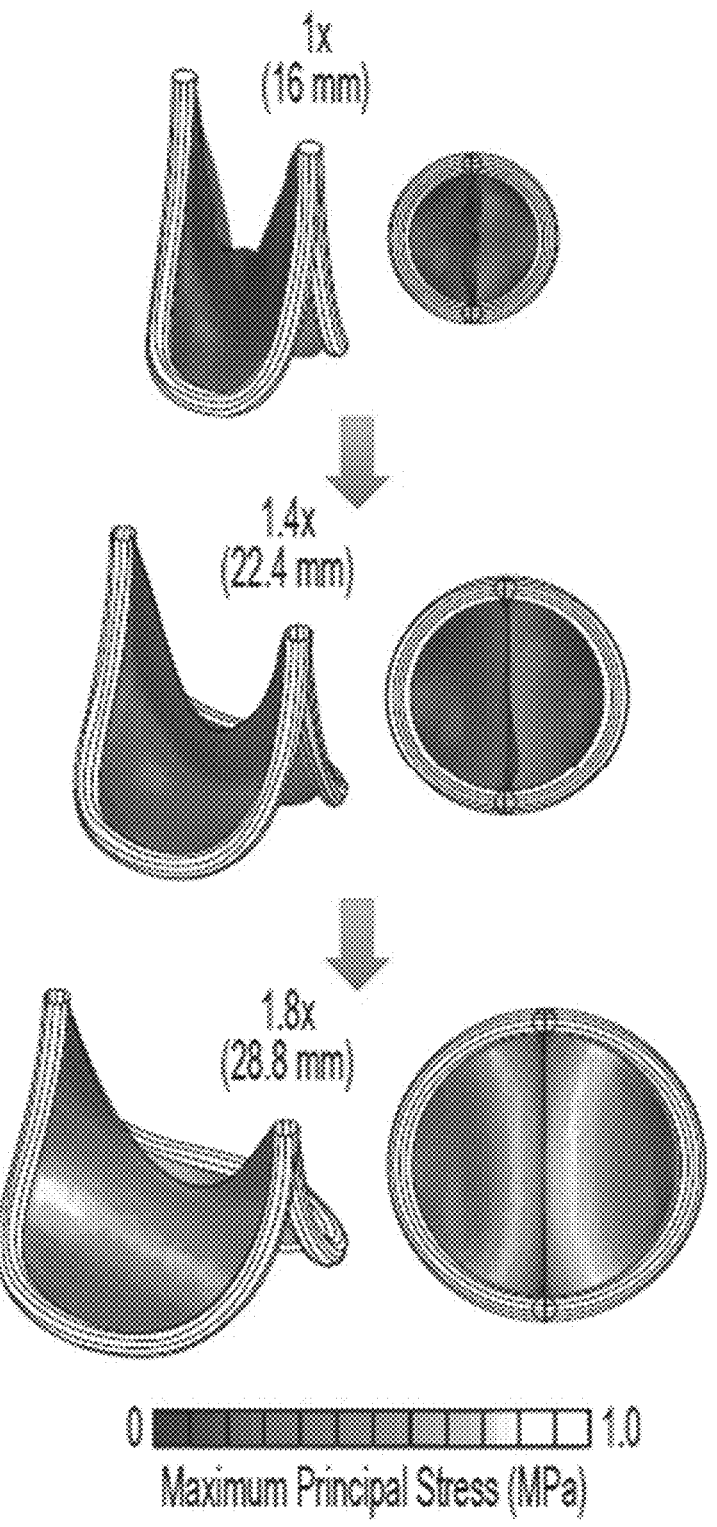
FIG. 23D shows simulated peak stresses (Maximal principal stress, MPa) under a load of 20 mmHg (approximation of right heart conditions) across leaflets of a valve replacement device having the HB/DB=1.7 valve frame of FIG. 22 when in the closed configuration, simulated using finite element analysis.

FIG. 23B shows a line graph depicting the change in flow characteristics over time as the valve replacement device opened and closed. Two valve sizes are depicted, 16 mm and 28.8 mm ID. FIG. 23C shows the regurgitant fraction measured at the various valve diameters at different diastolic pressures (i.e., pressure load on leaflets in closed state): 20 mmHg (represents physiologic right heart diastolic pressure) and 80 mmHg (represents physiologic left heart diastolic pressure). It was found that the device exhibited trivial valve leakage in the diastole condition across all states of expansion (i.e., 1 times up to 1.8 times ID). FIG. 23D shows the results of finite element analysis, conducted to evaluate magnitude and distribution of stresses on the growth-accommodating valve in the loaded state (i.e. leaflets in closed position). Data presented demonstrates peak stresses (Maximal principal stress, MPa) under 20 mmHg of loading pressure. The data showed that the magnitude of peak stresses on the valve leaflets in the closed state were relatively low throughout expansion from 16 mm to 28.8 mm (from 1 times to 1.8 times the baseline diameter). Much of the stress was distributed at the location of highest deformation, and no stress was concentrated at the site of the leaflet-frame attachment. Further, there was relatively low stresses at the frame commissures, which represents a departure from traditional 3-leaflet bio-prosthetic valve designs known in the art.

Figures 24A, 24B, 24C, 24D, 24E, 24F, 24G, 24H:
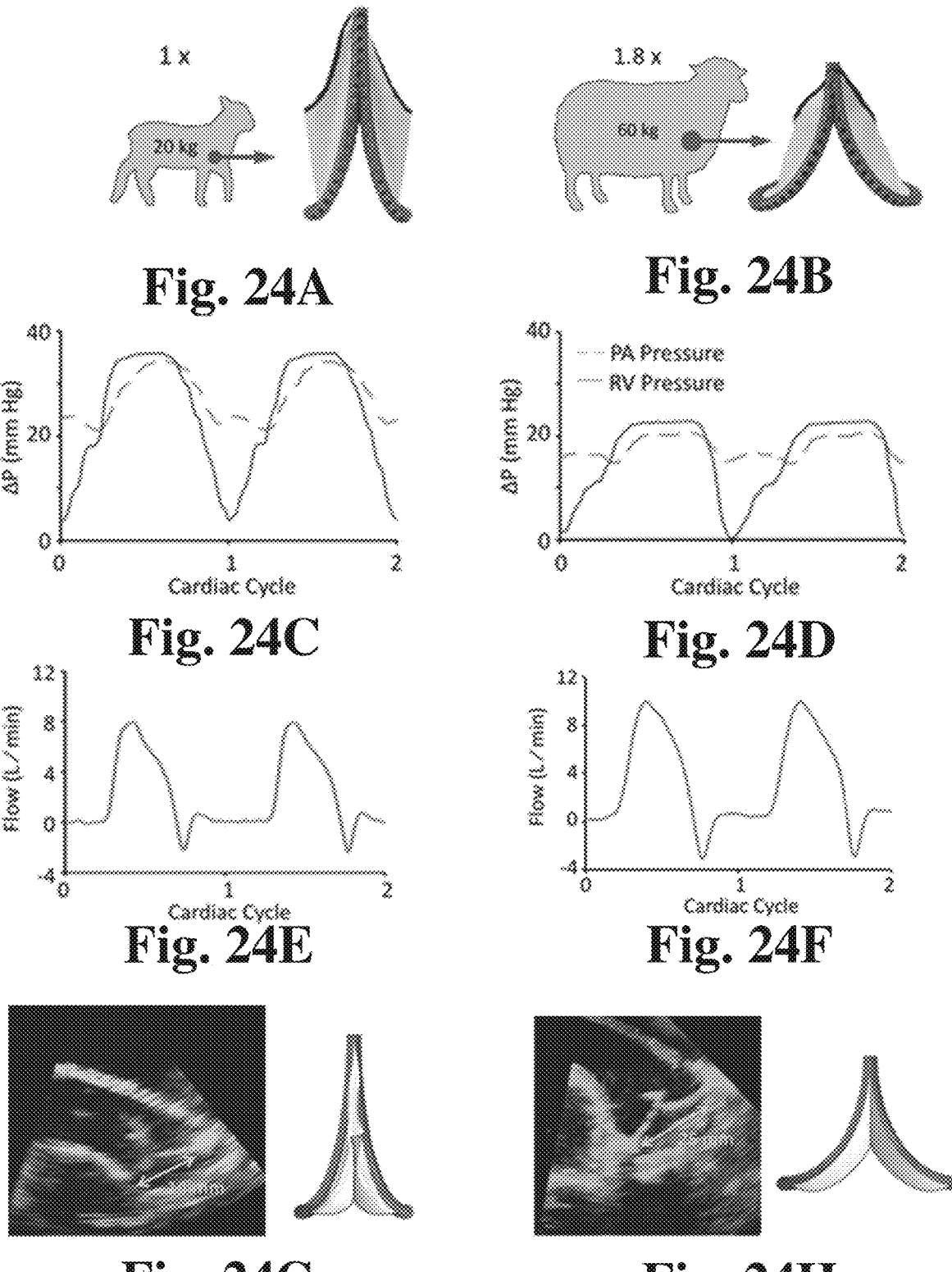
FIG. 24A is a graphic conveying that one embodiment of the valve replacement device was tested in vivo in 20 kg lambs.
FIG. 24B is a graphic conveying that one embodiment of the valve replacement device was tested in vivo in 60 kg sheep.
FIG. 24C is a line graph showing the pressure difference (transvalvular pressure gradient, .DELTA.P) between the right ventricle and pulmonary artery of 20 kg lambs, with the valve replacement device implanted, over the course of the cardiac cycle.
FIG. 24D is a line graph showing the pressure difference (transvalvular pressure gradient, .DELTA.P) between the pulmonary artery and right ventricle of 60 kg sheep, with the valve replacement device implanted, over the course of the cardiac cycle.
FIG. 24E is a line graph showing the flow waveform and regurgitation volumes generated by the valve replacement device in its baseline configuration (1. times.) over the course of the cardiac cycle in 20 kg lambs.
FIG. 24F is a line graph showing the flow waveform and regurgitation volumes generated by the valve replacement device in its fully expanded configuration (1.8. times.) over the course of the cardiac cycle in 60 kg adult sheep.
FIG. 24G shows an echocardiogram of one of the 20 kg lambs, showing the valve replacement device implanted in its baseline configuration (1. times.) at 14 mm ID, alongside a graphic of the valve replacement device.
FIG. 24H shows an echocardiogram of one of the 60 kg sheep, showing the valve replacement device expanded to 25 mm (1.8. times.), alongside a graphic of the valve replacement device.

FIGS. 24A, 24C, 24E, and 24G show the results of in vivo testing conducted by implanting one embodiment of the valve replacement device with a 14 mm internal diameter in four lambs. FIGS. 24B, 24D, 24F, and 24H show the results of in vivo testing where the same embodiment of the valve replacement device expanded to 25 mm (1.8 times baseline diameter) and implanted in four adult sheep. In these studies, the valve replacement devices were used to replace the pulmonary valve of the lambs and sheep. FIGS. 24C and 24D show the measured change in the right ventricular (proximal to the valve) and pulmonary artery pressure (distal to the valve), over the course of the cardiac cycle of the animals. It was found that regardless of the valve expansion state, there was no transvalvular gradient across the valve. FIGS. 24E and 24F show representative flow waveforms of measured physiological flow across the valve replacement devices over the course of the cardiac cycle. It was found that regardless of the diameter of the opening, forward flow of the physiological fluids were unobstructed, and there was no leakage across the valve replacement devices in diastole. FIGS. 24G and 24H show echocardiograms conducted to visualize the implanted valve replacement devices in vivo. The changes in frame height and leaflet coaptation height at different states of valve diameter expansion become apparent between the two animal groups.

FIGS. 25A-D show one embodiment of the valve frame of a valve replacement device. In this embodiment, the valve frame 2500 includes a top reinforcement features such as a reinforcement strut 2504 attached to the commissures 2502 of the frame. The device also includes lower reinforcement strut 2506 connecting the lower portions of the frame sections. In this embodiment, top reinforcement strut 2504 has an circular profile in the fully expanded state, and attaches to the commissures at diametrically opposed points of the annulus. The top reinforcement strut of this embodiment includes undulations 2508 that serve to reduce the diameter of the top reinforcement strut when the feature is in an unexpanded state. As the frame expands, the pair of commissures separate, increasing the distance between the pairs of commissures and applying an expanding stress to the top reinforcement strut. The undulations permit the top reinforcement strut to expand with the feature by straightening out the undulations. The total length of the reinforcement strut may be equal to or larger than the largest possible circumference of the opening to ensure that the frame can expand to the largest possible circumference without limiting expansion, obstructing the valve opening, or distorting the geometry of the leaflet attachment frame.

While an annular top reinforcement strut with undulations is depicted in FIGS. 25A, 25C, and 25D, it should be understood that any shape or arrangement that connects the commissures of the frame sections while allowing the frame to expand is also contemplated. For example, instead of an annular shape, the top reinforcement strut could be elliptical, diamond-shaped, or polygonal, or could comprise separate connecting portions instead of one continuous closed loop. The top reinforcement strut could also have a telescoping design, be made of an elastic material that can be reversibly deformed when the reinforcement strut is expanded, or simply have more or fewer or larger or smaller undulations than depicted in the figures.

Figure 26:
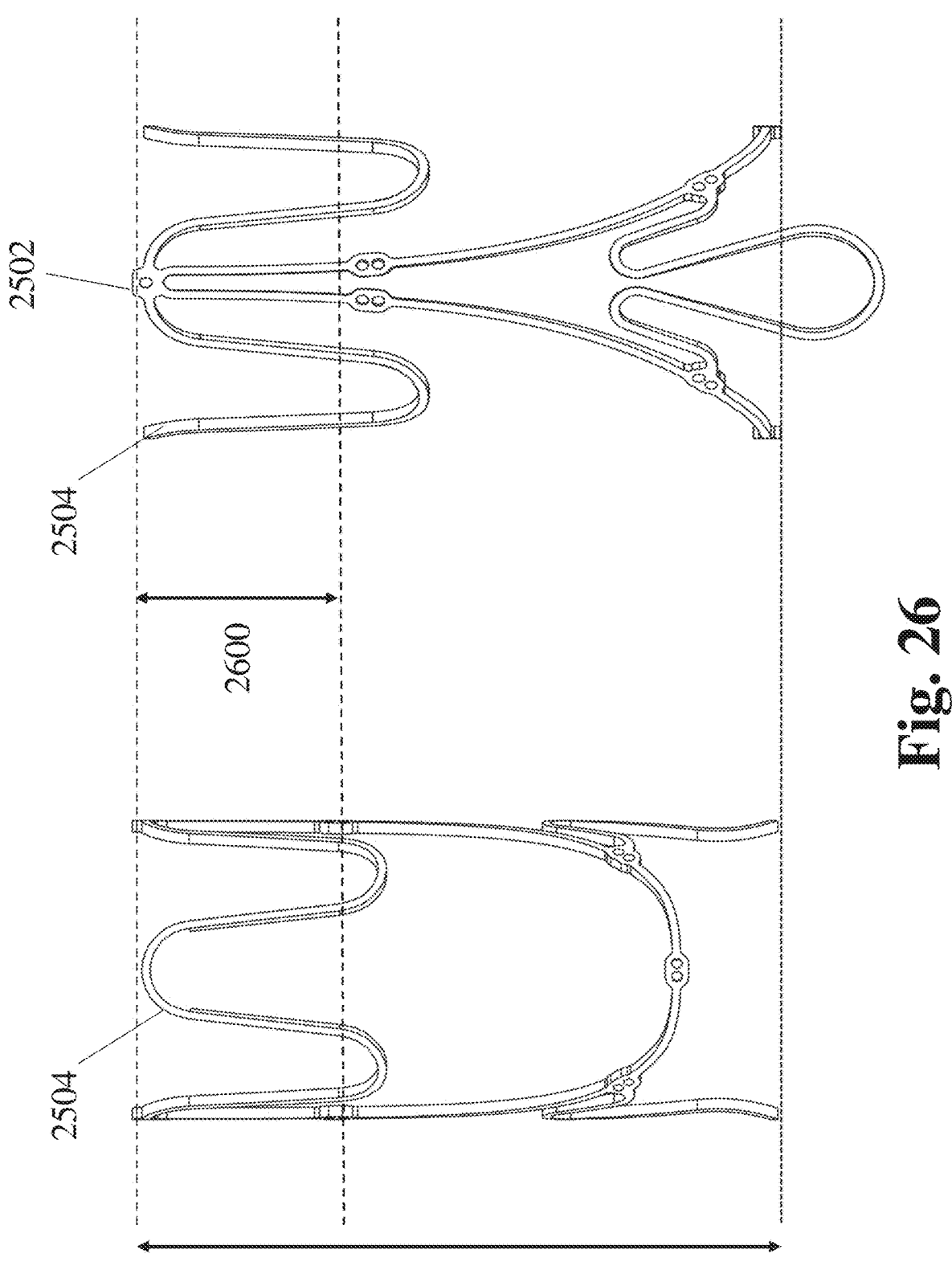
FIG. 26 shows side and front views of one embodiment of a valve frame of a valve replacement device, annotated to depict an attachment zone for a top reinforcement strut.

FIG. 26 shows an attachment zone 2600 for the top reinforcement strut. In some embodiments, the top reinforcement strut is attached to the valve frame within the top 30% of height of the commissure. However, it should be understood that other embodiments where the top reinforcement strut is attached outside of the top 30% zone of the device are also contemplated.

In some embodiments, the top reinforcement strut is attached to the frame at or near the top of the pairs of commissures.

Lower reinforcement strut 2506 as depicted in the embodiment of FIGS. 25A-D includes undulation 2508 that allows the lower support feature to have a smaller diameter when the valve frame is in its non-expanded configuration. As the frame sections separate when the valve diameter increases, the undulation straightens out, expanding the diameter of lower reinforcement strut 2506 to allow the lower feature to expand with the frame.

While a lower reinforcement strut with a distinct tear drop shape extending below the frame of the device is depicted, the lower feature could be of any shape that allows the lower feature to help maintain the desired geometric profile of the leaflet attachment frame across expansion state. The lower reinforcement strut may also be used as a fixation site for transcatheter deployment, or for attachment to native heart structures, or for other applications. For example, the lower support feature could have a telescoping design, be made of an elastic material that can be reversibly deformed when the feature is expanded, or simply have more or fewer or larger or smaller undulations.

Figure 27:
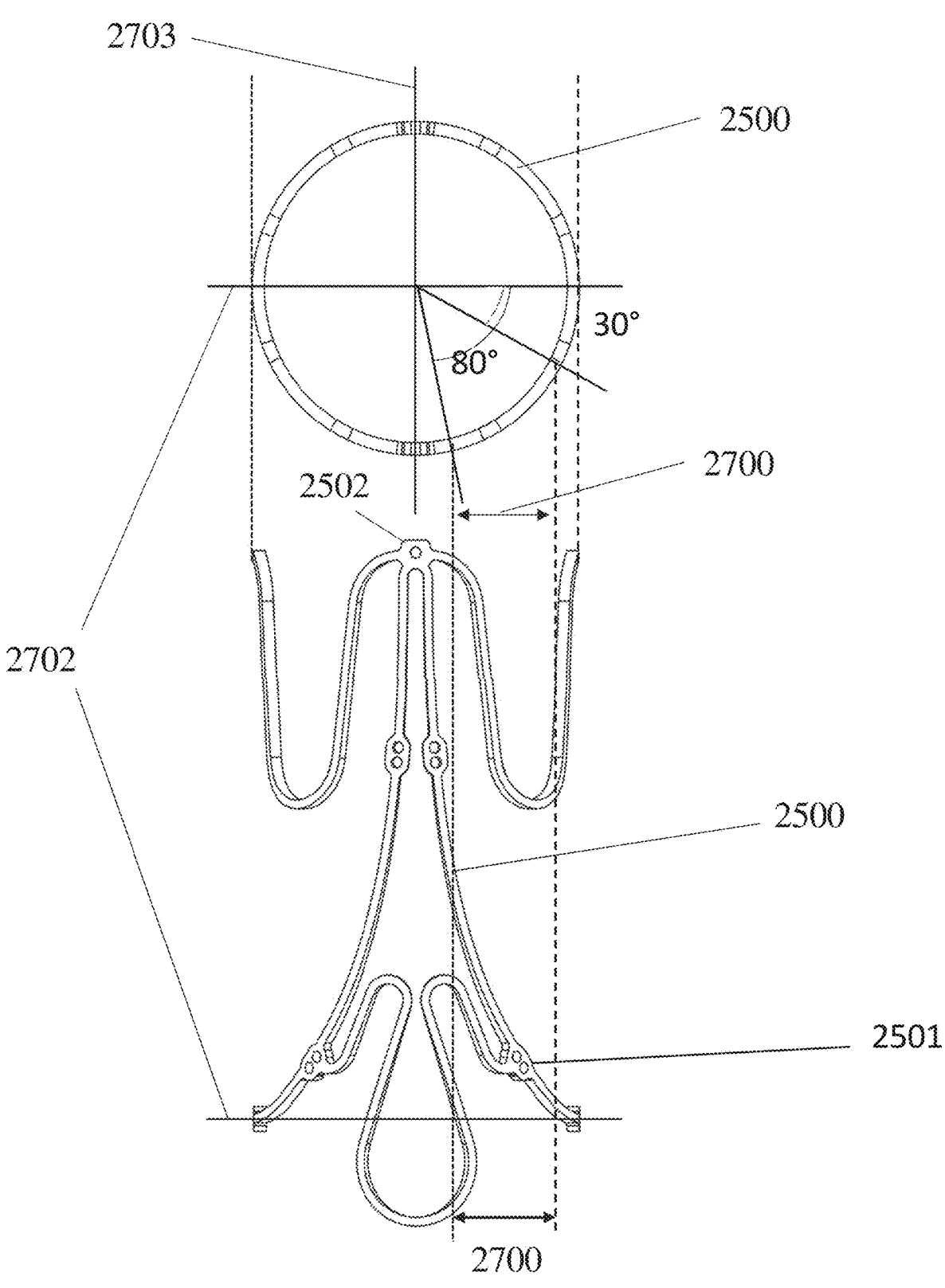
FIG. 27 shows top and side views of one embodiment of a valve frame of a valve replacement device, annotated to depict an attachment zone for a bottom reinforcement strut.

FIG. 27 shows an attachment zone 2700 for the lower reinforcement strut. FIG. 27 shows a top view of the valve frame from FIG. 25B, imposed over the side view from FIG. 25D. Line 2702 is an imaginary axis that passes through the diameter of the opening and is perpendicular to an imaginary line connecting the tops of the two commissures of the valve frame. When viewing the top view, if line 2702 were the x-axis and the perpendicular line 2703 were the y-axis, assuming 0. degree, begins on the right intersection between line 2702 and the frame (at 0. degree, of a unit circle) and opens counterclockwise, attachment zone 2700 is between 280. degree, and 330. degree. As seen in FIG. 27, the 280. degree, to 330. degree, corresponds to the lower portions of the arc of the frame sections as seen in the side view. In some embodiments, the lower feature is attached at 310. degree, as represented by point 2501.

It should be understood that other embodiments where the lower reinforcement strut is attached outside of the attachment zone 2700 of the device are also contemplated.

Figure 28:
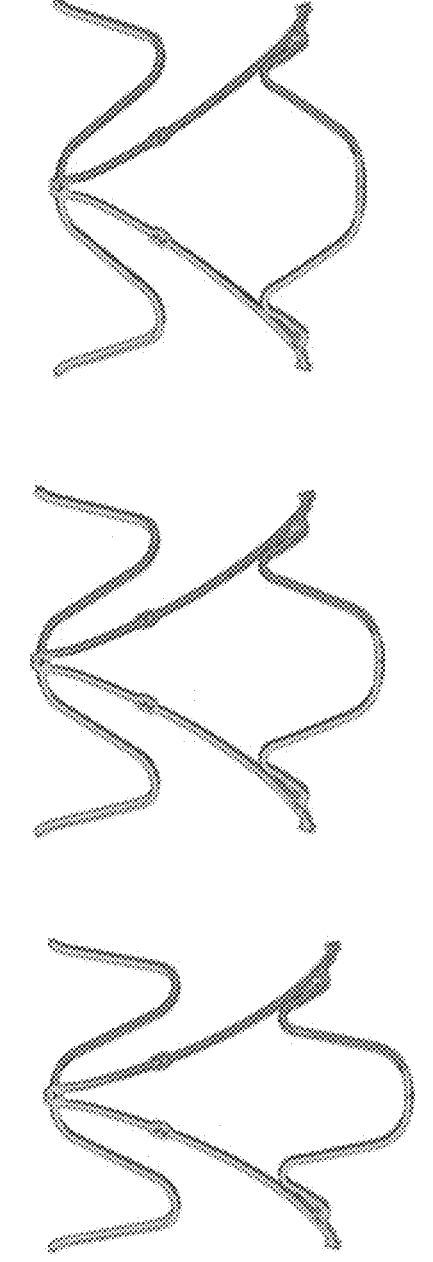
FIG. 28 shows side views of the valve frame of FIG. 25A expanded to progressively larger opening diameters.

FIG. 28 shows side views of the valve frame of FIG. 25A at different expansion sizes (12.7 mm, 14 mm, 16 mm, 18 mm, 20 mm, 22 mm, and 24 mm respectively).

Figure 29:
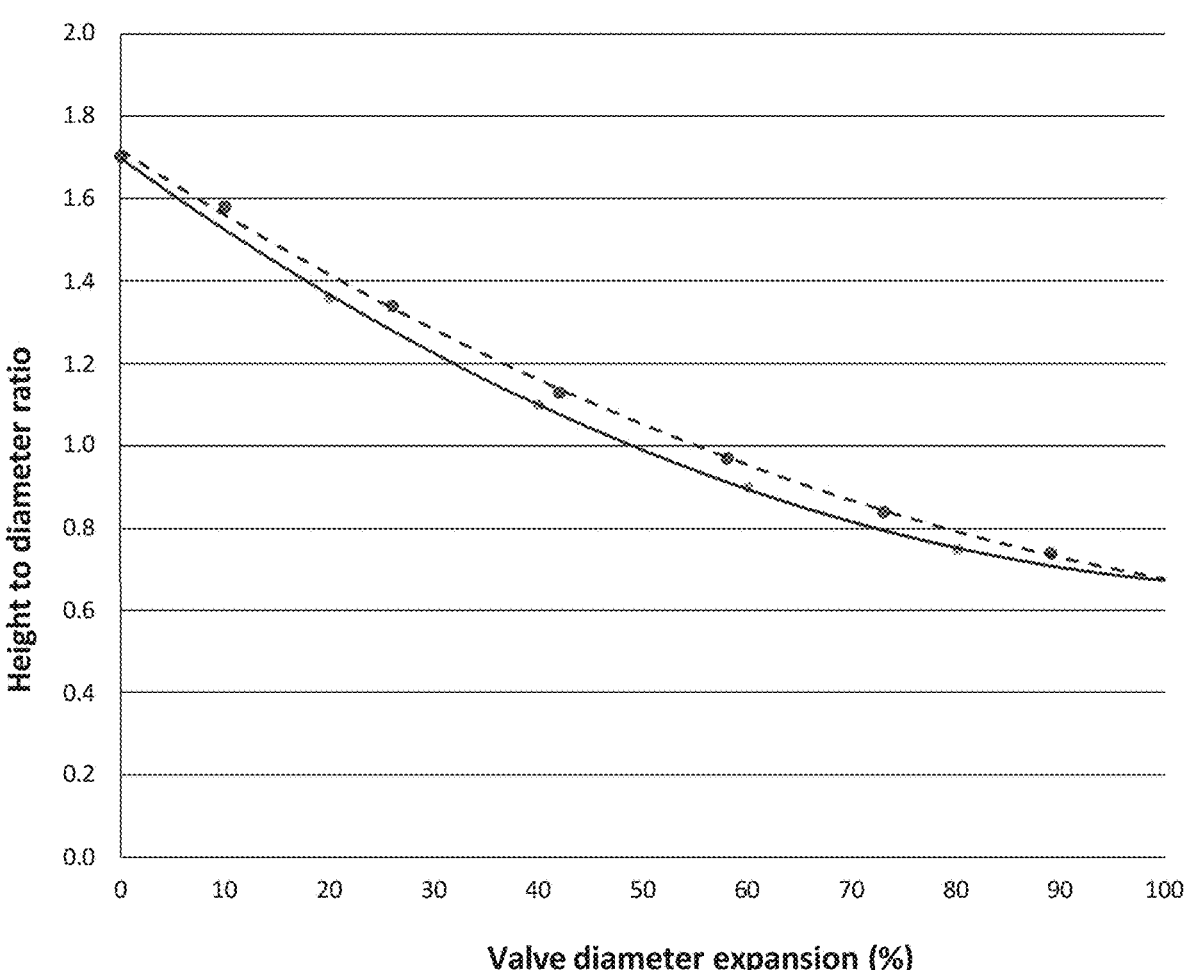
FIG. 29 is a scatter plot showing the height to diameter ratio of a valve replacement device having the valve frame of FIG. 25A compared to an embodiment of a valve replacement device that does not include reinforcement struts at the valve frame.

FIG. 29 shows a graph depicting how the height to diameter ratio of the embodiment of FIGS. 25A-D having reinforcement struts, and the embodiment of FIG. 21, which does not have reinforcement struts, changes with expansion of valve diameter. The embodiment with reinforcement struts was expanded via balloon expansion, while the embodiment without reinforcement struts was expanded in simulation in 20% increments. The solid line represents the behavior of the valve replacement device without reinforcement struts (e.g. FIG. 21), while the dashed line represents the behavior the valve replacement device of FIG. 25A-D with both a top and lower reinforcement strut. The devices each have a baseline height to diameter ratio of 1.7:1 and were expanded to double their baseline diameter. It was found that the devices both achieve a very similar kinematic profile of an expanding valve frame in which the height to diameter ratio decreases as the valve frame diameter increases.

Figures 30A, 30B:
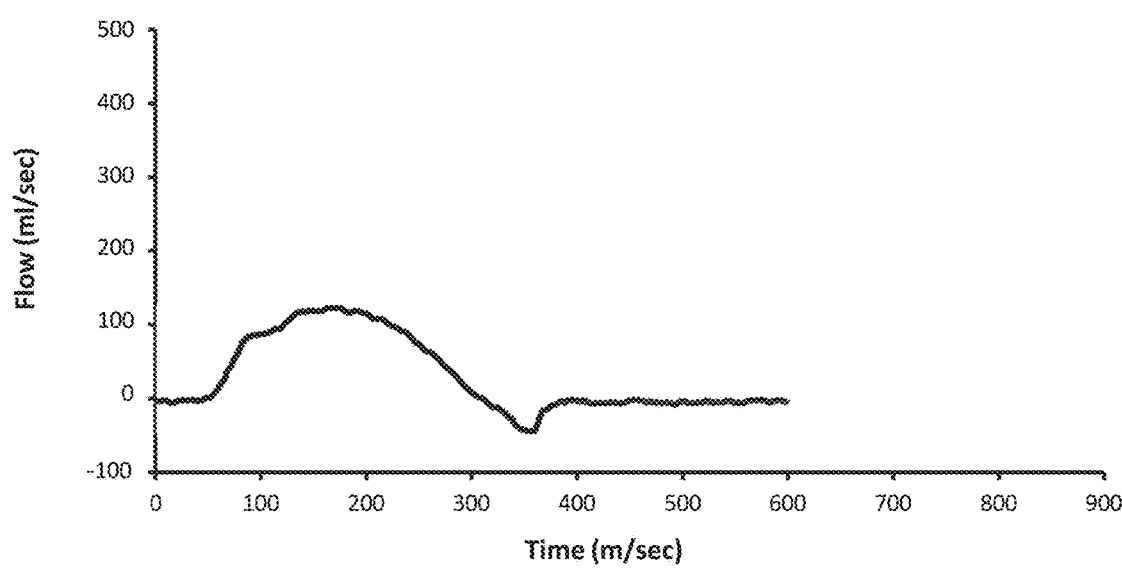
FIG. 30A is a line graph showing flow waveform and regurgitation volumes over the course of a simulated circulatory flow loop, through the valve replacement device of FIG. 25A, at baseline diameter, during in vitro hydrodynamic testing.
FIG. 30B is a table containing data obtained over the course of the in vitro testing of a valve replacement device having the valve frame of FIG. 25A, at baseline diameter.
Figures 31A, 31B:
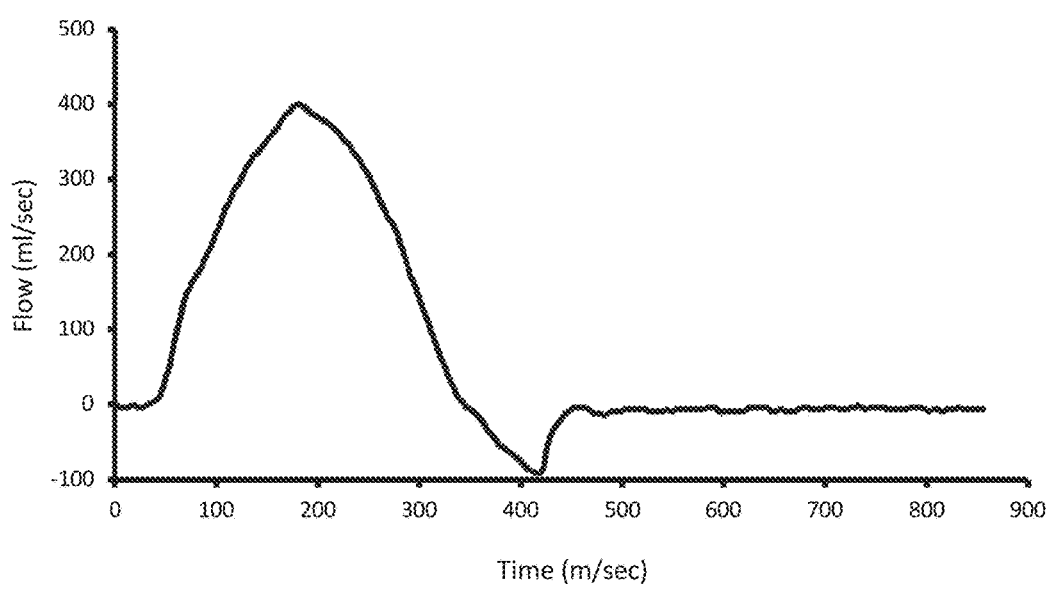
FIG. 31A is a line graph showing flow waveform and regurgitation volumes over the course of a simulated circulatory flow loop, through a valve replacement device having the valve frame of FIG. 25A, at an expanded size of 1.8 times the baseline diameter, during in vitro hydrodynamic testing.
FIG. 31B is a table containing data obtained over the course of the in vitro testing of a valve replacement device having the valve frame of FIG. 25A, at an expanded size of 1.8 times the baseline diameter.

FIGS. 30A-B and FIG. 31A-B show the results of in vitro hydrodynamic performance testing of a valve replacement device having the valve frame of FIG. 25A-D. A functional prototype of the device was tested in a sophisticated mock circulatory flow loop at various states of expansion. The device was tested at its baseline configuration (12.7 mm internal diameter, 1. times.), then expanded with a balloon catheter to 23 mm internal diameter (1.8. times.) and re-tested under physiologic pressure and flow conditions. FIG. 30A shows the flow profile across the device at an opening diameter of 12.7 mm over the course of a cardiac cycle. FIG. 30B shows other measured values including the transvalvular pressure gradient across the valve, fluid flow profile through the device, including the leakage volume and the regurgitant fraction. FIG. 31A shows the flow profile across the device at 1.8 times the baseline diameter (23 mm) over the course of the cardiac cycle. FIG. 31B reflects the same types of measurements as FIG. 30B but for the device at an expanded state of 23 mm in opening diameter. It was found that valve functionality remained unchanged at each tested valve diameter.

Figure 32C:
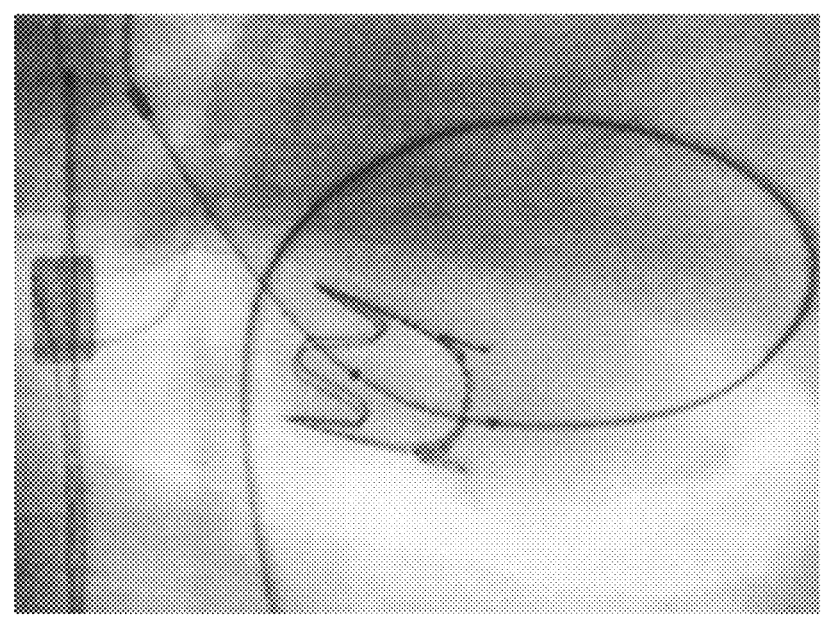
FIG. 32C is an x-ray radiograph of the valve replacement device of FIG. 32A in a partially expanded configuration.
Figure 32B:
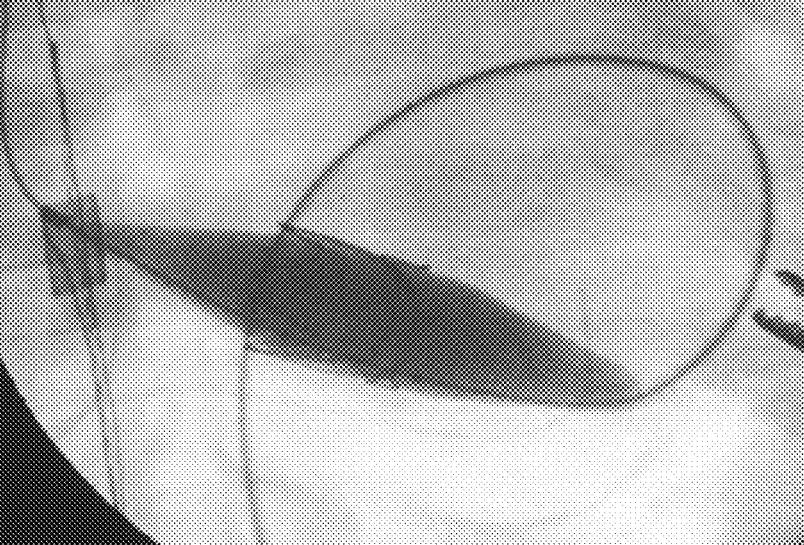
FIG. 32B is an x-ray radiograph of the valve replacement device of FIG. 32A in the process of transcatheter balloon dilation.
Figure 32A:
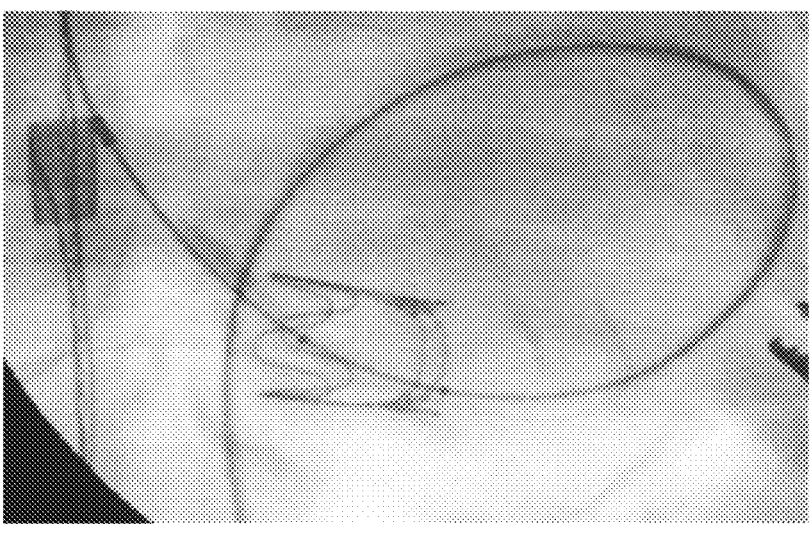
FIG. 32A is an x-ray radiograph of the valve replacement device according to one embodiment implanted in a 25 kg sheep.
Figures 34A, 34B, 34C, 34D:
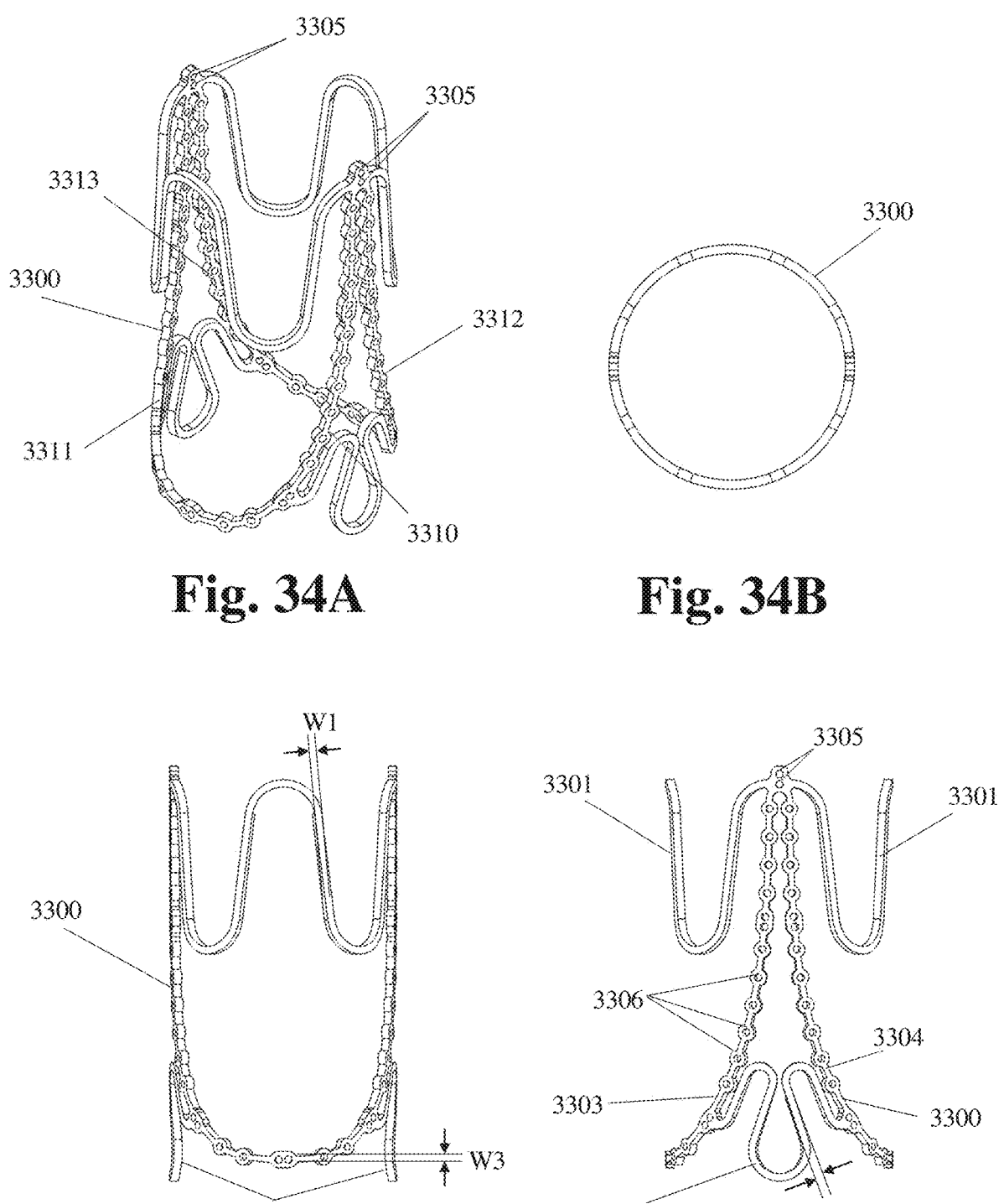
FIG. 34A is a perspective view of one embodiment of a valve frame of a valve replacement device.
FIG. 34B is a top view of the valve frame according to the embodiment of FIG. 34A.
FIG. 34C is a front view of the valve frame according to the embodiment of FIG. 34A.
FIG. 34D is a side view of the valve frame according to the embodiment of FIG. 34A.

FIGS. 32A-32C show the valve replacement device according to one embodiment implanted in a 25 kg sheep. The unexpanded (12.7 mm) valve replacement device was implanted in the pulmonary valve position in 25 kg sheep. The device was dilated to 16 mm, 18 mm, and 20 mm using transcatheter balloon dilation. FIG. 32A shows the device dilated to 16 mm, FIG. 32B shows the dilation process, and FIG. 32C shows the device post dilation of FIG. 32B at 18 mm. It was found that the valve geometries (the leaflet attachment line and reinforcement struts) matched the geometric profiles pre and post expansion. The valve success-fully expanded under radial force generated by clinical standard balloon catheter in an implanted in vivo setting using balloon pressure recommended by the balloon manu-facturer, and the valve frame maintained its structural integ-rity after multiple sequential dilations.

FIGS. 33A-33D show an alternative embodiment of a valve frame 3200 with a shortened lower reinforcement strut 3206. In this embodiment, the lower reinforcement strut undulations has a shorter tear drop shaped undulation trough 3208 that does not extend past the bottom of the valve frame.

FIG. 34A-34D show an alternative embodiment of a valve frame 3300 with a plurality of holes 3306 along the frame of the device. It is contemplated that having holes along the frame provide anchoring points for suturing the leaflets to the frame. It should be understood that any number of holes, spaced any distance from each other, of any size, could be used. The holes may not be formed directly into body of the frame but may instead be formed in sections that stem off of the frame body.

FIGS. 35A-35D show an alternative embodiment of a valve frame 3400 including middle reinforcement struts in addition to top reinforcement struts 3402 and lower rein-forcement strut 3406. In this embodiment, the middle rein-forcement strut 3410 may have two semi-annular portions that connect the two frame sections. The portions of the middle reinforcement strut 3410 may include undulations 3412 that may reduce the size profile of middle attachment feature. Similar to the top and lower reinforcement struts, the undulations can straighten out to allow the middle reinforcement strut to expand with the frame. The middle reinforcement strut may have a length that is equal to or greater than the perimeter of the opening at maximum expansion.

FIG. 36A-36B show an alternative embodiment of a valve frame 3500 with the plurality of holes 3503 along the frame of the device that may provide anchoring points for suturing the leaflets to the frame, as well as a middle reinforcement strut 3510 to aid in reinforcement of the frame.

While embodiments have been depicted with no rein-forcement struts or one or more of a top, middle, and lower reinforcement strut, it should be understood that contem-plated embodiments could have any number of reinforce-ment struts located in any number of locations. The rein-forcement struts may serve to allow the frame to expand to their fully expanded diameters while providing structural support to the frames such that the geometry of the expanded frame allows for preserved valve function (e.g., unob-structed forward flow and no or minimal regurgitation).

In some embodiments, the reinforcement struts and/or valve frame may be constructed from SS-316L or CoCr-MP35N, or any other material with sufficient stiffness to provide structural integrity to the device, while being ductile enough to allow undulations to straighten with valve frame expansion, or to otherwise allow other expanding designs to expand with the valve frame expansion. The reinforcement struts may have widths and wall thicknesses identical to those of the frame, or may be thicker or thinner than the frame.

In some embodiments, the reinforcement struts can be laser cut, stamped, or otherwise cut from a single sheet of material. In other embodiments, the reinforcement struts need not be formed from a single piece of material. For example, a reinforcement strut can be made of a combina-tion of different materials, e.g., by joining one piece of material to another piece of material. A reinforcement struts may have a uniform or non-uniform thickness.

Figures 37A, 37B, 37C:
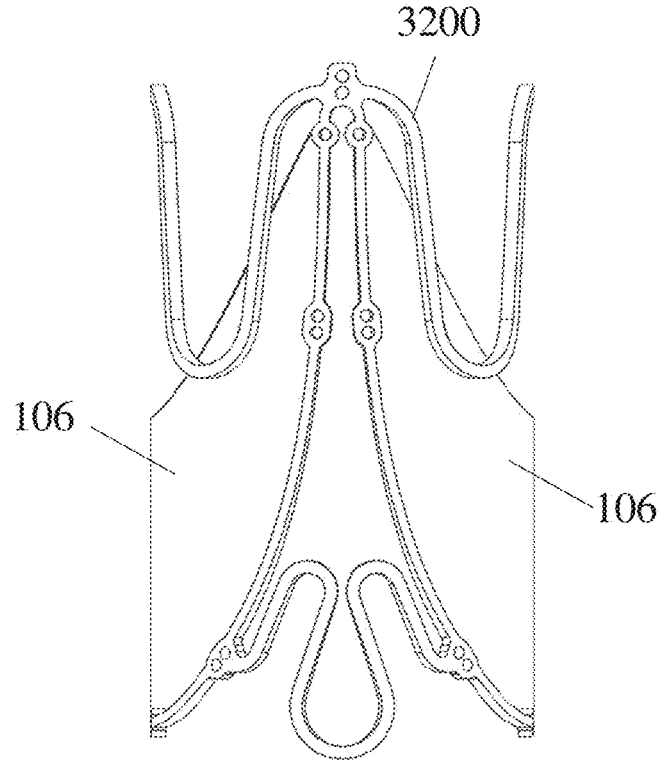
FIG. 37A is a perspective view of the valve frame of FIG. 33A with leaflets attached to the frame.
FIG. 37B is a front view of the arrangement of FIG. 37A.
FIG. 37C is a side view of the arrangement of FIG. 37A.
Figure 38A:
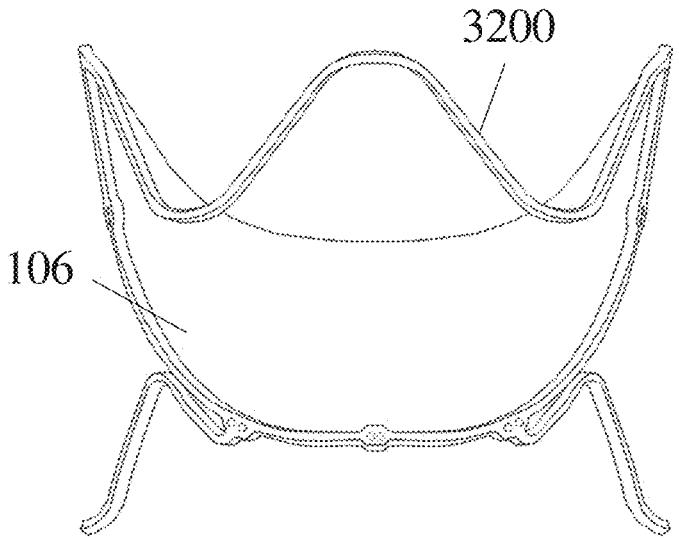
FIG. 38A is a front view of the arrangement of FIG. 37A in an expanded state.
Figure 38B:
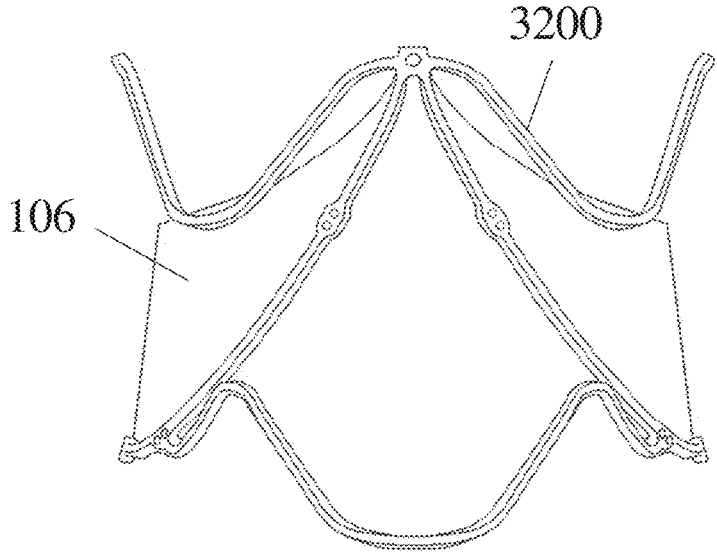
FIG. 38B is a side view of the arrangement of FIG. 37A in an expanded state.

FIGS. 37A-37C show the valve frame 3200 of the FIG. 33A embodiment attached to leaflets 106 to illustrate how leaflets may be attached to the valve frame. For the other reinforcement strut embodiments shown in FIGS. 25A, 33A, 34A, 35A, and 36A, leaflets may be attached to such valve frames in a similar orientation as shown in FIGS. 37A-37C. FIG. 38A shows a front view of the valve frame and leaflet combination of FIG. 37A in an expanded state, and FIG. 38B shows a side view of FIG. 38A.

FIGS. 39A-39D show an alternative embodiment of the valve replacement device. In this embodiment, the valve frame 3900 includes a top reinforcement strut 3904 and lower reinforcement strut 3906 connecting the lower por-tions of the frame sections. This embodiment is an example of how the mechanical properties and/or geometry and/or width or thickness of the frame support features can be modified to impact the expansion geometry (i.e., shape of the opening) of the valve frame 3900. In this embodiment, the top reinforcement strut 3904 has a thickness that is reduced compared to the thickness of the leaflet attachment line and the thickness of the lower reinforcement strut 3906, making it less stiff than these other frame components. Without wishing to be bound by theory, it is contemplated that these modifications result in an altered expansion profile of the device wherein the pair of commissures undergoes greater deformation in the radial direction due to being less constrained, resulting in asymmetric/non-circular widening at the upper end of the valve replacement device. The lower reinforcement strut maintains a circular opening at the base of the valve.

Figures 40A, 40B:
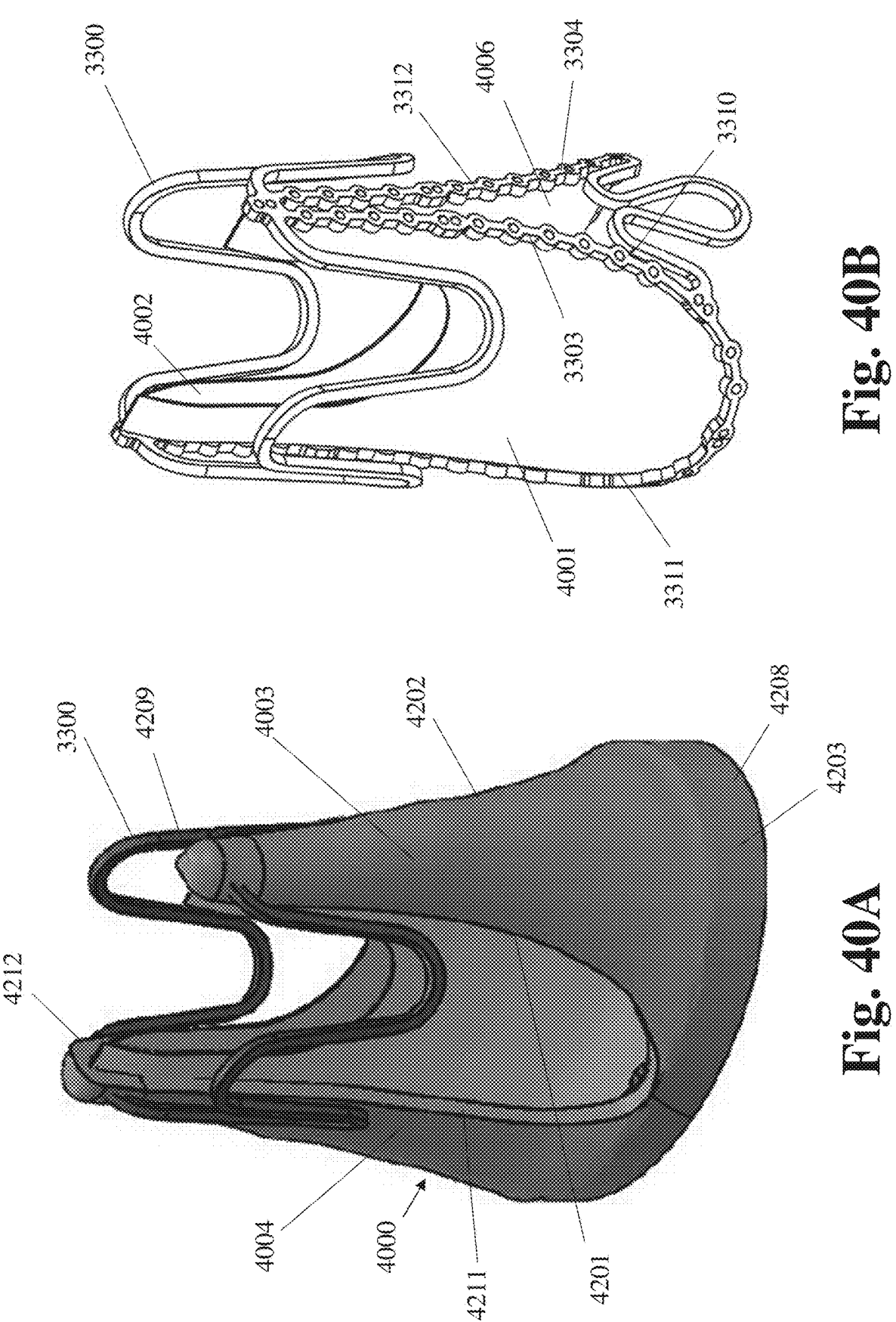
FIG. 40A is a perspective view of a valve replacement device according to one embodiment.
FIG. 40B is a perspective view of the valve replacement device according to the embodiment of FIG. 40A without a sleeve.

FIGS. 40A and 40B show an alternative embodiment of the valve replacement device. In the embodiment shown, the valve replacement device employs the valve frame 3300 shown in FIGS. 34A-34D, in combination with two valve leaflets and a sleeve. In particular, FIG. 40A shows a sleeve 4000 having a first sleeve portion 4003 and a second sleeve portion 4004 which may be coupled to the valve frame 3300, while FIG. 40B shows the valve frame 3300 with the sleeve portions removed for clarity. The valve frame 3300 may include a first leaflet attachment strut 3303 and the second leaflet attachment strut 3304, which may also be referred to herein as first and second frame sections, respectively. Each of the first and second frame sections may also be described as having a first arm (3310, 3312) and a second arm (3311, 3313) denoted by each side of the "U-shape" of the first and second frame sections. In one embodiment, as shown in FIG. 40B, the valve replacement device includes first and second leaflets 4001, 4002, respectively, forming the valve leaflets, attached to the frame. The valve frame may also include a gap 4006 disposed between first and second frame sections of the valve frame. The inventors have recognized that the presence of a gap 4006 may result in inadvertent leakage of fluid through the gap. Thus, the inventors have appreciated that providing a sleeve which extends over the gap may serve as a fluidic barrier to impede flow of fluid through the gap. As shown in FIG. 40A, the first and second sleeve portions 4003, 4004 are configured to align with and attach to the first and second frame sections of the valve frame.

The valve replacement device may be configured to replace the pulmonary valve, although, as discussed further below, the valve replacement device may be configured to replace various other native valves.

As noted above, FIG. 34A-34D show an alternative embodiment of the valve frame 3300. The frame 3300 includes top reinforcement struts 3301, lower reinforcement struts 3302, a first leaflet attachment strut 3303, a second leaflet attachment strut 3304, commissure holes 3305, and a plurality of anchoring holes 3306 along the leaflet attachment struts 3303 and 3304. It should be noted that any hole not specifically labeled is one of the anchoring holes 3306. It is contemplated that including commissure holes 3305 and anchoring holes 3306 along the leaflet attachment struts 3303 and 3304 provide anchoring points for suturing the leaflets 4001 and 4002 and sleeves 4003 and 4004 to the frame. It should be understood that any number of holes, spaced any distance from each other, of any size, could be used, as the disclosure is not so limited in this respect.

In one embodiment, the frame 3300 may be expanded such that the inner diameter of the frame may be increased up to 1.75 times the unexpanded inner diameter of the frame while maintaining valve functionality. In one embodiment, the inner diameter of the frame may be expanded from 12.7 mm to 22 mm while maintaining valve functionality. In other embodiments the inner diameter of the valve frame may be expanded until the lower reinforcement struts 3302 are generally straight such that the frame is incapable of further expansion. This feature may allow the valve to be used as a pre-stent and used as a landing site for a trans-catheter valve-in-valve procedure, as would be appreciated by one of skill in the art. In one embodiment, the inner diameter of frame 3300 in the unexpanded state is 12.7 mm, and the inner diameter of frame 3300 will be 26 mm when the lower reinforcement struts 3301 are completely expanded.

In one embodiment, the frame 3300 is made of a material with a high tensile strength, minimal elastic recoil, is resistant to fatigue, and is balloon expandable. In one embodiment, the valve frame 3300 is laser cut out of a tube of 316L stainless steel, although any other materials that possess the desired properties are contemplated. In one embodiment, the tube is 25.10 mm long, have an inner diameter of 12.7 mm, and have an outer diameter of 13.71 mm in its unexpanded state.

In one embodiment, the dimension of the top reinforcement struts 3301, lower reinforcement struts 3302, and leaflet attachment struts 3303 and 3304 each have different widths to allow for symmetrical balloon expansion. In some embodiments, it is contemplated that the top reinforcement struts 3301 each have a width W1, which in one embodiment is 0.55 mm wide. The lower reinforcement struts 3302 each have a width W2, which in one embodiment is 0.45 mm wide. The leaflet attachment struts 3303 and 3304 each have a width W3, which in one embodiment is 0.40 mm wide. While the dimension along the length of the frame can be varied to a desired width, the wall thickness in the radial direction is relatively constant, because as described above, in one embodiment, the frame is laser cut from a single tube.

Figure 41:
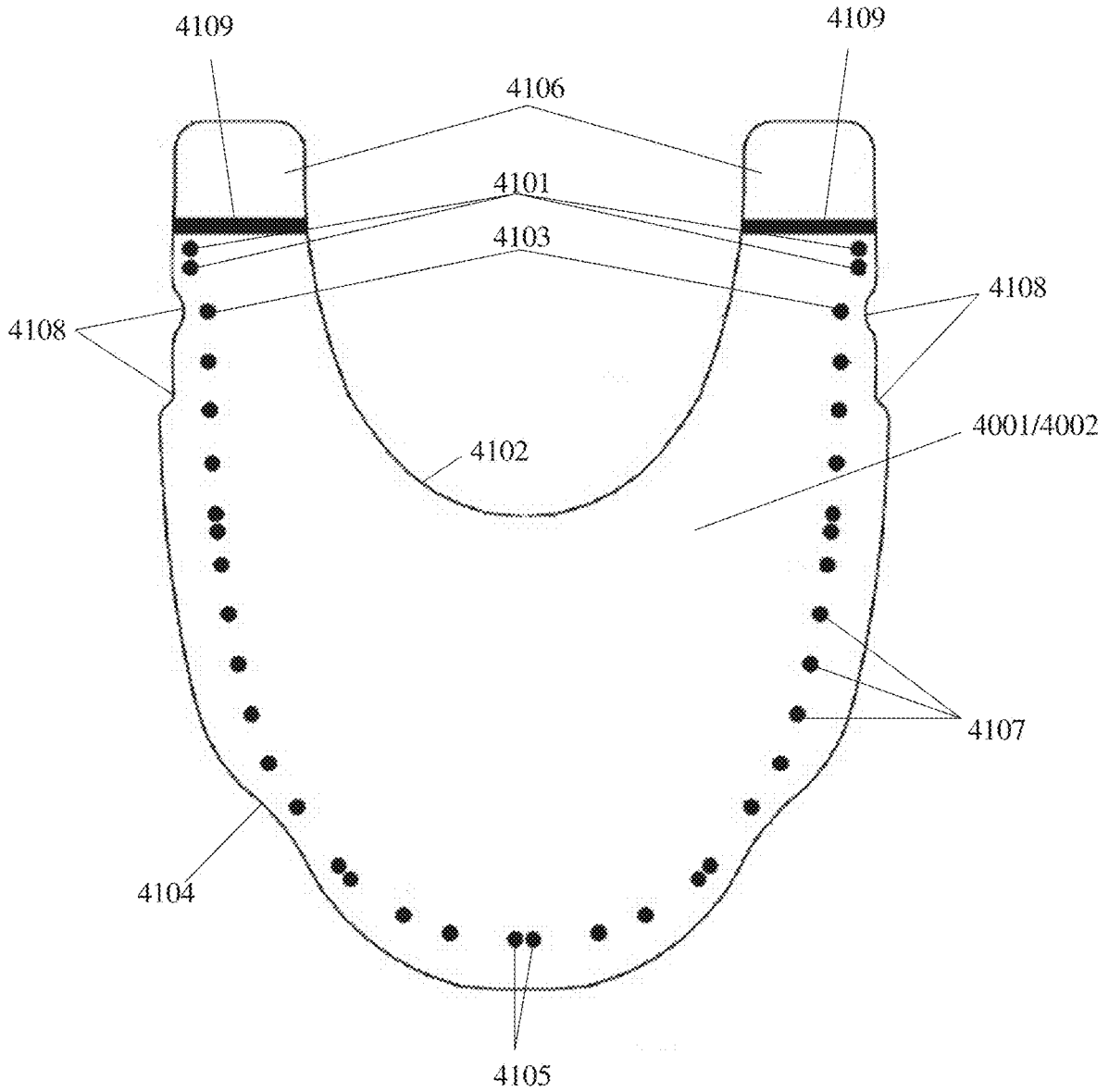
FIG. 41 is a side view of a leaflet according to one embodiment.

FIG. 41 shows an embodiment of one of the leaflets 4001 and 4002, the leaflets being substantially identical to each other, with a free edge 4102, an outer edge 4104, attachment tabs 4106, commissure points 4101, upper fixation points 4103, lower fixation points 4105, and a plurality of anchoring points 4107. It should be noted that any point not specifically labelled may be considered an anchoring point 4107.

It should be appreciated that the leaflets 4001 and 4002 are configured to mimic the geometry of native human venous valves, which enables preserved valve functionality across a wide range of dimensions. Once implanted, the orientation, positioning and geometry of the leaflets 4001 and 4002 will allow the flow of blood in one direction while preventing blood flow in the other direction. The orientation, positioning and geometry of the leaflets 4001 and 4002 will allow the flow of blood in one direction while preventing blood flow in the other direction, as the inner diameter of the valve opening expands.

Figure 44:
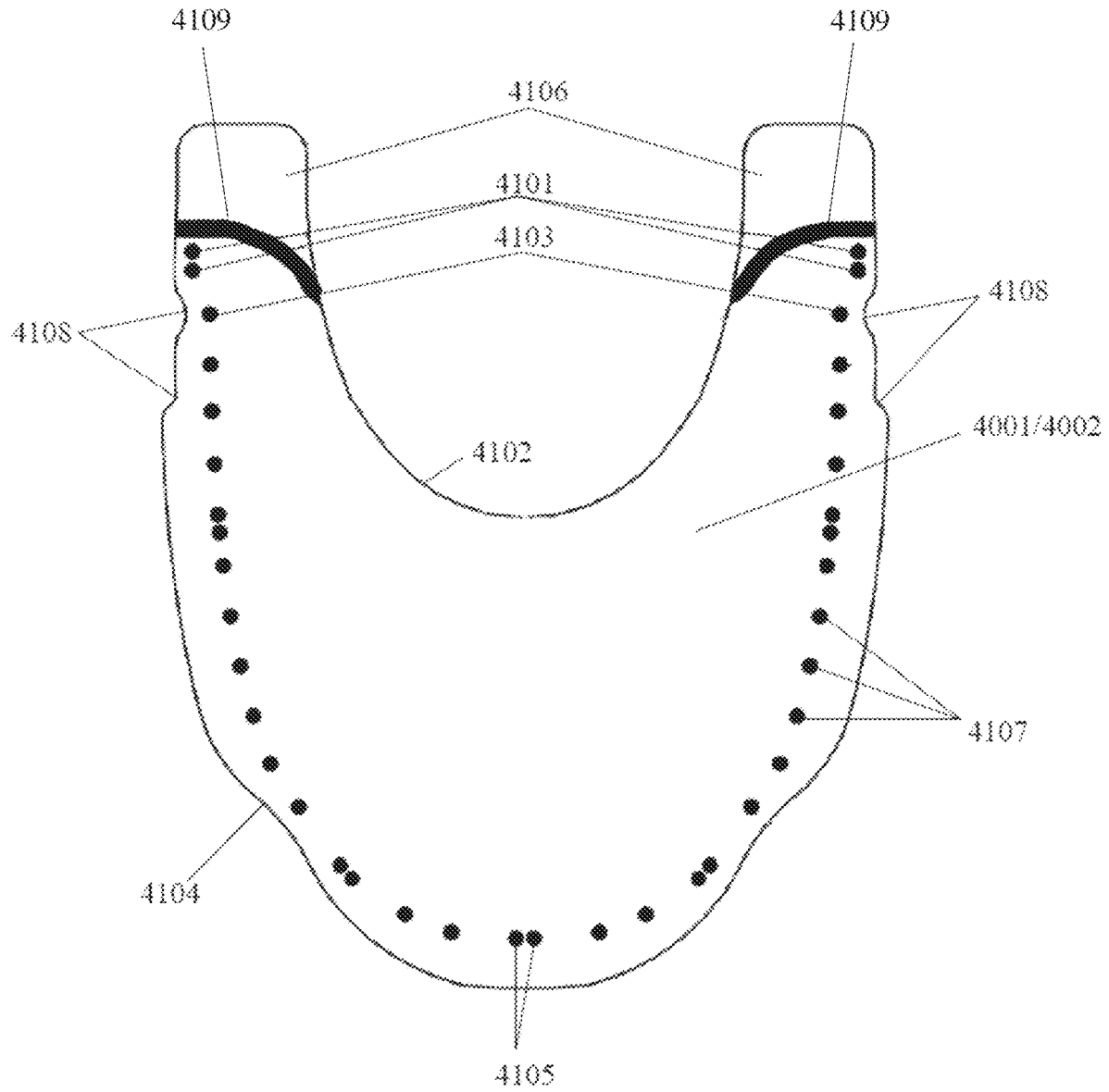
FIG. 44 is a side view of a leaflet according to another embodiment.

In one embodiment, the first leaflet 4001 is attached to the inside of the first leaflet attachment strut 3303 by suturing the commissure points 4101 to the corresponding commissure holes 3305, the upper fixation points 4103, lower fixation points 4105, and plurality of anchoring points 4107 to the corresponding anchoring holes 3306. First, the first leaflet 4001 is fixed to the first leaflet attachment strut 3303 by securing the upper fixation points 4103 to the corresponding anchoring holes 3306. Then, the lower fixation points 4105 are secured to the corresponding anchoring holes 3306. Then, the plurality of anchoring points 4107 are attached to the corresponding anchoring holes 3306. The attachment tabs 4106 give an assembler something to grip as they attach the first leaflet 4001 to the frame 3300. The attachment tabs may be of any suitable shape as the disclosure is not so limited. For example, FIG. 41 shows that the attachment tabs 4106 may be substantially rectangular as the attachable ends 4109 form a substantially linear attachment between the leaflets at the commissures (region of distal frame where the two valve leaflets converge). In other embodiments however, such as FIG. 44, the attachable ends 4109' may be substantially curved. The inventors have found that, in some embodiments, curved attachable ends 4109' may help promote coaptation of the leaflets at the commissures. It should be understood that in other embodiments, the leaflets may be produced without any attachment tabs. The second leaflet 4002 is attached to the second leaflet attachment strut 3304 using the same method as outlined above. The commissure points 4101 on the first leaflet 4001 are then sutured to the corresponding commissure points 4101 on the second leaflet 4002, and then the commissure points 4101 on both leaflets are sutured to the corresponding commissure holes 3305, such that the outer edge 4104 of the first leaflet 4001 is in contact and aligned with the outer edge 4104 of the second leaflet 4002. The attachment tabs on both leaflets are removed after the leaflets are attached.

Without wishing to be bound by theory, this leaflet attachment sequence is used to ensure proper alignment of each of the leaflets 4001 and 4002, and to ensure that each of the commissure points 4101, upper fixation points 4103, lower fixation points 4105, and a plurality of anchoring points 4107 are sutured without any material folding, impingement or pinwheeling to avoid localized areas of tension and stress concentration, and to ensure the functional surface area of each of the leaflets 4001 and 4002 is adequate for the device to function across the full range of expansion diameters. In some embodiments, this full range of expansion diameters is up to 1.75 times the inner diameter of the unexpanded valve frame 3300. It should be understood that any leaflet attachment process that provides for proper alignment and leaflet tension is contemplated.

It is contemplated that the first leaflet 4001 and the second leaflet 4002 are attached to the corresponding leaflet attachment struts 3303 and 3304 using interrupted sutures, although any other suture method, including partially interrupted sutures or continuous sutures is contemplated. Again, without wishing to be bound by theory, interrupted sutures may allow for control of tension along the length of leaflet-frame attachment. Also, if one suture fails, others will keep the leaflet secure to the frame.

Turning back to FIG. 41, in this embodiment, the free edge 4102 has a U-shaped profile, and the outer edge 4104 has an extended U-shaped profile, such that the perpendicular distance from the free edge 4102 to the outer edge 4104 is greatest at the vertex of the free edge 4102. In this embodiment, the outer edge 4104 includes notches 4108 such that the outer edge 4104 aligns with the corresponding leaflet attachment struts 3303 and 3304. This geometry allows the frame 3300 to expand without stretching the leaflets 4001 and 4002.

It is contemplated that the material used for the leaflets 4001 and 4002 is orientated such that the most extensible direction is from the free edge 4102 to the outer edge 4104. Such an orientation may be advantageous as it can serve to increase the amount of leaflet coaptation (area of contact between leaflets 4001 and 4002) during use.

In one embodiment, the leaflets 4001 and 4002 have a minimal amount of stretch across the width of the leaflets. Such a property may minimize any billowing of the leaflets during use.

In one embodiment, the leaflets 4001 and 4002 are manufactured from ePTFE membrane although any suitable material is contemplated, including a synthetic polymer, a tissue-engineered construct, a decellularized homologous tissue engineered leaflet, a gluteraldehyde-treated bovine pericardium, a gluteraldehyde-treated porcine pericardium, a photo-oxidized bovine pericardium, a bovine jugular vein valve.

In one embodiment, the leaflets are 0.1 mm thick, although any other material thickness that allows for proper valve functionality is contemplated. In one embodiment, the leaflets 4001 and 4002 are 23.56 mm wide, although any other width which allows for proper valve functionality is contemplated. The distance from the lower fixation points 4105 to the bottom of the attachment tabs 4106 may be approximately 24.29 mm, although any other distance which allows for proper valve functionality is contemplated. The distance from the lower fixation points 4105 to the vertex of the free edge 4102 may be approximately 14.28 mm, although any other distance which allows for proper valve functionality is contemplated. In one embodiment, the leaflets 4001 and 4002 have a surface area of 328 mm$^2$.

In one embodiment, the commissure points 4101, upper fixation points 4103, lower fixation points 4105, and plurality of anchoring points 4107 are located at an optimal distance from the outer edge 4104 to minimize the risk of suture pull out. Generally, the more tension a particular section of the leaflets 4001 and 4002 are under, the further the commissure points 4101, upper fixation points 4103, lower fixation points 4105, and plurality of anchoring points 4107 in that region are from the outer edge 4104. In one embodiment, a finite element analysis similar to the one shown in FIG. 23D may be used to determine how much tension a particular section of the leaflets 4001 and 4002 will be under when the leaflets are expanded, and anchoring points 4107 in that particular section may be positioned the optimal distance from the outer edge 4104 based on this determination. In one embodiment, the anchoring points 4107 that are approximately half-way down the leaflets 4001 and 4002 would be under the most tension when the device is in an expanded configuration and are therefore located further form the outer edge 4104 than other anchoring points. In one embodiment, such anchoring points are located at least 1.7 mm from the outer edge 4104.

In this embodiment, the commissure points 4101, upper fixation points 4103, lower fixation points 4105, and plurality of anchoring points 4107 are marked prior to valve assembly. In some embodiments, the commissure points 4101, upper fixation points 4103, lower fixation points 4105, and plurality of anchoring points 4107 may be pre-formed holes.

Figure 42:
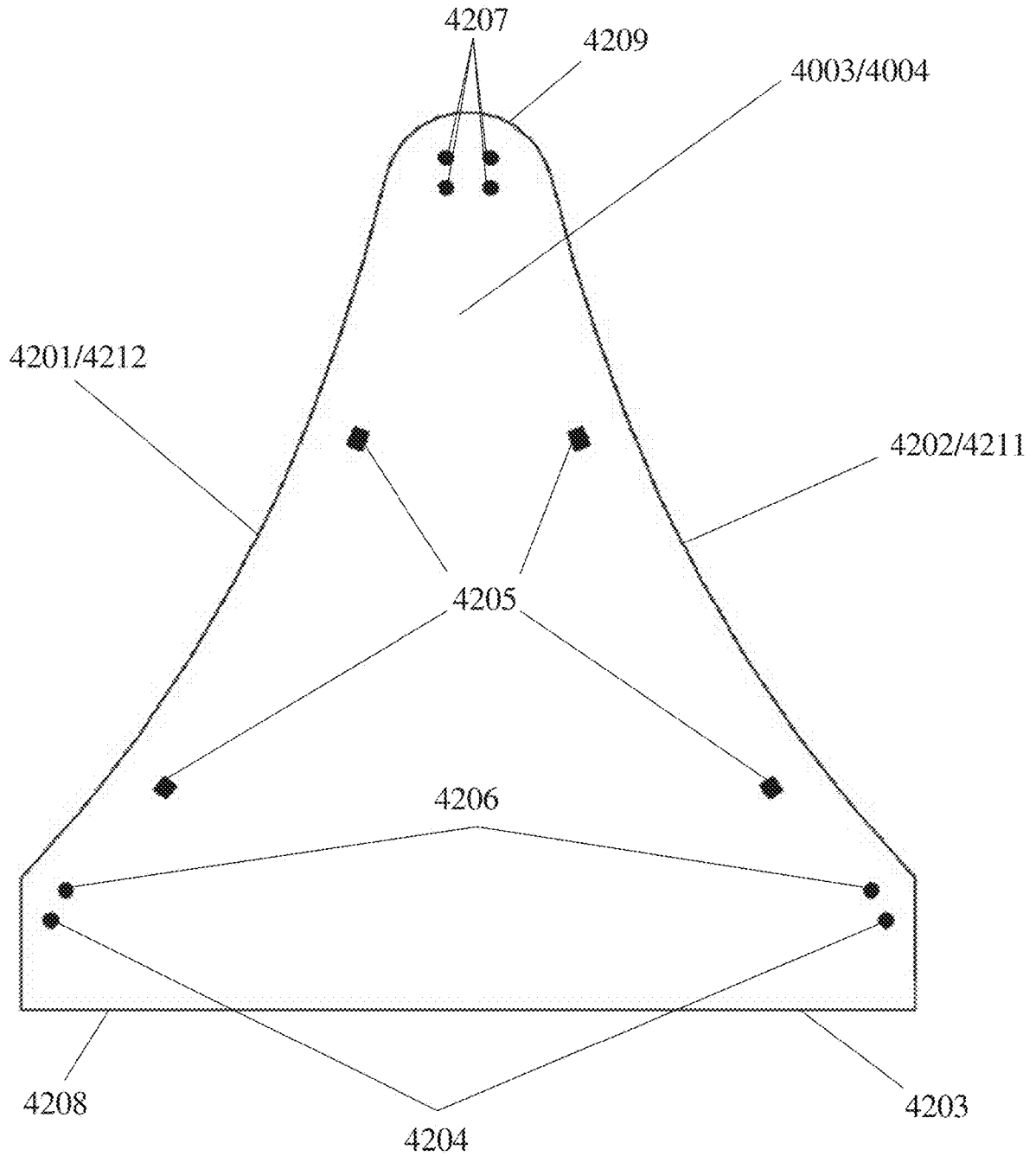
FIG. 42 is a side view of a sleeve according to one embodiment.

As noted above, in this embodiment, the valve replacement device includes a sleeve. The sleeve may be formed of two separate sleeve portions. FIG. 42 shows an embodiment of the first and second sleeve portions 4003 and 4004, the sleeve portions being substantially identical to each other. The first sleeve portion 4003 includes a first anchored edge 4201 and a second anchored edge 4202 while the second sleeve portion 4004 includes a third anchored edge 4211 and a fourth anchored edge 4212. The sleeve portions 4003 and 4004 also include a sewing cuff 4203, sewing cuff fixation points 4204, initial anchor points 4205, fixation points 4206, and plurality of commissure fixation points 4207.

In one embodiment, the sleeves 4003 and 4004 allow for the fixation of the device to the native tissue. The sleeves 4003 and 4004 are configured to prevent leakage of blood around the outside of the valve replacement device when the device is attached to the native tissue. Employing ePTFE may prevent tissue ingrowth, thus allowing for the valve replacement device to expand with minimal resistance and avoidance of damage to the surrounding tissue. Such a material may prevent the formation of abnormal layers of fibrovascular or granulation tissue.

In some embodiments, the first sleeve portion 4003 may be attached to the outside of the valve frame 3300 by securing the first sleeve portion 4003 to the corresponding anchoring holes 3306 in the leaflet attachment struts 3303 and 3304. The first sleeve portion 4003 is aligned so the first anchored edge 4201 attaches to the first arm 3310 of the first leaflet attachment strut 3303, and the second anchored edge 4202 attaches to the first arm 3312 of the second leaflet attachment strut 3304.

To attach the first sleeve portion 4003 to the frame 3300, the initial anchor points 4205 are secured to the frame 3300 at the corresponding anchoring holes 3306 to align the first sleeve portion 4003 properly, such that the anchored edges 4201 and 4202 of the first sleeve portion 4003 at least partially wrap around the leaflet attachment struts 3303 and 3304. In some embodiments, the first sleeve portion 4003 may be secured to the frame 3300 such that the anchored edges 4201 and 4202 are secured to the leaflet attachment struts 3303 and 3304, but do not partially wrap around them. The first edge 4201 and the second edge 4202 are then anchored to the frame 3300 by attaching a continuous suture to each of the fixation points 4206, removing the sutures attached to the initial anchor points 4205, and running each continuous suture up the corresponding edge 4201 and 4202 of the first sleeve portion 4003 through each of the corresponding anchoring holes 3306. The continuous sutures are then passed in through the lower of the commissure fixation points 4207 on the sleeve, through the commissure holes 3305 towards the center of the valve frame, out through the upper of the commissure holes 3305 away from the center of the valve frame, through the upper commissure fixation points 4207, and tied together at the top of the first sleeve portion 4003. Although the sleeves 4003 and 4004 are attached to the corresponding leaflet attachment struts 3303 and 3304 using continuous sutures, any other suture method, including partially interrupted sutures or interrupted sutures is contemplated.

The second sleeve portion 4004 is attached to the outside of the valve frame 3300 by securing the second sleeve portion 4004 to the corresponding anchoring holes 3306 in the leaflet attachment struts 3303 and 3304. The second sleeve portion 4004 is aligned so the third anchored edge 4211 attaches to the second arm 3311 of the first leaflet attachment strut 3303, and the fourth anchored edge 4212 attaches to the second arm 3313 of the second leaflet attachment strut 3304. The method of attaching the second sleeve portion 4004 to the frame 3300 is substantially identical to the method of attaching the first sleeve portion 4003 to the frame 3300.

After the first sleeve portion 4003 and the second sleeve portion 4004 are attached to the outside of the frame 3300, the sleeves are attached to each other by suturing the sewing cuff fixation points 4204 on the first sleeve portion 4003 to the corresponding sewing cuff fixation points 4204 on the second sleeve portion 4004. This may prevent leakage of blood around the outside of the valve replacement device. This sleeve attachment method is used to ensure proper alignment of each of the sleeves 4003 and 4004. It should be understood that any sleeve attachment method that provides for proper alignment is contemplated.

In this embodiment, the valve replacement device is fixed to the native tissue by suturing the valve to the native tissue through the sewing cuff 4203 of the sleeves 4003 and 4004. It is contemplated that the sutures are located at a distance from the bottom edge of the sleeves large enough to reduce the risk of tear out. In one embodiment this distance is a minimum of 2 mm. The distance between the sutures is small enough to prevent leakage of blood between the sutures. In one embodiment, this distance is a maximum of 3 mm. It is contemplated that interrupted horizontal mattress sutures, continuous running sutures, or a combination of partially interrupted and continuous sutures are used to secure the valve replacement device to the native tissue.

In this embodiment, the sleeves 4003 and 4004 are generally bell shaped, and are vertically bilaterally symmetrical. The sewing cuff 4203 extends from the bottom of each of the sleeves 4003 and 4004 to the beginning of the bell curve on each of the sleeves 4003 and 4004.

In one embodiment, the material for the sleeves 4003 and 4004 is orientated such that the sleeves 4003 and 4004 are most extensible across their width to allow for valve expansion. In this embodiment, the sleeves 4003 and 4004 can expand across their width a distance sufficient to allow the valve replacement device to expand to an inner diameter of at least 22 mm. In some embodiments, the sleeves 4003 and 4004 can expand across their width a distance sufficient to allow the valve replacement device to expand to an inner diameter of 26 mm. In this instance, the valve can therefore expand past its functional range so it can be used as a pre-stent and landing zone for a transcatheter valve-in-valve replacement procedure.

The sleeves 4003 and 4004 may be constructed of ePTFE stretch tube graft, the tube graft having a thin film of ePTFE on the exterior. In one embodiment, the ePTFE stretch tube graft may be 1 mm thick, but any tube graft thickness which allows for proper sleeve functionality is contemplated. In some embodiments, a suitable sleeve thickness may be greater than or equal to 0.25 mm, 0.5 mm, 0.75 mm, 0.9 mm, 1 mm, 1.1 mm, 1.25 mm, 1.5 mm, 1.75 mm, 2 mm, or any other suitable sleeve thickness value which may be greater or lesser than those disclosed herein. To construct the sleeves 4003 and 4004, a tube graft of suitable length is cut in half. Because ePTFE stretch tube graft is most extensible in the longitudinal direction, each sleeve is cut out of the ePTFE tube graft so that the width of each sleeve is in the longitudinal direction of the ePTFE tube graft. Because the outer film has a tighter microstructure than the rest of the graft, this may minimize native tissue ingrowth into the sleeves 4003 and 4004 and allow for unimpeded valve expansion, the side of the sleeves 4003 and 4004 which has the film is designated as the side of the sleeves 4003 and 4004 facing the native tissue. In some embodiments, one or more layers of ePTFE film may be provided on the outer surface of the sleeves. The outer ePTFE film layer may provide benefits such as limiting native tissue ingrowth into the sleeves, and/or discouraging an excessive fibrotic tissue response at the suture line, which may hinder the ability to effectively balloon expand the valve post-implantation. In some such embodiments, the outer ePTFE film may be bonded with one another and/or the ePTFE on the exterior of the tube graft.

In one embodiment, the sleeves 4003 and 4004 each have a width at the base sufficient to cover at least half the circumference of the valve frame 3300, such that the sleeves 4003 and 4004 are not tightly wrapped around the frame 3300 when the frame is unexpanded. In one embodiment, that width at the base is 30 mm. In one embodiment, the sleeves 4003 and 4004 each have a width at the base sufficient to cover half the circumference of the valve frame 3300, such that the sleeves 4003 and 4004 are tightly wrapped around the frame 3300 when the frame is unexpanded. In one embodiment, the sleeves 4003 and 4004 each have a length sufficient to cover the entire length of the valve frame 3300. In one embodiment, that length is 30.11 mm. In one embodiment, the sewing cuff 4203 is long enough to allow for effective placement of the sutures fixing the valve replacement device to the native tissue. In one embodiment, that sewing cuff length is 4.40 mm. The sewing cuff length may be trimmed (shortened) during the implant procedure, to optimize device fixation to the native tissue. Though, it is noted that the sewing cuff length must extend beyond the most inferior portion of frame 3300, to ensure the circumferential suture line (location of device fixation to the native tissue) is below the level of the valve opening.

In some embodiments, the sleeve according to embodiments disclosed herein may have a proximal end 4208 and a distal end 4209, where the proximal end is denoted by the base of the sleeve where the sewing cuff 4203 is located, and wherein the distal end is denoted by the region in which the upper commissure fixation points 4207 are located (see FIG. 42). Thus, in some embodiments, the proximal end of the sleeve may serve as a sewing cuff which may be sutured or otherwise attached to the implantation site to secure the valve replacement device in a desired position relative to the implantation site. In some embodiments, the valve replacement device may be attached to the implantation site solely at the sewing cuff. In addition or alternatively, the distal end and/or other portions of the sleeve may be used to attach the valve replacement device to the implantation site as the disclosure is not so limited.

In one embodiment, the sewing cuff fixation points 4204, initial anchor points 4205, fixation points 4206, and several of the commissure fixation points 4207 are pre-marked. However, it should be understood that, in other embodiments, any of these points may not be pre-marked, or be pre-formed holes, or all be pre-marked.

Figure 43A:
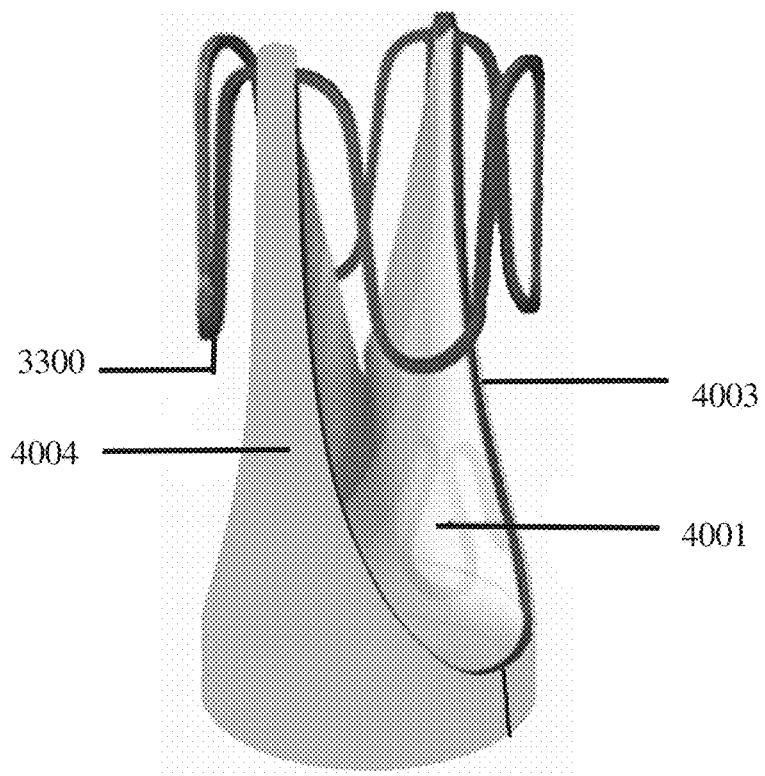
FIG. 43A is a perspective view of the valve replacement device in an unexpanded configuration according to one embodiment.
Figure 43B:
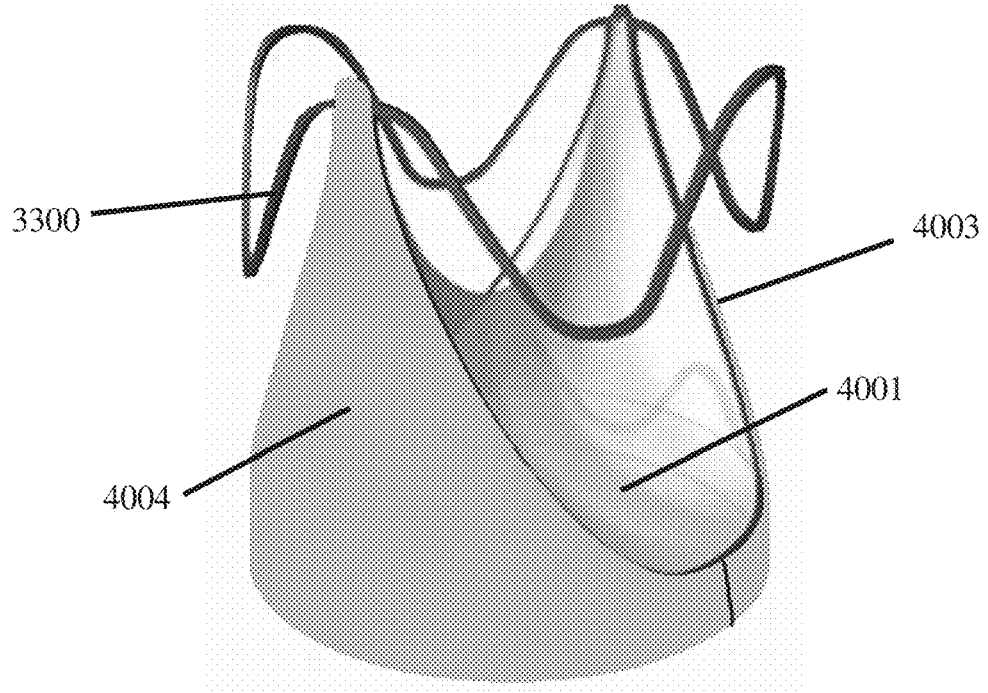
FIG. 43B a perspective view of the valve replacement device of FIG. 43A in an expanded configuration.

FIGS. 43A and 43B show an embodiment of the valve replacement device similar to that of FIGS. 40A and 40B, where the valve replacement device includes a valve frame 3300, a valve leaflet 4001, and a sleeve comprising a first sleeve portion 4003 and a second sleeve portion 4004. FIG. 43A shows an embodiment where the valve frame 3300 is in an unexpanded position such that the inner diameter is less than that of FIG. 43B, which shows the valve frame 3300 in an expanded position. In some embodiments, the valve frame 3300 may be constructed and arranged such that the opening is substantially circular, such as in FIGS. 43A and 43B.

Referring back to FIGS. 40A-B and FIG. 42, the first sleeve portion 4003 may include a first anchored edge 4201 and a second anchored edge 4202 while the second sleeve portion 4004 may include a third anchored edge 4211 and a fourth anchored edge 4212. In some embodiments, at least one of the first anchored edge 4201 and the second anchored edge 4202 of the first sleeve portion 4003 and at least one of the third anchored edge 4211 and the fourth anchored edge 4212 of the second sleeve portion 4004 may be configured to be aligned with and attached to at least one of the first arm (3310, 3312) and the second arm (3311, see 3313 in FIG. 34A) of the first frame section and/or the second frame section of the valve frame 3300. For example, the first anchored edge 4201 and the second anchored edge 4202 of the first sleeve portion 4003 may be aligned with and attached to the first arm 3310 of the first frame section and the first arm 3312 of the second frame section, respectively. Likewise, in another example, the third anchored edge 4211 and the fourth anchored edge 4212 of the second sleeve portion 4004 may be aligned with and attached to the second arm (3311) of the first frame section and the second arm (3313) of the second frame section, respectively.

It should be understood that in some embodiments described above, the valve replacement device is configured to replace the pulmonary valve. However, the valve replacement device may be configured to replace other valves as well. Configuring the valve replacement device to replace other valves may involve altering some aspects of the valve replacement device, including the scale of the device, leaflet material properties, and thickness of the leaflets, as discussed further below.

The valve replacement device may be scaled up or down as appropriate for the patient age and body size, or the valve it is replacing. The table below lists the nominal diameter, maximal functional diameter, and maximal frame diameter of several embodiments of a valve replacement device sealed up or down. The nominal diameter is the inside diameter of the valve frame 3300 when the valve frame is unexpanded, the maximal functional diameter is the maximum inside diameter the valve frame 3300 may be expanded to while maintaining valve functionality, and the maximal frame diameter is the maximum inside diameter the valve frame 3300 may be expanded to beyond the maximal functional diameter. The frame aspect ratio is maintained as the valve replacement device is scaled, such that the frame length:frame diameter ratio remains the same. It should also be understood that the examples listed below are not exhaustive, such that any appropriate scale of the valve replacement device is contemplated.

| Nominal diameter (ID) | Maximal functional diameter (ID) | Maximal frame diameter (ID) |
| --- | --- | --- |
| 8 mm | 14 mm | 17 mm |
| 10 mm | 17 mm | 22 mm |
| 12.7 mm | 22 mm | 26 mm |
| 14 mm | 24 mm | 30 mm |
| 16 mm | 28 mm | 34 mm |
| 18 mm | 32 mm | 38 mm |

The appropriate thickness of leaflets 4003 and 4004 is dependent on the blood pressure and flow velocity the valve replacement device will encounter when implanted, as well as the material properties of the material used for the leaflets. Because various valves in native tissue encounter different blood pressure and flow velocity, the appropriate material properties and thickness range of the leaflets changes based on which native valve the valve replacement device is replacing. Without wishing to be bound by theory, the table below lists potentially appropriate leaflet thickness ranges for different use cases of the valve replacement device.

| Application | Leaflet material thickness range |
| --- | --- |
| Pulmonary valve replacement (right sided semilunar valve) | 0.05 to 0.2 mm |
| Pulmonary valve conduit (right sided) | 0.05 to 0.2 mm |
| Aortic valve replacement (left sided semilunar valve) | 0.2 to 0.8 mm |
| Mitral valve replacement (left sided atrioventricular valve) | 0.2 to 0.8 mm |
| Tricuspid valve replacement (right sided atrioventricular valve) | 0.05 to 0.5 mm |
| Venous valve prosthesis (Lower extremity veins) | 0.02 to 0.2 mm |

It should be understood that when the valve replacement device is used as a pulmonary valve conduit, the valve replacement device would be assembled inside a tube positioned outside of the heart to connect the right ventricle and pulmonary artery. In one embodiment, the tube may be constructed from an expandable synthetic material. In one embodiment, the sewing cuff of the valve replacement device may be sutured circumferentially to the inside of the expandable synthetic tube such that the suture line location is proximal to the center of the tube. In one embodiment, the expandable synthetic tube containing the valve replacement device may be proximally sutured to the right ventricle and distally sutured to the pulmonary artery. In one embodiment, the tube may be a pulmonary or aortic homograft. In one embodiment, native leaflets inside of the homograft may be resected and the valve replacement device may be sutured circumferentially to the inside of the homograft at the level of the native homograft leaflets. In one embodiment, the homograft containing the valve replacement device may be proximally sutured to the right ventricle and distally sutured to the pulmonary artery.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A valve replacement device, comprising:
a valve frame comprising first and second U-shaped frame sections connected at one end by a pair of commissures, the valve frame defining an opening for the passage of fluid, the first and second frame sections each having first and second arms, the valve frame being expandable to permit an increase in a diameter of the opening over a diameter size range of the opening;
a valve leaflet coupled to the valve frame, the valve leaflet having an open configuration in which the opening is exposed, and a closed configuration in which the valve leaflet at least partially covers the opening, wherein the valve leaflet is configured to be moveable between the open and closed configurations over the diameter size range of the opening; and
a sleeve coupled to the valve frame, the sleeve having a first expandable direction orientated to permit the increase in the diameter of the opening of the valve frame,
wherein the sleeve further comprises a film, wherein the film is configured to minimize native tissue ingrowth into the sleeve.

2. The valve replacement device of claim 1, wherein the film is on an exterior of the sleeve.

3. The valve replacement device of claim 1, wherein the film has a tighter microstructure than the rest of the sleeve.

4. The valve replacement device of claim 1, wherein the sleeve comprises a first sleeve portion and a second sleeve portion coupled to the valve frame.

5. The valve replacement device of claim 4,
wherein the first and second sleeve portions are constructed from sections of tube graft, the sections of tube graft having a longitudinal direction, and wherein the first expandable direction of the sleeve is the longitudinal direction of the sections of tube graft.

6. The valve replacement device of claim 1, wherein a proximal end of the sleeve is configured for suture fixation to native structures.

7. The valve replacement device of claim 1, wherein the valve frame is expandable to permit an increase in the diameter of the opening past a functional range of the valve leaflet in order to configure the valve replacement device as a pre-stent for a transcatheter valve-in-valve replacement procedure.

8. The valve replacement device of claim 1, wherein the valve frame is expandable to permit the increase in the diameter of the opening to be greater than 22 mm.

9. The valve replacement device of claim 1, wherein the valve leaflet is configured to maintain a constant surface area with expansion of the valve frame.

10. The valve replacement device of claim 1,
wherein the valve frame has a plurality of holes through the valve frame,
wherein the valve leaflet comprises a first leaflet and a second leaflet,
wherein the first leaflet has an outer edge, and is coupled to the valve frame using at least some of the plurality of holes through the valve frame, and the second leaflet has an outer edge, and is coupled to the valve frame using at least some of the plurality of holes through the valve frame,
wherein the first and second leaflets have a plurality of leaflet attachment points for coupling the first and second leaflets to the valve frame, and
wherein the plurality of leaflet attachment points are located a non-uniform distance from the outer edges of the first and second leaflets.

11. The valve replacement device of claim 10,
wherein the plurality of holes are through the first and second U-shaped frame sections and through the pair of commissures,
wherein the first leaflet is coupled to the holes in the first U-shaped frame section and the pair of commissures, and
wherein the second leaflet is coupled to the holes in the second U-shaped frame section and the pair of commissures.

12. The valve replacement device of claim 11,
further comprising a first reinforcement feature that connects the pairs of commissures,
further comprising a second reinforcement feature that connects the first and second U-shaped frame sections, and
wherein the first reinforcement feature is of a different shape than the second reinforcement feature.

13. The valve replacement device of claim 1, wherein the valve frame includes a plurality of holes through the valve frame, wherein the valve leaflet is coupled to the valve frame using at least some of the plurality of holes through the valve frame, and wherein the sleeve is coupled to the valve frame using at least some of the plurality of holes through the valve frame.

14. The valve replacement device of claim 1, wherein the sleeve is formed from ePTFE.

* * * * *